US011560600B2

(12) United States Patent
Quesada-Ocampo et al.

(10) Patent No.: US 11,560,600 B2
(45) Date of Patent: Jan. 24, 2023

(54) METHODS FOR DIAGNOSIS OF *PSEUDOPERONOSPORA CUBENSIS* INFECTION AND SELECTION OF PLANT RESISTANCE GENES TO THE SAME

(71) Applicant: NORTH CAROLINA STATE UNIVERSITY, Raleigh, NC (US)

(72) Inventors: Lina Quesada-Ocampo, Cary, NC (US); Saunia Withers, Durham, NC (US); Elsa Beatriz Gongora-Castillo, San Antonio Merida (MX)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 972 days.

(21) Appl. No.: 16/331,191

(22) PCT Filed: Sep. 5, 2017

(86) PCT No.: PCT/US2017/050059

§ 371 (c)(1),
(2) Date: Mar. 7, 2019

(87) PCT Pub. No.: WO2018/048792

PCT Pub. Date: Mar. 15, 2018

(65) Prior Publication Data

US 2019/0276902 A1 Sep. 12, 2019

Related U.S. Application Data

(60) Provisional application No. 62/384,817, filed on Sep. 8, 2016.

(51) Int. Cl.
*C12Q 1/6895* (2018.01)
*C07K 14/37* (2006.01)

(52) U.S. Cl.
CPC ............ *C12Q 1/6895* (2013.01); *C07K 14/37* (2013.01); *C12Q 2600/13* (2013.01)

(58) Field of Classification Search
None
See application file for complete search history.

(56) References Cited

FOREIGN PATENT DOCUMENTS

EP 2444498 4/2012

OTHER PUBLICATIONS

Burkhardt et al, 2015, MPMI vol. 28(3):298-309. http://dx.doi.org/10.1094/MPMI-09-14-0300-FI.*
Summers et al (2015, PLoS ONE 10(11): e0143665. doi:10.1371/journal.pone.0143665.*
Gen Bank Accession No. AC242106 (2010, https://www.ncbi.nlm.nih.gov/nuccore/ACor42106).*
International Preliminary Report on Patentability corresponding to International Patent Application PCT/US2017/050059, dated Mar. 21, 2019 7 pages.
International Search Report and Written Opinion corresponding to International Patent Application PCT/US2017/050059, dated Dec. 14, 2017, 10 pages.
Cohen et al., "Seed Transmission of Pseudoperonospora cubensis", Plos One, 9(10):1-12 (2014) Abstract.
Holdsworth et al. "Development of Downy Mildew-resistant Cucumbers for Late-season Production in the Northeastern United States" HortScience, 49(1):10-17 (2014).
Hong et al. "The production of polyclonal and monoclonal antibodies in mice using novel immunization methods", J Immunol Methods, 120(2):151-157 (1989).
GenBank accession No. CF862060 (2003).
GenBank accession No. FG054005 (2008).
GenBank accession No. BE583118 (2010).

* cited by examiner

*Primary Examiner* — Anne Kubelik
(74) *Attorney, Agent, or Firm* — Myers Bigel, P.A.

(57) ABSTRACT

The invention is directed to methods of diagnosing a *Pseudoperonospora cubensis* infection in a cucurbit plant, comprising detecting at least one nucleotide sequence selected from the group of nucleotide sequences of SEQ ID NOs: 1-52, or any combination thereof, in a sample from a cucurbit plant or in an environmental sample, thereby diagnosing a *P. cubensis* infection. Also provided is a method of selecting a cucurbit plant comprising at least one resistance gene, the method comprising introducing into the cucurbit plant a nucleotide sequence of any one of SEQ ID NOs: 1-52, wherein the expression of the nucleotide sequence produces a hypersensitive response in a cucurbit plant comprising a resistance gene, thereby identifying the cucurbit plant as comprising a resistance gene; and selecting the plant having the hypersensitive response and identified as comprising said resistance gene.

10 Claims, 6 Drawing Sheets

Specification includes a Sequence Listing.

SEQUENCE LISTING

<160> NUMBER OF SEQ ID NOS: 52

<210> SEQ ID NO 1
<211> LENGTH: 447
<212> TYPE: DNA
<213> ORGANISM: Pseudoperonospora cubensis

<400> SEQUENCE: 1

```
atgactctcc ttcatactac tttgatcgtc tctttcgcag ctcttgcggt gcttcgacct     60

gccagcgtga gcgctgccag ctgcacggac gacgagcaat ctaccatcaa cagcgtgtac    120

acggacctga ccaacagcac aatgtgcaca gatctcattt ccaactcgga cactacgttt    180

ctcgactatt gcaagaatag tggctgcatc tcaaagctca gtaccgccgt tgatcagcta    240

cctagctgca ctgaagacta tgagatcaac cgcaaggcag gactgcaaga tatcgttgag    300

tactgcatca aggtgcagga gatgacgaat caatcagcgc ctggcgagaa cggcactgag    360

tcggtcgtct cgggcgcctc gagaagcgct ctggccacgg gcgtattgac tgcccagctg    420

tgtgcggcac tatacttctt cgcatga                                        447
```

<210> SEQ ID NO 2
<211> LENGTH: 717
<212> TYPE: DNA
<213> ORGANISM: Pseudoperonospora cubensis

<400> SEQUENCE: 2

```
atgaatctct ggtcaatact tttcttgtac gccgccgctg tcgaagctac gcctatcctc     60

cccgacgaaa tgataccatt cgaccaaccc cttgcacact cggacgctga aaaatctgcg    120

gtcagattca agccaagtct tttagtcatc gatggatgca tgccatacgc ggccgtcaat    180

gcagcaggaa acacgaacaa tgggcttaaa ccgttgggag gtgtaaacga aggctgcaat    240

gcgcctaaga agggtcagat atacggtcga gccacgtggc acaaaacgta ctgggctatc    300

atgtacgcat ggtatttccc caaggcagtt ataccaaatg gaaaaggcgg gatgaagcac    360

gattgggaaa gtgtcgttat ttggatcacc aatccagccg tcaaaaaccc aaaaataatc    420

gctgtggcaa ctaccaagtt cttcgacagc tacaagaagt accgtcctcc acctcccggt    480

actgtgaaag gcgacaccac gctgattgcg tatgctccaa atcctgacga acggtatgtt    540

cacaccgtgg acgtgacgcc cgtgacaggc tcgacccagc cccttatcat gtgggaacag    600

atgcctgaac gggcgcgtgt agctctgacc aacactaaat ggggagatta tgccaaggtt    660

ccgttcattg atgtaaactt cggaagaaat ctcgatcgtg cgtggtcgtc gagataa       717
```

<210> SEQ ID NO 3
<211> LENGTH: 253
<212> TYPE: DNA
<213> ORGANISM: Pseudoperonospora cubensis

<400> SEQUENCE: 3

```
acttgatggg caaaaaggcg actagagtac tgtttttctc ctccattgtc atctccaaga     60

actcgctctt atcatcactc cttcgacgca tggtttcaaa ctgagagaca tcaaaagcgt    120

ggtgcatcac cgtctacttg ttctcctgaa acgacttcat tgcagttgta gcccttgact    180

tgcttcttcg tacgcgcgta gaaaccatac agtgtaattt cattaagctt gatgtgcgct    240

ctcaacagaa tgt                                                       253
```

<210> SEQ ID NO 4
<211> LENGTH: 775
<212> TYPE: DNA
<213> ORGANISM: Pseudoperonospora cubensis

<400> SEQUENCE: 4

```
ctaatatttt gtgtggcgac cacagccaca tttttgcgca tcctcctctt ccttcaaatc     60

gctcgtaagg gcagggtact tcacagacaa aagcgtctgg tggcactgcg agcacagctt    120

gctcgtcata aactcgtcca tgaacaccac cgtcgcgcac ttctgcaacg gccgtaccta    180

ccctttcatc ggactgggtc atgtattttg atatcatcgc ggtgactcca gagctcgcat    240

gccacgcaag tcgacatgct caccatcaga acaatatgca tcggccgcca catgagccat    300

gcgctgccaa aaaattcctt aagaaacggc tgcttcgtgc tgaagtttag catgaacgtc    360

acgttattcc agaagtactg cagtcgctcc aggtactccg tgtagctcgc ggtattgagc    420

actagtatct ctgcaggaat cctcacgtca tcacggggtg ctgtttcttc aggccctcgt    480

tcccagcagt gaaccgctcg aaaccagcca tgtgacggta cacttcgacg tcacttgcac    540

gaaatcgcgc acgttacgac gcttaggtga ggggattggc gaatccagac cggccggtct    600

tcttcctcct cctcctttcg cggcgcctcc tttgctgcga actaagaaca tctcttacac    660

cagcacataa cgcccgcatc ccggggtcta gtccaatgac ggcgtctggc aagtattcag    720

gagaaaccac tggacactcg gacgactttt tgtcaatcat cttctcgcct tccat         775
```

<210> SEQ ID NO 5
<211> LENGTH: 1113
<212> TYPE: DNA
<213> ORGANISM: Pseudoperonospora cubensis

<400> SEQUENCE: 5

```
atgaaggaca tcacacgtat taatgatacc cactcgaagc tttgcgcaca tcagaaagat     60

gagacgttga cgtgagctca tggctggaaa aatccgtacc ctatagagac ggaggcgtgg    120

ctagcagacc gtggagttca tgagctcatt gagatcggaa gacgactacg agctcgacta    180

tcgacgtcgc cagtgcattt tgactctagc aagtttgtgt tcgaacacac gtggaagatc    240

cgcacacgtc agagtgctga ggcctttgcg ttcgggttct ttgatggact tcagcctgtg    300

tactaccata gctatccgat cggagatgac cacgtgttgc ggttctatga caattgtccg    360

acattcgaga tgcagattga caagaacaag agtgctacta ttgagcacat gaaatatcgc    420

gatagtgagc aaatgcacaa gaacctggcg acattccaga agctgtcgaa gtttccggac    480

gcgactcaaa aggatatgga ggcagcgtat gctgcttgtg cctttgatgt ggctgtgctc    540

aatgtgtttg acaagtggtg ttcgtttttt aatgacgaaa tgctgctgtc tatggactac    600

tttcaagacc tcaagcactt ttacagaaag agtcatggtc atgcgctgtc gtacaaaatt    660

gcgacgccac tcttacagga tatgttccgc acgatgaagc agcgtgtgga tggcaagacc    720

aatgtggaag gatatttccg ctttgcacat gccgagacga ttctaccgct gacatcgctc    780

ttgaatgtta gctactttga tcggcacgct agcgatcgcg agggccactt tcgcgctaac    840

acgccgctca atgtagcatt gcagcgaaag ttcaagagct ctgagctggc cccattttcg    900

gccaacgttg gttttgtact ctacgagtgc acagcggagg aaggacaagg tcacgcgagg    960

ccgacattca aggtgaagac attgcttaac gagcatgagg tgagattcaa cgagtgtaag   1020

gaccaagcgc tctgtccatt tgacgtgttg gagaacattt tccggagttg gatatacgag   1080

tttgattttt acaagcattg tgcactcgat taa                                1113
```

<210> SEQ ID NO 6
<211> LENGTH: 729
<212> TYPE: DNA
<213> ORGANISM: Pseudoperonospora cubensis

<400> SEQUENCE: 6
atgaaccttt ggtcgatatt cgtcgtttcc gccgctgcca tcagattcat cgatgctgaa 60
agtctccctc cagaccaaat ttttagtttc aacgaggtcc caccagtcac gggtattgat 120
aattcaacac tccgtttcag accagctctt ctgatcacca ctggatgtca tccctttgcg 180
gccgtcgatt ctagagggcg cacgagtgcc ggacttgagc caaccgggaa gatgaacgaa 240
ggctgcgggc ggtcagttat gacatctcaa gtgtatgccc gagccaagtg gcacggggat 300
ctgtggggca tcctgtacgc atggtatttt cccaaagaca tgcagagcga tgatggaggt 360
ggacaaaagc acgattgggc gagttgtgtt gtttggatca acaatccaga agtcccgatt 420
ccggaaaagg tcgctgtgtc tacttcaaca tatgtcgaca gatacaagat atacaagccc 480
cctccatacg aatctgcagt cggcgccgtc acgtgggtcg tgtactatca agatcctgag 540
aaccataact atcacactgt ggacataacg gctgacattt caggcaactt tgatacgctc 600
atctcgtggg accatttgac taaagaggcg actgcggctc tcaacaccgt agactttggt 660
cctcatgcca aggttccgtt caacgatgca aacttcgatg ataatctcgc caaagcgtac 720
ccgaattga 729

<210> SEQ ID NO 7
<211> LENGTH: 549
<212> TYPE: DNA
<213> ORGANISM: Pseudoperonospora cubensis

<400> SEQUENCE: 7
ttagcacccg ccaacagagt tggtgaaaag cgaccaaacc aacgcaagca tgcagtatgt 60
gatggtcatt ccacccagga gcttgccccg ttgggcattt cgcttcagta ctcgagtctc 120
ctctttttgt cttggaagca ggagaagaaa cagcagcgag agtagcttgc aggtgtagac 180
aatgagcaca atggtagtga cattctggcg tgtggcatgt gaatcattca agacatccca 240
gttgcgaaca ggaaaaggtt ggttgatagt catagtgaga gttgcccaaa atggattgct 300
gaggttgccg accgtcgtca aaagtccata gatggcggct tcattgccct tgttggtcaa 360
ttccacaacg acaaagctcg aaacgataaa gttcattttt gatggaatgg tctccacaaa 420
aagcaagcct agccagaacc actagttacg cacgacagtc cacgtggtga acattgtata 480
cacttccgat cccgccacga tgtattgggc ccgcgccacg aacgtcagca tatcgacctc 540
gcagatcat 549

<210> SEQ ID NO 8
<211> LENGTH: 860
<212> TYPE: DNA
<213> ORGANISM: Pseudoperonospora cubensis

<400> SEQUENCE: 8
cagtaatgca acgttggatt tctccgttga cctgccatca ttctcgatcc cagaattgcc 60
actgactcct tgcaaagcct agagtaggtc ttgaacgctt cggacacgca gcgaccgtaa 120
aactgaactg tgagggcatc tgcacgtgct tggtacatat gcgtcgctcc accggcgcgt 180
aaagagtgct tactgaagca tcgcagacca tgacctgtgc taatagccgc ccgcttgata 240

```
gcttctgtta cgcagcttct acaatacaga ccagtttccc gcagtgatct aggcatacag    300

cagtcggtat gtcgatggac aagcttttac gagcttgttg aaggatgaag gcgccacaac    360

cgggcgaaga tatgggtacc cagagtgcga cagcattcgt gctgtaggag atccgccttg    420

attggccttg gggccagtca gccacaagta cacgtaatat gcttttgaag agaacaaagt    480

tggttggcct ttcgaataca atgctgcaat gttttgagct tgaacggcaa atcatttaaa    540

ggagctccct gaaattgcta ctattttcga tcgtctgagc ccgaaaaaga acgccataca    600

catgactccc acaaagcttc ctcaaagggt tcagttgtcg cgaggatgta gtcacacacc    660

tcaagaatct cgctcgatgc tggagcgttc cggcgtgatg gcgagtcgag gcggcaattc    720

tcttgagtag catacgcata ggcgggtgtg cacttgaaaa gtcatagcct gaagccgaga    780

gaaagtgctg aatgccgagg agaattgcca tgttgaaatc gctacgaatg ggttcgtcgt    840

acccaaagcc atgctggaag                                                 860
```

```
<210> SEQ ID NO 9
<211> LENGTH: 995
<212> TYPE: DNA
<213> ORGANISM: Pseudoperonospora cubensis

<400> SEQUENCE: 9

ttaatccttc gtgaatgcca cgtgccatgc cttaccataa gtgccgtact gactaacact     60

cactaccact gtatcaggtg cggtaatcga ctcgacagca gcactcatta tagctgcatt    120

tgttccttgg aatgatggcg gtgtagccac ttctcccata tacgacacga tgaaggtgcc    180

tccatctgta cttgatgcat ctgcgaggac agtttggatc ccagagcgac attaggagca    240

cgcacctaca tcttgacaga atgaacttgg ccgaagagca gtaagcttgc aggcgcccag    300

gcagcacagg tactacctgt tccaaaattt gctgagtcaa actgtagcgt gggccactca    360

ccgactggat aatggcccca aaagcgcaca ttgtagtcat ggaagtccaa aatcttcaag    420

gatcgagctt caccagaaaa tctatcgcag tatccatcag aagtcacaga aagctgcgtg    480

gcacccacgg ctggggaagc gttgacaaca aactcacaag aatgccgaga aaagtcgttg    540

gggttccgac tcacccgaat gatggtatct ttgagaagaa ccgcaacttc gtcagcagtg    600

agaccgccat gtggcatcac cgtggaatcc gtgctgacga cagtaaggag cttggaagtg    660

ctgtcgtagc ctgcgacttc tgctgtggct gaaccggcta gcacaattat cttaaatgca    720

cgcacccatt tgaccgccac tttggacacg aagtcgagag tttccagttt cttcttcgta    780

ttgcttgctg tgtcttgttt ccttaacgta atgcagtcag ttaatgcatt tcccagtttc    840

agcttgaagg tccccgccgt agctgtcgtc tggccaaaca attgaatcac ttgagccgaa    900

gacgggactt caagagtatg agtatcacac acgcgtttgt cattattgat ctcaaagtag    960

ccgtagtgct cagacgggat agcagcttgg tccgc                               995
```

```
<210> SEQ ID NO 10
<211> LENGTH: 707
<212> TYPE: DNA
<213> ORGANISM: Pseudoperonospora cubensis

<400> SEQUENCE: 10

atgtacatgt ggtacgtgca ttcacatcaa tttgtcatcc tacaagttca aaaatacttc     60

acggtaacga ttttttggtc gccaactctc caacttgacc acgaatttcc accatcatct    120

gctcgatggg gattactcag cgcttgcaac ggtcaggtag acgcttcgtt cacaagtggg    180

aatcagttca agtcgagctg cagggtcatt actccattga gcgcttcaca gccttgacgg    240
```

```
agttcagcca aacaacgagc ttctaccgtg cgctagcaat tctccctttc acgatattac    300

caagcctcat tctggtcgca ttggttgatg tcattcctct tgaagctcct gaaagagggt    360

taaagcacag cgctttggcg tgggtccgag ccactttagt atgcttcatt tacacgcatg    420

gcgcaatcga gcaaattcgg ctatacagtc cgagtctcaa gctggaacca atgactgcat    480

tttacgtttc acttcccgca gcgatactca cgaatgcact tgcattgctc ttgtcagttt    540

ttgtgtgctg gccactacca tttgctacca ttttgatgtc gggcccgtgg cttggcttca    600

cgaccttgtt tttactactg actcgtggag cgcatctgcg cgcaaacccc gaagctgtga    660

aagaagtcgt tcgctttgcg gtcatttgcg gagctcagct tacgatg                  707
```

<210> SEQ ID NO 11
<211> LENGTH: 248
<212> TYPE: DNA
<213> ORGANISM: Pseudoperonospora cubensis

<400> SEQUENCE: 11

```
ttaagtttct ttcgttggtt gggagccagg aacattcgta tatacatcaa ccgaaatatt     60

ttgtccttgc agtgaagagc gtatcaccag caataaaccg acattgccac tgccagacgg    120

gagtgtaaaa ccttcgaaat ctcccgcatt ctgcatgaat cggagtattt agcgatctcc    180

ctctcgcgta cctggatttc aaactggtat gtcactccag cctcctgctc acgatgaatc    240

cccacaac                                                             248
```

<210> SEQ ID NO 12
<211> LENGTH: 1694
<212> TYPE: DNA
<213> ORGANISM: Pseudoperonospora cubensis

<400> SEQUENCE: 12

```
atggcgttgg cacttcaacg cggctggatg cagcaaggta cgcttcgact cacatcacac     60

ggtgatcgta catgtttaac gcttgctgac tttggccatt tgaatgctac agtatcgtgc    120

aaggttcgtg caccgaagtg gcgtcgattc tcccatgtgg cagacgctca cagccatgcg    180

gagcgtacgt cgattacgca agaggtgcgt ccggctgcac gctctccttg aaacgaaaga    240

gaacagactg atgctgagaa cgtgcagctt ctaggggtgg acgtgcatca gcgcgagatc    300

attacgttgc gatggcaaga tggaaagcgg agtaagttcc actgcctgca cctgcgtaca    360

tggtgccagt gtccggcatg cggccatcca acgggacagc gagtagtgaa ttgctccgat    420

atcaatcaag acgaactaga catcgaggaa gtgtttggta cgttgtgttc tgttgatggc    480

actggcatgg tttgtccctc gcctcaaatt gtgttaagca gaatgttgtt gatctgctgt    540

tgcgcagtga agggagacac gctgaatatc gtgtggaacg accaccacga atccatcttc    600

tcgtgcaagt ggctgcttga aaatagctac tcagactggg cactagatca acacgctcat    660

gacgtgacta cgactccatt agcccttaat gctcctgttc cctcgacgga atacgagcga    720

atgatggata cgagcgatga caaggggctg tttgaggcac ttcaccaggt tgttgaatac    780

ggcttcacgg taatccgcaa tacaccgtca gtagcaggcg ctgtcaagac gctcgcggag    840

cgtatttcac ccatctcgca ctcgtacgac gttgaagtga agttgaggct gacattgata    900

ccgagttgac ccgattttca attacatttg cgcaggttcc agtatgacga ggtcttcgac    960

gtagtggcgg aacccaaacc tgtaagcaga ttctgacgca gatagattgg tgtcaatgat   1020

ggaagctgat atgaagttgt cactcatctt ctgtctaggt caatatcgcg tacactacta   1080
```

-continued

```
tgtacttgaa gagccacgtg gatctggcat actatgagtc tcctcctggg tttcagttct   1140

tgcatgctct gcgctttgac gaatcggtcg aaggcggtga gtcaactttt gtggacgtgt   1200

ttgccgtgac tgacgagttc cgtcgccttc atccggaaca ctttgctacg ttctgtcgtg   1260

tgcccgcgac attcaagaag caccatctga ctcgtgagaa ggccacaatc atggagtacc   1320

agcgtcccca catccagctc aatcaccgtg atgaggtggt tgctgtgcac tggagtcctc   1380

cgttcgaggg accactgaaa gttccatttg gcgacgtgat gccatactac gatgcgtatc   1440

gcatcttcca cgaactggtt gaaggtggca agcatcgcta cgaattccga ctgaaacaag   1500

gcgacactgt catattcaac cagcgccgag ttttgcatgg aagaaagcag ttcacgccga   1560

attccgatgg tgtgcgtcac ctccagggca cttatgtcaa catcgacgac gcgctttgtc   1620

gctacaacgt gctgcacaca cgcttcggca cggacacgaa aactcgccgc gtcgccaacg   1680

gcagcttctc atag                                                     1694
```

<210> SEQ ID NO 13
<211> LENGTH: 216
<212> TYPE: DNA
<213> ORGANISM: Pseudoperonospora cubensis

<400> SEQUENCE: 13

```
ttagttactg ctggtactgt tgccgcacgt acattcggcc accgtgagta ccacatccat     60

ggacgcgagt cctgacttgt acagggcgca gacacccgtg gggctggtca aacagttgcg    120

cccccgctgg aactcccaaa agttttggag taggcacagg tccttgcact tggtggcgcg    180

ctcatcgggc ttggagtccc atggcgtggc cttcat                              216
```

<210> SEQ ID NO 14
<211> LENGTH: 282
<212> TYPE: DNA
<213> ORGANISM: Pseudoperonospora cubensis

<400> SEQUENCE: 14

```
cgccaagcgg tcgtacgctt tgttccggac gccatcgcag cagatgcggg caagcagaaa     60

gatccagccg acaagagtga aagggcaaac agatttttat tcagtggggg tgacttggtg    120

ttgctcggta cagctactct acctgcacat gaagtgacca accgcagcag caacaagtac    180

atgtcgaggt atgctggtcc tttcaaatca tggaaagttg cagcatcgaa tacaagctgt    240

agcagctgcc gaggatgcga acgcatccta cgtatttttt ga                       282
```

<210> SEQ ID NO 15
<211> LENGTH: 427
<212> TYPE: DNA
<213> ORGANISM: Pseudoperonospora cubensis

<400> SEQUENCE: 15

```
atgaatattg gaagacaatc tcaggtgtgt agtctcacac tatggtgatg actaggcgaa     60

gatcttgccc acagtgtagt acgcgcattt gacgttgatt tcaacgtcgg ccaaggtctc    120

gccatttaaa gtcaactgtg gtcgcaagcc ccgttccctc atcacgcttc aactggcaga    180

acgcacggcc agcttggcag agaatttcac cagttcgcgt caagaggtca atgcttctgc    240

ccagcgcaat tttcggttag atcaagagcg acaggccaag tactacaacc ttgggcaacg    300

agcaatcaag tttgacgtcg gtgacttggt ccacatcgat gctcgtgtgc tcagcagtga    360

gctcggtcaa cctgactatg accaaagcaa agaccctgtg tgcaacaagc tactgccgca    420

atggtag                                                              427
```

-continued

<210> SEQ ID NO 16
<211> LENGTH: 571
<212> TYPE: DNA
<213> ORGANISM: Pseudoperonospora cubensis

<400> SEQUENCE: 16
atggcggtgc caacctgtgg gcagctcttc tttcccgcta gaggcttcct tcgttaggag 60
gtgagggtgt gagcatccag tgcaagtaca tcgtcagaag cggtggcaag gctttgctag 120
ggaatgaaca gacgagcgag gaggtgaccg acgcgtcgac cgagcgcagc caggaacatt 180
aaccgtacgt gagactgcgt gcagaatttt tgttttctca tcgcttgact caatccatgt 240
cgaacaagca aagtaccatg acaagcgcct cgaaaacgcg cgtgtgaaca gcagtggact 300
aatcatggtc aaccagcaca tctgggtgcc aaacgacgcc gtagatctcc tccaacgcat 360
ttccgtcgta gcccactgcg aaaaccaaag gcaccgcgga cttggatctg tggcgacgac 420
cctgaacgac attttcagca tccatgacgt tgagtccaag tgcagaaggt tcctcagtca 480
ctgtttgttg tacaagcaca tcaaaagcgt caacgcgatc ccgcagagac ccacgtacga 540
cgcaacccag cataacaagc tgttgcactg a 571

<210> SEQ ID NO 17
<211> LENGTH: 565
<212> TYPE: DNA
<213> ORGANISM: Pseudoperonospora cubensis

<400> SEQUENCE: 17
atgggcgata gcgttggcat ctgtaaatat gtgctggtac tcaaggacaa cttggtcatt 60
actgcgagcg ggtggcgtgc gacgtcacga cgagcggtcg cagcggaagc gctcctagac 120
tagttcaaga gatttggctt acacgcgatg catatctccg atcagggcat ccattttagg 180
aacgacgtca tagatcaagt ctgtaagcat ctgtcgatca aataagagct tgtcgttgcg 240
tattcgcctt ggaccaacga cacattgggc gcttgaatcg cgacgtgctc caaaccgcgc 300
gagctctgct cctggagcac gagttagaca cgcgagagta gccatacgtg ctacccgttg 360
tcccggcaaa tataaatcgc actacagtgc agtcattggt caacaagtag ccgacaaagt 420
tgctcactgc attgccccgg tcgtcgcctt tcgagtcgat ctaggtggag tgcaacgaca 480
gacccttatt ggtggtggcc gaaactggtc tgcccgaaga gatggtcgag aagatacgtg 540
gcagtctggc cgcgatgcac cgtga 565

<210> SEQ ID NO 18
<211> LENGTH: 408
<212> TYPE: DNA
<213> ORGANISM: Pseudoperonospora cubensis

<400> SEQUENCE: 18
atgggtgggc ccgttcgagg tagaagatac tcgagcgcac tccttcatta cccgacactt 60
catcactaaa gaggactaca aggtgcacgg ctgcaggctg aagctctata gtgacgcgag 120
cctggacgtg aacaaggagc tgctgaccca cgtggaaaat caaggcatgg tgttgggcgg 180
caaggatatc gaagccatcg ccaagaacgt ggtgtgtggc aaatcctggt ctcgtgggtc 240
gagcatcaga atgaagaaga ctcgtgggag gcgttgcgtc acatggtcgc caaaatacct 300
gttcgcgtcg cggactacgt gctcgaggcc agcgacgcag gcttcacggc aacaaggact 360
agcacaacat caggaacatg tacgcagact ctggctcgta caactgca 408

<210> SEQ ID NO 19
<211> LENGTH: 303
<212> TYPE: DNA
<213> ORGANISM: Pseudoperonospora cubensis

<400> SEQUENCE: 19
ctactgccga aatggtacgg accgtttccc gccgaagagc gtattggcca gaatgtgtat 60
cgtgtgtagc tcccgcacca aaacgttgcc cgtggtcgcc acgcgacttt caacgtgaac 120
cagttgaagc cttcgcttga tgtgccagaa atgttccacg gccgccagat cacgaaaagt 180
gctccacgac tttctgacga caacaataaa cgcgtgtacg tgctcaagca cttgctacgt 240
aagtgccagc gccacggcca gacccattat ctctgctcct gggttgacct tcccgagacc 300
tag 303

<210> SEQ ID NO 20
<211> LENGTH: 345
<212> TYPE: DNA
<213> ORGANISM: Pseudoperonospora cubensis

<400> SEQUENCE: 20
atgagtccaa atcacgactt cagtcacaag gttgagcctt ttggcggctc caggtacatg 60
ctatggacct tcaaaatgag catgcaccta gcgtcgaacg gattgccgga ggcgatcacc 120
ggcaaagata cagtttcgca aaccaagaag cagcaagcag acgcagcagt caccctcaac 180
ctcagcgact cggagttgtc accacgtcgt gcacaagaga gacatggctc atgtttgaaa 240
aattcaccgc actcaagaca tggtcaatcg gctttggctc aaggagaagt ccgcgttatt 300
caagtacacg gcgtcaaaca tcagcggtca agtactgaag cttga 345

<210> SEQ ID NO 21
<211> LENGTH: 530
<212> TYPE: DNA
<213> ORGANISM: Pseudoperonospora cubensis

<400> SEQUENCE: 21
tcaaattact tcatccgtcg tcacgctact caaattcgcg cttggtgacg aactcaggga 60
tattttcatg ttcacccaat ccatgcgtgg ttggagcagc ttcagccact gcatacccag 120
aatcaggttg aacttctcgt cgaggtcaag tagaatacac tcgtcgtcac ctcaaaaatg 180
cccacttttc atcttggtct cttcaccatt tggactggtg cgtcatttgc taggcaaaca 240
ctcatccccg tcttcgagtc agacacgctg atgccatgat tgcttacaac acgctcacgt 300
acacagctgt tcaaagtttc agtgtcaatc agagcacgta gaggctcctc aaaacctttc 360
gcggagacct tgatcacgat caaagctgag ctctgactgc ttctgatctc actcattgtg 420
gaaactgcat gcgcattcag cacacatgta cacgccttca gtgtatccac tttcctagta 480
agaagaccgt gcttcggttt cggcacagcc aatattttgg aatcctttaa 530

<210> SEQ ID NO 22
<211> LENGTH: 509
<212> TYPE: DNA
<213> ORGANISM: Pseudoperonospora cubensis

<400> SEQUENCE: 22
tagtgttgtt cgttgaagac agagcagcaa tgtcgttctc ttctgagtgt catagtcggg 60
gcaggagtga ccggcgctgg cgtcgctggg caattctgcg acttcttcag aagaatgctc 120
acatctgcag accttagccc cagtcgggtc actgtgtcgg aggtagactt ctccttcggc 180

```
aaccacagaa aatcggggtg cacagagagt gattcgtaca gctactcgtc accagtgatt    240

ttgccaacag catcaagttc tggtagtcag cactactcat gtacccatcg gcatgtctgc    300

gggagctatc ttccatctcg aggatccacg atagacgcgc ctttacgtac acattgcttt    360

ccgcagcagc attctacgga tatttctcga gagcgtagaa ggtctgagca gcctccgtca    420

aagacatctc agtctgctcg ttcaccttga aaccgcgcac atggcctgag tgggtaaatc    480

tgtaaaaatt gtctccgtct tggtggccc                                      509


<210> SEQ ID NO 23
<211> LENGTH: 342
<212> TYPE: DNA
<213> ORGANISM: Pseudoperonospora cubensis

<400> SEQUENCE: 23

acagcgtgtt tgaagagggc gtccagatca atggcctgaa gggcatcgaa tactttgaca     60

cctttgctgg tgcatacatg acggagacga gcgacaacgt tgtcattacc gagcagactg    120

aacatatata cataaactct tctgatgtgg tgcgtttcgt catccgtacc aacaacggtg    180

ctcaacaacc gaacgaccca gctcctaccg gcaagcctgt gaaccgcact gtgacgatta    240

ccaagtatgg tgtcatcagt ggcagctctc ctaagtccac gccaaccgac ttcgcagtgt    300

ggaacccgtg ggctgagggt gccgcactca ttggggactt tg                       342


<210> SEQ ID NO 24
<211> LENGTH: 348
<212> TYPE: DNA
<213> ORGANISM: Pseudoperonospora cubensis

<400> SEQUENCE: 24

atgatccgcc tgcttgaaaa aaaggggctt cgatacgcag ttcacacaat tgatccggct     60

gctctacacg aaactcaagc gcatctagtc atcatccaat tcattcaacc tatgctgtac    120

ccaacccgag gcgtgaagca aggcgatccg ttgtttgtgc ttctattcat attgaccttc    180

gatttttctg gcaaccagct tcggtcgcac gatgagtatg gcgtgcgtct gaatgcagac    240

cacaacacca cgagcacatt ctatgcagat gacttcacct ctgccgcgaa tacgctgaca    300

acaataccgc tagacaacgc gtggggactc ccaagcccca gcttgtga                 348


<210> SEQ ID NO 25
<211> LENGTH: 329
<212> TYPE: DNA
<213> ORGANISM: Pseudoperonospora cubensis

<400> SEQUENCE: 25

ccaaagtcag cgagcttgta ctgctcacca ttcatcagaa tgttcttggg cttgatgtcg     60

cgatggcaaa tgtgattgca atgcactaag tagcgaaaca catagtcaag tcagcacaag    120

ctacaagtca ttgaggacaa gaagagcaag ggtactcaca gaaatgaagt gcatctacga    180

caccacgcaa gcactcgcgc acggcatctt tgcttaaaac ccctcctgaa gcatcacggg    240

ctgtatagcg aaacgttata tcgtcccagt acatgatctg acctccgtta accagctcaa    300

gtaccaaaaa gagtttatcg tcggccgga                                      329


<210> SEQ ID NO 26
<211> LENGTH: 1265
<212> TYPE: DNA
<213> ORGANISM: Pseudoperonospora cubensis
```

<400> SEQUENCE: 26
atgctatttt gcgacttgaa gtgctttgcc gttctgagtc caatggaatg ggcactattc 60
gcgactttct gcgctattgt tacgtgtgtc gtaattttca ccacagaaga acttgcttgc 120
aatgctggat catactttgg tggcgttgag agctcgcact gtccagaagg cacgttcggt 180
gttctaccag gatcgatatc tccgtcgtgc tcccggttgt gctccgccag atttttctgt 240
ccggaggaat ctgctgcgtc ttgagcaaaa tcttgcggtt cttctatctt ctattgtccg 300
atatgaagtg ccgatcgtct tcgtgtagac gcgggatact acacatttcc ggcagatcaa 360
agcataactg acacgaccag aggtggtgct ggacagcaaa tttgtagcaa gaaaggatac 420
tactgcgtct ttggggttcg atgagcttgc cctgctggag tgttcagaga ctcgacgaga 480
attactacct cacagtgctc agcaccatgc tcaaagggat cgtactgccc tgagaccaca 540
tttgtaccga ctctgtgtcc tgctgagacc tttggggaca aattcggtct aacaaacgat 600
cgatgcagcg gcctctgtcc tatcgaccac tactggtaca tagttctatg ccaccttaag 660
cttatctgta atccttcttg tagtcaagct gggacgatca ctgccctcca gggacgtatg 720
gaagtacaca gggtctcatg tgcttgagta tgtgctcgct ggtcgatggt gtgttcacgt 780
gtataccttc attttgccca gcaggatgtt actgtccact tggagcagca gtgccgctag 840
agtgtggagc tgttggcgcc ttttgctttg aaggttcttc gagctagtgc tggttattat 900
accatttgaa aagtgaatac tgggacatct atgacaaacg agcagttcgc actgaacttg 960
tctgtccata cagcaataaa tcttgagcaa acgtttgcac atatgtgctt gcagtccgat 1020
tgaaactgca ggctacacat gtgtacatca ttttgtcacc aaggctcacc cgaaccagtc 1080
aatactttag tgtagtaact caggcaggcc ttcgccctaa tgaaacaatc tgcccgtcgg 1140
tagtttttgc atcgaatctt gctcaggaaa ctgtgcccaa gaggctatac ctctgtcaaa 1200
caatcaccgt gtccaacggg atcgtactca cagaatggtc tattctgttc accttgttct 1260
tctga 1265

<210> SEQ ID NO 27
<211> LENGTH: 959
<212> TYPE: DNA
<213> ORGANISM: Pseudoperonospora cubensis

<400> SEQUENCE: 27
ttagttgcgc gtgcgctttg tctttctcga cacagttctg agcccatcgt taagctcgtt 60
ggttagcaag agaggttttt tcagagcttt gggtctagtg agaagagtga tcttgatatt 120
cgagcagttg gacgtcaaga tcaagaaagc gccactgcaa tcagctatta gcttggtgag 180
gtaggtaaca gcaagatgct gtccatagaa accttttcgt tggagctgga cttcaacttt 240
cttactttct tgacggcctt ctacagtaag atttgcttgc gcataaacat cgtacttttg 300
acacgcgcgt acctcgccgg acgctgatgt tgctgcacag aagctgagac tggtttgatt 360
tggaggagca aacgcacact tacatataac gagatcgaga ttgagaccgc gatgcgagcg 420
atagtcaaat gacagtctcc taggctggtg cagtgtgttc taaccatgcg cggaaagaag 480
gttgctgtcg aaaagcactt gaatagcaaa cggagtcgtt gatcatcaat gtattagtaa 540
cagattttga aataatgtac atgcgccatg ttgcagacgt gagtcccttc gcgaggttca 600
cttcacggaa cttgtcgtac acggtcatac atccaagcag gaacaattgt ttcaggacaa 660
gatctttata cgtgtcggag tcgacgttaa gatgataatg aagtactatg cactctggac 720
gccgaattcc ttgaacctga agacgccacc aaagaggtgc acttaagcat aacacacatg 780
tctttcgact tgactttgac gcgtagattg tcaccgggga gattgaagac ttgaacgatc 840
ttattggtct tgtatagacg ctcgaggata tcactagcat tgtttttgcc gcatcgcgac 900
atcatgacct tttgaagtgg ataatagaga cagtatgtcc ggtatgtcat atctggcat 959

<210> SEQ ID NO 28
<211> LENGTH: 275
<212> TYPE: DNA
<213> ORGANISM: Pseudoperonospora cubensis

<400> SEQUENCE: 28
atgagctgct ggccaacgtg gaaaatcaag gcatggtgtt gggcgtcgaa agcaccaaag 60
gtcatcgtca agagcgtggt gcgtagcagg ctctgatctc gtgggtcgga cttcaggatg 120
aaaaagactc gtgggaggcg ctgcgtgaca tgctcaccga gatacctgtt cgcgtcgcgg 180
actacgtgct tgagggcaac gtcgcaggct tcacagcagc atacaatcgc gagaaacgcc 240
aagccaacaa ggttaagcat aacaacatgc aatga 275

<210> SEQ ID NO 29
<211> LENGTH: 261
<212> TYPE: DNA
<213> ORGANISM: Pseudoperonospora cubensis

<400> SEQUENCE: 29
atgtttcttg gatatgccga gaatgcgaaa gggtattgtg tgttcgacat gaaaagctcc 60
aaggtcaaag tggtgcaatc tatacgactc gatgagcgtg aagtggacgg catatactct 120
acggatccac cacagcatat cacggtgact catgtaatca aggaaggtga tgaatttgtc 180
aaggttgatg agcgtacgca agatgcagcg aaaatgccta tgaaaggcat tgagaatcat 240
gccccggacg tagagatgaa c 261

<210> SEQ ID NO 30
<211> LENGTH: 730
<212> TYPE: DNA
<213> ORGANISM: Pseudoperonospora cubensis

<400> SEQUENCE: 30
atgggatgca ggttgttact gcggtctccc agcaaggaat ttacgaagac cgaggatcag 60
ctttctaaat tgcgatccga cacgaagcac gccgtagtga actacaccgc gacggatagt 120
gctggaagct tgcgcgtctg gcatgaccga cttgcccacg tcaatgctca gtatctgaag 180
cttacaatca accgtggtat ggtgaagggc atgatgatcg ctcagcgcca gaaaacacta 240
tgcgacgttt gtgatatcga gaagcagaag caaaagacgc accatgaaac actgggcaga 300
ggcgtgaccg cgccgaacca gatcatcttt gtagatctac tgctcccagg tctgcacaac 360
gatatgagat acgctgcgat cctcgtcatc atcgacggat ggatgaagct ccttacaatg 420
catttgctca aggacaaagc cagtgacgac gtcaatatgc gcagatgaaa gcgtacattg 480
tgtggactga acgccaggct gggcgcacat caaaaagact tttgagaatg acactgaacc 540
aacagagcaa gctcgatctg ctgtaaagca agtgctcact gacaaagaaa gcgagtttgt 600
gaatagtgag gtgactagct ggtactgcaa accggagatt gaacacttgc aagtgatttc 660
gaaaagcttg catctaaatc agtgtgagcg agcacaacag tcgcttttta aaatagtcaa 720
gactctatga 730

<210> SEQ ID NO 31

<211> LENGTH: 192
<212> TYPE: DNA
<213> ORGANISM: Pseudoperonospora cubensis

<400> SEQUENCE: 31
tcagtttctg cgcttgctct tccattgttg gcctatgact atgaccgtgg tcgtatcact 60
acccacagcg tgcatctcag cgcgcgtggc cgccgtgaga aagtcctgaa tgctttcgcc 120
ctcttctagc ttgggcttgt cgagcaagtg gtccaacgtg tagatcacca cattcggcac 180
gacgtcaaca cg 192

<210> SEQ ID NO 32
<211> LENGTH: 741
<212> TYPE: DNA
<213> ORGANISM: Pseudoperonospora cubensis

<400> SEQUENCE: 32
acttcttgaa aaaccgattg agtgccgtag gtgcgctctc agccttttcg ttccactcgc 60
gctgctgctc ctgtcgatct tcgcgtttcc gcttgttggc caactgctca cggagctgtt 120
gcttttgtgc atcaactacg ttctgctgct ttttgcgcag tcgccgtgac ggacgatttt 180
taccgcgcat tttcttcttg ggcttcttgg cattaccctc gccattggca cgctgcatct 240
ggtgaatttt tcgttcctgt tcctcggctg ggtccatgtc cacacgaccg atagcattcg 300
ggtccaatgt gatcatctcc ggacggatct tttccagcag tgagcgcacc tcggattcat 360
cacgctgttt gtggttctcg tacgggtttg cttcgtacgt atcaaagttg ggctcaccag 420
cgccaggaat taccaccgag ttaaagcccg tggcatggcc gacacccagc acatcttcaa 480
acgggcgaaa tgcaagtgag ctgactaatg aacctggaat ttggtacgtc atgtatggtc 540
tgatgggaga ggacgacgag aaagcgccct tgagcacgtg cacatttggg ccgaagccta 600
ttgccacaag tccacgttga ctcacgctca tagtattagc tgctgctgtc aggtagtagc 660
tgttcagctc ttggtatttg cgcaggtcga acacttttac ttttcgtgga tgacccgctt 720
cttcatgtac cttgaccgtt a 741

<210> SEQ ID NO 33
<211> LENGTH: 431
<212> TYPE: DNA
<213> ORGANISM: Pseudoperonospora cubensis

<400> SEQUENCE: 33
ctactctctg aatgccatgc atagcactaa cagattgacc atgttgatgg cggcgctcac 60
gtctcggtcc cagtacttgg cagtgcaatc tgtgtggtcg ctgtagagca cctggtagcg 120
ctgcttctct tcaagctgga cctcagctcg gttgccataa cgcctttgca ctttctccgc 180
ttcgtgtcga gtgtgtacct gacggtcgaa agcgcctggt ggcactgcac gcagagctta 240
ctcgtcacga aatcgtcaat gaacaacacc gccgtacgct tccgcaacgc atcagccaac 300
cctttcaccc gaatggatgc gtgtcctgtg atgccatcgc gtttacttca gtccccttat 360
gccacgcacg tcttcgtgct tgccgtcgga acaatgcgct ttgtgattct atcgaccgtc 420
acacaagcca t 431

<210> SEQ ID NO 34
<211> LENGTH: 339
<212> TYPE: DNA
<213> ORGANISM: Pseudoperonospora cubensis

<400> SEQUENCE: 34
ctagtatcca agtatccgaa tgatgccctg ggcatgagtg ttgcgcgatc caaggcagtt 60
ctggaagacc accgccgaag tgctgtcaat gcaaaagcga gtgtgcagca ggctatacat 120
gtaagtagtg gccaggcacc agcgtgctcc tcgtttgtac gtgaaaaaag cacacgaaag 180
taattctcga taattgattg caaaaccgct gacttctcca ttcttaaagc gatcaataag 240
tcgaagctcc tggggcgaga atcgatacgt cagtgcaaac ctggccgtca catcgagagc 300
acacaaaccg cggtcacaag cactcatttt cacaaccat 339

<210> SEQ ID NO 35
<211> LENGTH: 969
<212> TYPE: DNA
<213> ORGANISM: Pseudoperonospora cubensis

<400> SEQUENCE: 35
tcagagcgag tgcagactaa agctcttcga ctctttcctg ttcttgagtg tggccttctt 60
gatagcacta cataaatgcg cagttgaaat acttgctggc tgccctgtgc gcaataaata 120
aactgctgct gggatgtcaa agcaggtctg acctcgctcg taatagaagc aaagcgccga 180
atacagggca gtcaaattat gtacggagcg atgcagcgct cgggccgttg catgtccaca 240
ctggtttatc tttgaaccgc aaagccttac atgcactcgt aggtgatagt gctagattcc 300
tagtcttgtt agggacgact aggtccttgg ccttaagtgc aatccgtttg aacgtacttt 360
cgctaataga gacgattatc gaacgtcgaa gcaggaaaaa gaacgccaca cacacaaccc 420
ctagagcgcc tggtcaaagg ggccttcaaa gcgaaggaaa cgaaagtgtg gtgagctggg 480
gtttcaaaac agcgttatga aacctcaaaa cactcactgt gccggactgc cgacttacgt 540
gggggcaggt accccgatgg cgcgtataaa ctaggactca ccttgtgtac ccgtcagctg 600
gcggattgca ttcttcggta gatgcgtgtg agaaagtcaa tgcttgagtc ttgatagata 660
gacctagggc ctcgagtata tttgtgggca agtgggagac cactcgatcg atccggtcga 720
gagtggactt ataccagtgt atcgagctcc ctgacttttt ccttaccgtg aggcgctagc 780
cgcctatctt ttgctgagtt tcctgatcac gaggtaggga gattgacaac ggagttttcg 840
cggaggtatt acaccagatc aatgagagat ggtccacgtt gacagctgac gacacctgca 900
tccaatcacg agcgagtgca gcaagctgcg tagcgtaagc caggtgagcg gcaatgtgca 960
agccagcat 969

<210> SEQ ID NO 36
<211> LENGTH: 438
<212> TYPE: DNA
<213> ORGANISM: Pseudoperonospora cubensis

<400> SEQUENCE: 36
ctaaataacc caagctgggc aattccatgg cgctcggcta gaaggcttta aattggttga 60
gccaagtcga aaggttaatc caatatggtc ccctataccg gatttggctt gaaagtcatg 120
aaaaatgtgc cgaaacagag agtgaaataa ttgatagtct acgaaggcat aatcgatact 180
agacgatcca gttggacttg taaatatttg gacatttgga tgttgtagtc tctatgagtc 240
aactaagtgc aactcgtgca tccagcctag caattctttg cgtccttgtc gccgggacca 300
ctcttgcgtg cgagattggt cgagttggtt ggacagaatg gtattagaat ctcccataac 360
aatgtgatag gcatcttcat caaagtgtcg gggaaggctt ttaaaattac ggacactgtc 420
cttgttggac agggccat 438

<210> SEQ ID NO 37
<211> LENGTH: 390
<212> TYPE: DNA
<213> ORGANISM: Pseudoperonospora cubensis

<400> SEQUENCE: 37
atgtcaatat tgatccattc aaggcaagtc tatgtgcagg ccagtacgca gaagtttttc 60
atctaaacgt ggtggcggag gacgacaagc caaagcccaa tgtagaaatt gagcgtctca 120
tccgtgaatt tgccgactac ttacaggagg agccgccgga cggtcttcct tctgggagtg 180
acattgagta ctcgctgcag ctgaaaccgg atgcgcgacc gtcatcacat cctccattcc 240
gtcatgctca tgtgaaggag gaagccccgc aacagtttgt gagcaagcta ctgaagaatc 300
gagcgctgct catcgccgtg ggtgttcaac atctttgcag ttctcaatcc tgcccctgtc 360
actggggaat tgccgtccaa gattcagtga 390

<210> SEQ ID NO 38
<211> LENGTH: 408
<212> TYPE: DNA
<213> ORGANISM: Pseudoperonospora cubensis

<400> SEQUENCE: 38
atgcttgagg ccaagctctt catgaacggg aagaacatcg actttatccg cacggaaaat 60
cagactcgtg tagtggctat gctggctgca aacctccgtt ctgatgtcgc gtcgtgatat 120
cacagccgca tcttcattga cgacgagctc gagcaagcgc tcaaggatgc gtttgttccc 180
tctgatcaac agcaacgact ctgtgccgct ctccgatcgt acaagcagac gagttgagta 240
gagaattacg tggcgcgatt tcgccataat ttcgctcaag ttcgtgacat ggcccagatc 300
gagaaggtga atcactttgt catcggcctt aagcccaaga cgcaaaggaa ttcagctacc 360
tatctgcgag tcgctcaagc aggcagtgac ggccacgcaa gcctatga 408

<210> SEQ ID NO 39
<211> LENGTH: 390
<212> TYPE: DNA
<213> ORGANISM: Pseudoperonospora cubensis

<400> SEQUENCE: 39
atgctacttg ccgacgccag atcaattcaa tacggtgagc cgctaggtgg cgtacgcatg 60
gttgtggaac tgaagaaaaa ggtggagagg gagaggtgcc ataaagccca aacatttgga 120
aaacttgtag ctgctagtat gaaagcgctc ctggattgta ctccaattgg attgtagacg 180
gatttgacag accaatggca cttctcgtgg ttcaacgaga agaaagtgct gacatatctc 240
agcatagcgc acccgaagaa cgcgtttgac ttcattgcgg cagctgttgc tgagtctgca 300
agcttgaaac cattcattgt gccgttcatc ggtcgagagt caagatcgac aactttctgc 360
ctatgcctga tgatggtgca gacgaaatga 390

<210> SEQ ID NO 40
<211> LENGTH: 534
<212> TYPE: DNA
<213> ORGANISM: Pseudoperonospora cubensis

<400> SEQUENCE: 40
gtagaagtaa ttgtgcaaca gcgcatggaa atcaatgttc tttgtgaacg tattgtgcac 60
gcgcagagta gtttgaagct tggtagagta caacttgacc tcgtattcaa gcttgaaatc 120
cactggccac atagtacggg ttgagtcact tgcggccatg gtcaatatgg cgacactggg 180

```
ctgagtctcg tccgcaccaa tctcaatact gaccaaggac cagttcgtga cgcgggcaaa    240

cccgtccttg ggcaatccct cagcatttcc atagtttgga aacacgatgg ggattccacc    300

acggatagga tcaataccat cctggtgcga ctggtttgac aggaagagaa ggttcaggtt    360

cggatcattc attccgcaaa acgacttgac gtgagcgcca aagagagcca ctttcgcact    420

ggcaccagtt ggatgcgtga gtttaatcgt ctctagctcg gcggacgcaa cgtctagcaa    480

cgccagcaat gttgacacta aggccacagt cttgaacacg aacgagtaga ccat          534


<210> SEQ ID NO 41
<211> LENGTH: 300
<212> TYPE: DNA
<213> ORGANISM: Pseudoperonospora cubensis

<400> SEQUENCE: 41

tcatagattg gcgtagatcg agtctgcact cacaacagca gtcgcgtgag gtagcatccc     60

ggaaaataag tccattgccg caaagccccg cacttcacac acaaacaacg ccatccccga    120

gacgcctaag tacaggaact agggcatgag tcgaactgcc tcagacaagt gccagcctgg    180

ccactcacac tggtcaagac cgctacgata gagatacgtc gctagtgcaa ccgcgtagca    240

agccgtcatt gctgacactg ctagtgctaa tccagtgaat ccaagctttg tccggaacat    300


<210> SEQ ID NO 42
<211> LENGTH: 2514
<212> TYPE: DNA
<213> ORGANISM: Pseudoperonospora cubensis

<400> SEQUENCE: 42

gtcggcctct gtgagcagcg ccaagaccaa aattttcacc gcaggttcgc gataactcaa     60

tttgtatatc gacagcaaag tgtttctttc cgagtctgaa aatggtcgac tcgatctaca    120

tgcgcgtaac atttccaccg ctgcttctgc tcctgtcatt ttcaatcgct tgctcggtac    180

actcgttcca gctcgagcac agactgcagc aagttgtagt ctcgcgtcga ttgtctcggt    240

ttcaaacgtc ttcaaacggc ggtggatact gtaacatgcc acgtccatca gactacttgc    300

ctcactagga actctgatat caaccatgcc atccgacgat tcttccacac gaccaagtgg    360

aacgagcatg cgaaattctg atcgcgatgt gtcacgaggg ttttgcaaca ccagcaccaa    420

gtatcggtgg aacctcggca ggaagtcgtc aaattgctgc ttcgtcgcta ggacatagcc    480

tttgtgctcc gcagattcga attgcatctc gtcattcaag tcgaacgtca gcttgaaccg    540

gggcagctca attttcagga caccatgcga agatctcaag ggatgaagaa actgctcctc    600

ttcgaacttc gtcaatatcc cgaaaacact ccaaagcggt tcctcttttc gaacaacccg    660

gtcatagtcg ttgagctgac tcatgagctc gtggtaagga cgcttggtgt cactgaaagg    720

cactttatag cattgcagag aaccgctgtc gtcaaatgta gcaacgaaaa agacctctcg    780

acacttggcc tttttcggac gaaagagtac acagttttgc tctacccaat accagtgtga    840

atacagctcc cgcaatcgcg ctggcaactg ttcgctcaat gcttgaaccc aactcacgga    900

gcatatttgc aaagtcctgg tgatcgcgcc cgaagtgttt gcaagcagtt cttggacaaa    960

aagctctgcg tcttcttttc caagtgcaaa gtcgtacaat cgatcgcaaa acgttcgttc   1020

agttcgaaaa gctccattcg taaagaatac ttcgaaattg cagtatccaa agagagactg   1080

gaatctcttg tggttacgaa tgtcagctgg cagacctcca ggggcatagc cgtcagtaag   1140

aacgacaccc gagaaaaggt tcatcgaata gtgcacatcc attgactcgt ccaacgcttc   1200
```

aaagcaagtg ccaaagtgcc caccaaccag cgaaagctca tcaaattgtt tccattccaa 1260
atgttcagga gacgtcgcac ttaccaaacg tagtaagcca gtgagcacaa catctgttcc 1320
gtgatttttc acgtaaacga taagctctga cactctacga gacatcgcct cggcaatttt 1380
actctcgatg cgaagcattt gattggtaga cttccgatca atggttgcac aaaagaatga 1440
agtgcgaaac aacacgatca tttcacaaac ttcttgagcc gcttcgtcat cccatggtcc 1500
aagactatag gccaacagcg tgaaaccata taaaatgcat tccttccgac ggatttctgc 1560
aacacgatca ggcgaggatt ccttcttata ttcgatgcac gcatcccttg cccagcatct 1620
cgccattcta gcaaacgtct tcacaattgc ccttgcagcg gacgagtact gcgacgtaaa 1680
acccgccagc tcactcagaa gtgggacaga ctcgaagcta cggggggtct gcttgagttt 1740
gctggcaata ctctcgagtg tagcacagaa tgtttctaag ccttcgtccc cattaaacat 1800
gtcagacttc cagagtagct gagggtgaag atcgtcagtg agtgcacccg cttggtagag 1860
cgattgccgc acgatgattt ctacgcatag acttgaccac ggaagaacgt catcaagtag 1920
agcccactga agcttcctat actgctgatt gggaaatgca cgcaacgatc caagggcaat 1980
gaaagacatc ctatcaaact cttcgggttg ctggtgaaga ctggcatata tcatgtttcc 2040
ccttgtgtcc ccttctccag gccaatcatt catccactgc aaatggttga gcgattgagg 2100
catcttctca gtgaagtctt caatcacgct cgattgtgta aactcaaaag ggttgatctt 2160
cacaccatat gcgtccaccc acgtcaaagc cgttccaggt aaggttggat tccaaacaca 2220
ttcatttctg tactgagaca gattgtacaa tctgtccaca gtacttggtc ccaatgaagt 2280
tggaagcgag aatggagcga ggcttgctgt aaacaccttg ctggtcactg ttatcgctct 2340
acgtggtgca ttctggtagt agaactgctg ccatgtcgtg gggctcaagg tcggcaaagc 2400
tgattttcca ttgataggaa caagagatcg ctgtgcagct aagcacaagc tgcccaagat 2460
ttcaatattg cgcggcatcg tcatcatgaa aatcacttga attgcgtcgc tcat 2514

<210> SEQ ID NO 43
<211> LENGTH: 483
<212> TYPE: DNA
<213> ORGANISM: Pseudoperonospora cubensis

<400> SEQUENCE: 43
ggccggaggt gcacagatgc cgtcgttcaa gaccgcgagc gacataaatt gcctggaccg 60
actgcagtac ttctgaagaa acgtgacgct cctgctgaac ttcagcgcgg accagctgtt 120
tctcaagtga aagttcgtgt ggcggtcgat gtgatcgcga agcgcattgt tttgacgttg 180
agtatgaaga cgtgcttgaa gtacggggac tagagcaggc gcgatggtat caaaaggcac 240
gcgccttgtc cagtgaaagg tttggcaggg gcgatgtaga agcgcgcgac ggtggtgcgt 300
atgctctact cgtagggcca ccggacgctt tcgtctgtca gcaacacaat tgacacgaag 360
cggagaaagc acgaagccgt tgtgctacga cgcagctgag ctaaggacca gtttgaagag 420
aagcggtgct acacagtgct ctactttgac cacgcagagt gcaccgccaa gtactgggac 480
tga 483

<210> SEQ ID NO 44
<211> LENGTH: 1094
<212> TYPE: DNA
<213> ORGANISM: Pseudoperonospora cubensis

<400> SEQUENCE: 44
atgtttgact ggcactttac gctccgtggt ccccgtggca cggagttcga gggaggtgtc 60

```
taccacggac gcatcatttt gccgtccgac tacccgttta agccgcccaa cattatgttg    120

cttacggtac tacacgactc tacctttata aatcgtatgg acgaagcctc cttgacactt    180

tgatttgtgc tattgcagcc caacggccgc tttgaagtaa agaagaaaat ctgtctgagc    240

atctcggcgt accacccgga ggagtggcag ccagcgtggg gcgtccgact catcttggag    300

gcgctgatca gctttatgcc tacaaagggc gaaggtgcta ttggcgcctt ggacttttct    360

gctgatgaac ggaagagact ggcgaaattg gtacgcgtag atagagttgt agagacgtca    420

gcgtgctgct aatgatgcgc tgcatgcagt cggtcgacta taagtgcgat acttgcggac    480

gagttgtgga cttgctaccg gagctggact ctagcaatga gaaggaaaaa aagccgtcga    540

agtacacgga acagattgcg cagctacaca ttcacaacct ggaaagcgcc ccctcgtcta    600

gtgcagcggc ggatggaaag aagactgcag atgccacagc tatggaacgt gcctcctctt    660

ctactgtggc tacagatgga aacgagactg cccatactgc agcagtggct gctgaacatg    720

gcttgaaaga tgcgaaaaca gctccacaca atagtgctga gactcatgag aaggccgcgg    780

ttaatagcaa gcccgcttcg acagctgagg tctcagccac agatgtctct aatattaccg    840

atgctagcga ttctgctagc gctcaagcca cagtgtcaga tcttgctgag gaagcagtag    900

cagagactga aacgccggca gtgactgaac ctcaccggac cgttgacacc ccgatcgagg    960

ctcagggcat agctcaagtg cgtgagtcag acagtgtgga cacattgctg cattacctga   1020

ctattgcaat cgtcgttgca ctctttgcac tcatctacaa aaagctattg caaatgcatg   1080

gtctactaca gtaa                                                     1094
```

<210> SEQ ID NO 45
<211> LENGTH: 794
<212> TYPE: DNA
<213> ORGANISM: Pseudoperonospora cubensis

<400> SEQUENCE: 45

```
taagtgtaga ttacgttgct cgtgatattg atgtgatcgt tgctaataag ctcaaagccg     60

tccatactct tggcgacttc gcctcccacg cttgagttga gcgtgaggcc agtaatggga    120

gtatagctgg agctttcgac attgaatgct cgaaagggca tattgaggag gttgaaatcc    180

gagagcgtcg agttgatgac tttgttcagt ccgaaaaaga ttggtctgat gacctctttt    240

ccttgaggcc agtaccatgc accttgtcca tcgaatgtgc cggagccagt gacggtgagg    300

ttgttccctt gcagtccaat taaaggacct tttcatagct gaaggaatca aacaaaagtc    360

agattggact gaaaataacg agaacaagac acgcagctaa gtaactcacc atgggtccaa    420

aagtgctgat gcctttgaac atgattcgta tgttgttctt tagttccatg aagttcaaca    480

tcacgccagc aggcaccctg agggaatcaa cgacgatggt gtcacactcg ctgacatcgg    540

tgttattgat gtagtctccg gtgagaatgc agacgccctt ggggaccgac gggtgtgatc    600

cgtcgggact gttgtggtca ggtgtcttct gcttggggct gttttggttg gggttgcttt    660

gggaaggtcc ggggccaatt gagttgttgg aattgccgct ggttggggag aacccagtct    720

cacaattgtc agacagcgcg tgggagctag ctaccagaag agcaatgttc aagacaggaa    780

acaaaagctt caca                                                      794
```

<210> SEQ ID NO 46
<211> LENGTH: 910
<212> TYPE: DNA
<213> ORGANISM: Pseudoperonospora cubensis

<400> SEQUENCE: 46
ttacatccgc tgagcgtgcc cgtttccctg gttcttgcgc gggtagttaa agatgcggtg 60
tcccacctcg cggtagtaaa cgcatagccc ttgacggcgg catgccttga tcgacaggca 120
ctgcggacga gaggaaaaca tcgccatctc gatcgactcg tcgccaaccg gagctgtgac 180
gtgggaagcg tccattgaat ttgcatccgg cggtcgtgcc gtacgcaagc ggtgcgacgc 240
ggcgccacca aaatgggcgc gatcgtacac ttgcgcggca gcgatagcga tggcgtcgcg 300
aagggtctca cagttgagat agttgacctc cttctgcgtc tcgggcttga gaccggcgat 360
gaaaggttcg actggtcgag ctgatacatc tggtgaatct gcatgatggt ctcacgtaac 420
cgagccacgt aatcttcagc cgccccatac tggtggcagg ctcgcagggc cgcgcgcagc 480
cgctgttgct ggttgacagg acaaacgctt cgctgaagac gctctcgaat tcgtcgaggt 540
cgcggatggg caagttgtca atcatcaaac gatgcgtgag gaacgacacg gcgctgctgt 600
gaagacccga gcatatgatc gctataacgc gtggctggtt ctcagcgcgc gtgttgtcat 660
tgttgcagcc tctcatgtac accttggccc cgaacatgta accatcaaag ttctcactgg 720
gctgccccca gaaggttggc atcgcagccc ttggaatctt gaactcgcgc ctgttcgcct 780
gggtctgact ctgttccatg aggatagctc gaaactcttg gcttcggttg gcgaccgtgt 840
gacggacgtc gcgcactgat tgggcaagcc cttccagcat catgaagacg aggttgtttt 900
cttcttccat 910

<210> SEQ ID NO 47
<211> LENGTH: 219
<212> TYPE: DNA
<213> ORGANISM: Pseudoperonospora cubensis

<400> SEQUENCE: 47
tcacggactt gagcaatgat gcgccacgta ctcctccaca ctacccgtct gcttgcacga 60
tcgaagagcg gcacgaagtc gttgctgttg gtccgaggga acgaactcat ccttaagggc 120
ttgctcaaat ttatcaatgt cgtgaatggg ctcatcatcg atgacgatac ggctgtgata 180
ccacgacgcg gcaccagaac gaaggtttgc ggccagcat 219

<210> SEQ ID NO 48
<211> LENGTH: 1296
<212> TYPE: DNA
<213> ORGANISM: Pseudoperonospora cubensis

<400> SEQUENCE: 48
ctaaatcttg atcgacaatt cttcagtgtc agggtcacgc ttaggaactg caaagatgtt 60
ggacactcat ggcgatgagc tgcgctcgat ccagttttct ttagtagctt gctcacaaac 120
tgttgcagga cttcctgctc cacatgagca tgacggaacg gaggtcgtga tgatggtcgc 180
gcattcggtt tcagctgcag cgagtgctca atgtcgcgct caggaagaag gccgtctggt 240
agttcctcac gtaggaaatc ggcaaattca cggatgagac actcaatctt cgcatcggga 300
tttggcttgt cgtactccgt taccacgtct agatggaaga cgtctgcgta ctggcctgca 360
aaaagacttg cattgaattg acctatgtcc acatactcaa tttctggttc cgacgctggc 420
aagtgcgtcc acttaagggg aagttgtggc cgtgacggtg ttgccgccca catcaaccgg 480
cgctgagccc aatcaatagc cggattctca cgctgaagcc gagtctgacc caggattcca 540
tcaaaatctt gctatagtga ccattcaacc accgcgacca agcacgaacg ccctacgatc 600
agcatattga cggtatattg ccacgaaaga gttgtcttca ccttctcttc gaagtcgcgc 660

```
gcctgcagct ccaactgaaa cgcatgcgtt agcgctcaca acagatcacg gcgcacaatg    720

cagtgcgtcg caccagagtc acaaacattc ggagtgacta gtcttgcacc ttggccgttt    780

cagatataag accatcaccc tgaacttgca ccttatccag acggatctcc atggcacaca    840

cagagacgcc aatcacacag cgcgcatcac cggctgcctc ttctatctcg aacacagctg    900

gggccaaaaa atcaggatca ccacatggaa acttttgttc acaaggctca acggatactc    960

cacttacatc cgctgagcac gctcgtttcc ctgacgcttc tttgagcaac tggcaatgcg   1020

atgaccacct tcgcgacagt agaagcacag accccggcgg cggcactgca cattcgtcgg   1080

acgagacgtg acctgcgaaa tgtccatggg atcggactca atgacacgca actggcgcgg   1140

acgacgcatt gggttcccac tgaagtgcgc tcgttcataa gtttgtgcgg ccgtcactgc   1200

ctgcttgagc gacgtgtagc ataggaagtt gacttccttc tgggtcttgg acttgacacc   1260

ggaaacaaag tgatccacct tgtcaatctg tgacat                             1296
```

<210> SEQ ID NO 49
<211> LENGTH: 286
<212> TYPE: DNA
<213> ORGANISM: Pseudoperonospora cubensis

<400> SEQUENCE: 49

```
tcagcccacg agcagaggta cagcaggcgg tcgctctgac cccgcgtact gagaaaccct     60

tgatgacata cacctgctga tcgtccgtat tgtagagacg cggcgcggac ttggtgatct    120

ctcgcgcccg aaagatctag ggtacttcca gcaactcctt gagctggtcc acattgaacg    180

taacatgcct accacgagca acatagcgat gagagaaagc gagtcggtac gcgttctcgc    240

cgatgcgctt ctcgactgga aagggtccgt accacttgcg gagcat                   286
```

<210> SEQ ID NO 50
<211> LENGTH: 570
<212> TYPE: DNA
<213> ORGANISM: Pseudoperonospora cubensis

<400> SEQUENCE: 50

```
ttatatcagt gcaaaatggc tcactatggc aagttgcatg agcacgaaag aaagcatcgt     60

catcatggca gcagacgcaa gtcgctgtag cagtcgtcca agtcgaaaac gtaataattg    120

aagcccgcgg catttgagtt caatcaacaa tattgcgaac aagaagacca catagtttcg    180

cgggaagaag cgcgatgcta gcaatagatt catatgagga cgctggtgca ttcaagaaaa    240

ccatgctcaa agccgccttg tcgatgctga tgataagcat agatatcatg atcagcagag    300

aaaacatcat caagctcgca ttggttggaa cttccagcag cacaaattct tagtcaacta    360

actgcatgca aacttctgca ggtttgcatg cagcgcctcc ttacgctttt caagaagctt    420

ttcaggtggc ttcagttgcg acagtcgctc ctggtccact tcattcattt gctgtttgac    480

agcatgccgt tgcagtatcg tctttcttgt ctgtttgttt acgtgtggct ccattgtatt    540

ttcttgcagc aaattttcga acgtcgtcat                                     570
```

<210> SEQ ID NO 51
<211> LENGTH: 552
<212> TYPE: DNA
<213> ORGANISM: Pseudoperonospora cubensis

<400> SEQUENCE: 51

```
atgatacaat ttctggagca cggtgagaat gaagaagtac cgaaagctga cgttgcttgt     60
```

-continued

```
atgtataagg cagacatgtc cgtggactgg cagatcgagc tgcatcgcat ccctcgtagc    120

tgggacctac cttcgataga agcgtagctt aggttaattg agcgtaatga gcgtaaaaat    180

gagaagctct gggagatacg cctgaggccg agagaccagt agccttagca gtgattcaat    240

gagcgaagaa gcagcaacca gcgtcccaag gtcaatatcc aatggcgtat caacaaatac    300

tgtggctact gtaagcgcag cagtgactgc tctatgaccc tgcttcacca gtcaatcgac    360

cacaaaacaa tagtaacaat tcgtaccaac caagccgata ccagtcgtca aaggcccata    420

gcggtgacga ccagcggaac gggtaacaag cagatcgccg agatggttgc gatgatgaaa    480

actctaaaga aactgcaaga tgatgtgtgc gtcgcagctc attttatcag ccgcaagcac    540

atgctcaaat ag                                                        552


<210> SEQ ID NO 52
<211> LENGTH: 567
<212> TYPE: DNA
<213> ORGANISM: Pseudoperonospora cubensis

<400> SEQUENCE: 52

atggcgctac ctgtgggcag ctcttctttc ccgctagagg cttccttcgt taggaggtga     60

gggtgtgagc atccagtgca agtacatcgt cagaagcggt ggcagggctt tgcaagggaa    120

tgaacagacg agcgaggagg tgaccgacgc gtcgaccgag cgcagccagg aacattaacc    180

gtacgtgaga ctgcgtgcag aatttttgtt ttctcatcgc ttgactcaat ccatgtcgaa    240

caagcaaagt accatgacaa gcgcctcgaa aacgcgcgtg tgaacagcag tggactaatc    300

atggtcaacc agcacatctg ggtgccaaac gacgccgtag atctcctcca acgcattttc    360

gtcgtagccc actgcgaaaa ccaaaggcac cgcggacttg gatctgtggc gaagaccctg    420

aacgacattt tcagcatcca tgacgttgag tccaagtgca gaaggttcct cagtcactgt    480

ttgttgtaca agcacatcaa aagcgtcaac gtgatcccgc agagacccac gtacgacgca    540

acccagcata acaagctgtt gcactga                                        567
```

METHODS FOR DIAGNOSIS OF *PSEUDOPERONOSPORA CUBENSIS* INFECTION AND SELECTION OF PLANT RESISTANCE GENES TO THE SAME

STATEMENT OF PRIORITY

This application is a 35 U.S.C. § 371 national phase entry of International Application No. PCT/US2017/050059, filed Sep. 5, 2017, which claims the benefit, under 35 § 119(a) of U.S. Provisional Application No. 62/384,817, filed Sep. 8, 2016, the entire contents of each of which are incorporated herein by reference herein.

STATEMENT OF FEDERAL SUPPORT

This invention was made with government support under grant number 13-8130-0254-CA and grant number 12-25-B-1688 awarded by USDA/APHIS. The government has certain rights to this invention.

FIELD OF THE INVENTION

The invention relates to methods for diagnosis and treatment of *Pseudoperonospora cubensis* (*P. cubensis*) infection, and methods for distinguishing between different types of *P. cubensis*, as well as methods for selecting genes conferring resistance to *P. cubensis*.

BACKGROUND OF THE INVENTION

In the past decade, a number of plant pathogens have emerged in the United States causing significant damage in agricultural and natural ecosystems and threatening food security (Fisher et al. 2012). Several recent epidemics have been caused by oomycete pathogens such as the hemibiotroph *Phytophthora infestans* (Fry et al. 2015), the causal agent of late blight of potato and tomato, and obligate plant pathogens within the family Peronosporaceae that cause downy mildew (Cohen et al. 2015; Gascuel et al. 2015; Holmes et al. 2015). Downy mildew pathogens include diverse genera such as *Pseudoperonospora* spp. (Gent and Ocamb 2009; Holmes et al. 2015), *Plasmopara* spp. (Gascuel et al. 2015), *Peronospora* spp. (Roberts et al. 2009; Testen et al. 2013), and *Bremia* spp. (Michelmore and Wong 2008) that infect economically important crops and are usually host-specific due to their biotrophic nature. Diagnostic tools for oomycete pathogens range from visual inspection to culturing, serology, and PCR-based tests (Martin et al. 2012). Due to their inability to grow in media and, consequentially, a lack of genomic resources for marker development, downy mildew pathogen diagnostics has mainly been performed by visual inspection of pathogen structures on infected plants (Holmes et al. 2015). However, signs of the pathogen and symptoms of the disease are usually detected when the disease is at advanced stages (>30% severity, FIG. 1) and control strategies, such as fungicide applications, are less effective (Gent et al. 2015; Homa et al. 2014; Ojiambo et al. 2010). In addition, while the main dispersal mechanism of downy mildew pathogens is through airborne sporangia that can travel several miles on wind currents, several downy mildew pathogens are known to be seedborne (Cohen et al. 2014; Gascuel et al. 2015; Testen et al. 2013).

Increasing diagnostic and airborne inoculum monitoring capabilities for downy mildew pathogens could aid in restricting movement of infected plant material (Djalali Farahani-Kofoet et al. 2012) and improving forecasting and alert systems that predict inoculum dispersal (Ojiambo et al. 2015). Recently, PCR assays have been developed for detection of the downy mildew pathogens of cucurbits (*Pseudoperonospora cubensis*) (Summers et al. 2015), hop (*Pseudoperonospora humuli*) (Gent et al. 2009), basil (*Peronospora belbahrii*) (Djalali Farahani-Kofoet et al. 2012), spinach (*Peronospora effusa*), and beet (*Peronospora schachtii*) (Klosterman et al. 2014) on seed or from air samples to develop alert systems based on primary inoculum levels. PCR primers and markers in these studies were developed from conserved regions such as the internal transcribed spacer (ITS) or mitochondrial genes, resulting in nonspecific amplification of closely related species (Gent et al. 2009; Klosterman et al. 2014). Such assays have limitations for monitoring inoculum in environmental samples since different downy mildew species may be present at the time of sampling due to production of a variety of susceptible crops in the same region (Gent et al. 2009; Klosterman et al. 2014). Disease alert systems based on airborne inoculum require species-specific diagnostic assays for timely initiation of disease control measures for a particular crop that is susceptible to its corresponding downy mildew pathogen (Gent et al. 2009; Klosterman et al. 2014).

Thus, the present invention overcomes previous shortcomings in the art by providing species-specific diagnostic tools for *P. cubensis* as well as tools for identifying genes useful for producing plants having resistance to *P. cubensis*.

SUMMARY OF THE INVENTION

A first aspect of the invention provides a method of diagnosing a *Pseudoperonospora cubensis* infection in a cucurbit plant, comprising detecting at least one polynucleotide selected from the group of nucleotide sequences of SEQ ID NOs:1-52, or a fragment thereof, in a sample from the cucurbit plant, thereby diagnosing a *P. cubensis* infection.

A second aspect provides a method of diagnosing an infection in a cucurbit plant by a type of *Pseudoperonospora cubensis* that infects cucumber and cantaloupe, comprising: contacting a sample from the cucurbit plant with an oligonucleotide that hybridizes to the nucleotide sequence of SEQ ID NO:16, and/or a fragment thereof, but does not hybridize to the nucleotide sequence of SEQ ID NO:52, and/or a fragment thereof; and detecting whether the nucleotide sequence of SEQ ID NO:16 and/or fragment thereof is present by detecting binding between the oligonucleotide and the nucleotide sequence of SEQ ID NO:16, and/or fragment thereof, wherein the presence of binding between the oligonucleotide and the nucleotide sequence of SEQ ID NO:16, and/or fragment thereof, identifies the *P. cubensis* as a type that infects cucumber and cantaloupe, thereby diagnosing an infection by the type of *P. cubensis* that infects cucumber and cantaloupe.

A third aspect provides a method of diagnosing an infection in a cucurbit plant by a type of *Pseudoperonospora cubensis* that infects pumpkin, watermelon, and squash, comprising: contacting a sample from the cucurbit plant with an oligonucleotide that hybridizes to the nucleotide sequence of SEQ ID NO:52, and/or a fragment thereof, but does not hybridize to the nucleotide sequence of SEQ ID NO:16, and/or a fragment thereof; and detecting whether the nucleotide sequence of SEQ ID NO:52 and/or fragment thereof is present by detecting binding between the oligonucleotide and the nucleotide sequence of SEQ ID NO:52, and/or fragment thereof, wherein the presence of binding between the oligonucleotide and the nucleotide sequence of SEQ ID NO:52, and/or fragment thereof, identifies the *P. cubensis* as a type that infects pumpkin, watermelon, and squash, thereby diagnosing an infection by the type of *P. cubensis* that infects pumpkin, watermelon, and squash.

A fourth aspect provides a method of diagnosing an infection in a cucurbit plant by a type of *Pseudoperonospora cubensis* that infects cucumber and cantaloupe, comprising: contacting a sample from the cucurbit plant with a pair of oligonucleotides that hybridize to the nucleotide sequence of SEQ ID NO:16, and/or a fragment thereof, under conditions whereby nucleic acid amplification can occur, thereby producing an amplification product; and detecting whether the nucleotide sequence of SEQ ID NO:16, and/or fragment thereof, is present by detecting binding between the amplification product and an oligonucleotide probe that hybridizes to the nucleotide sequence of SEQ ID NO:16, and/or a fragment thereof, but does not hybridize to the nucleotide sequence of SEQ ID NO:52, and/or a fragment thereof, wherein the presence of the amplification product identifies the *P. cubensis* as the type that infects cucumber and cantaloupe, thereby diagnosing the infection of the cucurbit plant as being by a type of *P. cubensis* that infects cucumber and cantaloupe.

A fifth aspect provides a method of diagnosing an infection in a cucurbit plant by a type of *Pseudoperonospora cubensis* that infects pumpkin, watermelon, and squash, comprising: contacting a sample from the cucurbit plant with a pair of oligonucleotides that hybridize to the nucleotide sequence of SEQ ID NO:52, and/or a fragment thereof, under conditions whereby nucleic acid amplification can occur, thereby producing an amplification product; and detecting whether the nucleotide sequence of SEQ ID NO:52, and/or fragment thereof, is present by detecting binding between the amplification product and an oligonucleotide probe that hybridizes to the nucleotide sequence of SEQ ID NO:52, and/or a fragment thereof, but does not hybridize to the nucleotide sequence of SEQ ID NO:16, and/or a fragment thereof, wherein the presence of the amplification product identifies the *P. cubensis* as the type that infects pumpkin, watermelon, and squash, thereby diagnosing the infection of the cucurbit plant as being by a type of *P. cubensis* that infects pumpkin, watermelon, and squash, loupe.

A sixth aspect provides a method for determining a risk of a *Pseudoperonospora cubensis* outbreak, comprising: detecting at least one polynucleotide selected from the group of nucleotide sequences of SEQ ID NOs:1-52, or a fragment thereof, in a sample from a plant or in an environmental sample, wherein the presence of the at least one polynucleotide indicates the presence of *P. cubensis* and the risk of a *P. cubensis* outbreak.

A seventh aspect of the invention provides a method for determining a risk of a *Pseudoperonospora cubensis* outbreak by a type of *P. cubensis* that infects cucumber and cantaloupe, comprising: contacting a sample from a plant or an environmental sample with an oligonucleotide that hybridizes to the nucleotide sequence of SEQ ID NO:16, and/or a fragment thereof, but does not hybridize to the nucleotide sequence of SEQ ID NO:52, and/or a fragment thereof, and detecting in the sample whether the nucleotide sequence of SEQ ID NO:16 and/or the fragment thereof is present by detecting binding between the oligonucleotide and the nucleotide sequence of SEQ ID NO:16, and/or fragment thereof, wherein the presence of binding between the oligonucleotide and the nucleotide sequence of SEQ ID NO:16, and/or fragment thereof, indicates the presence of the type of *P. cubensis* that infects cucumber and cantaloupe and the risk of a *P. cubensis* outbreak by the type of *P. cubensis* that infects cucumber and cantaloupe.

An eighth aspect provides a method for determining a risk of a *Pseudoperonospora cubensis* outbreak by a type of *P. cubensis* that infects pumpkin, watermelon, and squash, comprising: contacting a sample from a plant or an environmental sample with an oligonucleotide that hybridizes to the nucleotide sequence of SEQ ID NO:52, and/or a fragment thereof, but does not hybridize to the nucleotide sequence of SEQ ID NO:16, and/or a fragment thereof, and detecting in the sample whether the nucleotide sequence of SEQ ID NO:52 and/or the fragment thereof is present by detecting binding between the oligonucleotide and the nucleotide sequence of SEQ ID NO:52, and/or fragment thereof, wherein the presence of binding between the oligonucleotide and the nucleotide sequence of SEQ ID NO:52, and/or fragment thereof, indicates the presence of the type of *P. cubensis* that infects pumpkin, watermelon, and squash and the risk of a *P. cubensis* outbreak by the type of *P. cubensis* that infects pumpkin, watermelon, and squash.

A ninth aspect provides a method for determining a risk of a *Pseudoperonospora cubensis* outbreak by a type of *P. cubensis* that infects cucumber and cantaloupe, comprising: contacting a sample from a plant or an environmental sample with a pair of oligonucleotides that hybridize to the nucleotide sequence of SEQ ID NO:16, and/or a fragment thereof, under conditions whereby nucleic acid amplification can occur, thereby producing an amplification product; and detecting whether the nucleotide sequence of SEQ ID NO:16, and/or fragment thereof, is present by detecting binding between the amplification product and an oligonucleotide probe that hybridizes to the nucleotide sequence of SEQ ID NO:16, and/or a fragment thereof, but does not hybridize to the nucleotide sequence of SEQ ID NO:52, and/or a fragment thereof, wherein the presence of binding between the oligonucleotide probe and the amplification product indicates the presence of the type of *P. cubensis* that infects cucumber and cantaloupe and the risk of a *P. cubensis* outbreak by the type of *P. cubensis* that infects cucumber and cantaloupe.

A tenth aspect provides a method for determining a risk of a *Pseudoperonospora cubensis* outbreak by a type of *P. cubensis* that infects pumpkin, watermelon, and squash, comprising: contacting a sample from a plant or an environmental sample with a pair of oligonucleotides that hybridize to the nucleotide sequence of SEQ ID NO:52, and/or a fragment thereof, under conditions whereby nucleic acid amplification can occur, thereby producing an amplification product; and detecting in the sample whether the nucleotide sequence of SEQ ID NO:52, and/or a fragment thereof, is present by detecting binding between the amplification product and an oligonucleotide probe that hybridizes to the nucleotide sequence of SEQ ID NO:52, and/or a fragment thereof, but does not hybridize to the nucleotide sequence of SEQ ID NO:16, and/or a fragment thereof, wherein the presence of binding between the oligonucleotide probe and the amplification product indicates the presence of the type of *P. cubensis* that infects pumpkin, watermelon, and squash and the risk of a *P. cubensis* outbreak by the type of *P. cubensis* that infects pumpkin, watermelon, and squash.

An additional aspect provides a method of selecting a treatment regimen for a *P. cubensis* infection, comprising: detecting in a sample from the plant at least one polynucleotide selected from the group of nucleotide sequences of SEQ ID NOs:1-52, and/or a fragment thereof, thereby identifying a *P. cubensis* infection; and selecting a treatment regimen for the *P. cubensis* infection.

A further aspect provides a method of selecting a treatment regimen for an infection in a cucurbit plant by a type of *P. cubensis* that infects cucumber and cantaloupe, comprising: contacting a sample from the cucurbit plant with an oligonucleotide that hybridizes to the nucleotide sequence of SEQ ID NO:16, and/or a fragment thereof, but does not hybridize to the nucleotide sequence of SEQ ID NO:52; and detecting whether the nucleotide sequence of SEQ ID NO:16, and/or fragment thereof, is present by detecting binding between the oligonucleotide and the nucleotide sequence of SEQ ID NO:16, and/or fragment thereof, wherein the presence of binding between the oligonucleotide and the nucleotide sequence of SEQ ID NO:16, and/or fragment thereof, identifies the *P. cubensis* as a type that infects cucumber and cantaloupe; and selecting a treatment regimen effective against the type of *P. cubensis* that infects cucumber and cantaloupe.

A still further aspect provides a method of selecting a treatment regimen for an infection in a cucurbit plant by a type of *P. cubensis* that infects pumpkin, watermelon, and squash, comprising: contacting a sample from the cucurbit plant with an oligonucleotide that hybridizes to the nucleotide sequence of SEQ ID NO:52, and/or a fragment thereof, but does not hybridize to the nucleotide sequence of SEQ ID NO:16; and detecting whether the nucleotide sequence of SEQ ID NO:52, and/or fragment thereof, is present by detecting binding between the oligonucleotide and the nucleotide sequence of SEQ ID NO:52, and/or fragment thereof, wherein the presence of binding between the oligonucleotide and the nucleotide sequence of SEQ ID NO:52, and/or fragment thereof, identifies the *P. cubensis* as a type that infects pumpkin, watermelon, and squash; and selecting a treatment regimen effective against the type of *P. cubensis* that infects pumpkin, watermelon, and squash.

An additional aspect provides a method of selecting a treatment regimen for an infection in a cucurbit plant by a type of *P. cubensis* that infects cucumber and cantaloupe, comprising: contacting a sample from the cucurbit plant with a pair of oligonucleotides that hybridize to the nucleotide sequence of SEQ ID NO:16, and/or a fragment thereof, under conditions whereby nucleic acid amplification can occur, thereby producing an amplification product; and detecting whether the nucleotide sequence of SEQ ID NO:16, and/or fragment thereof, is present by detecting binding between the amplification product and an oligonucleotide probe that hybridizes to the nucleotide sequence of SEQ ID NO:16, and/or a fragment thereof, but does not hybridize to the nucleotide sequence of SEQ ID NO:52, and/or a fragment thereof, wherein the presence of binding between the oligonucleotide probe and the amplification product identifies the *P. cubensis* as the type that infects cucumber and cantaloupe; and selecting a treatment regimen effective against the type of *P. cubensis* that infects cucumber and cantaloupe.

In a further aspect a method of selecting a treatment regimen for an infection in a cucurbit plant by a type of *P. cubensis* that infects pumpkin, watermelon, and squash, comprising: contacting a sample from a cucurbit plant with a pair of oligonucleotides that hybridize to the nucleotide sequence of SEQ ID NO:52, and/or a fragment thereof, under conditions whereby nucleic acid amplification can occur, thereby producing an amplification product; and detecting in the sample whether the nucleotide sequence of SEQ ID NO:52, and/or a fragment thereof, is present by detecting binding between the amplification product and an oligonucleotide probe that hybridizes to the nucleotide sequence of SEQ ID NO:52, and/or a fragment thereof, but does not hybridize to the nucleotide sequence of SEQ ID NO:16, and/or a fragment thereof, wherein the presence of binding between the oligonucleotide probe and the amplification product identifies the *P. cubensis* as the type that infects pumpkin, watermelon, and squash; and selecting a treatment regimen effective against the type of *P. cubensis* that infects pumpkin, watermelon, and squash.

In a still further aspect, the invention provides a method for reducing the risk of a *P. cubensis* outbreak, comprising: detecting in a sample from a cucurbit plant or in an environmental sample at least one polynucleotide selected from the group of nucleotide sequences of SEQ ID NOs:1-52 and/or a fragment thereof, thereby identifying the presence of *P. cubensis* in the sample; and implementing a treatment regimen for a *P. cubensis* infection, thereby reducing the risk of a *P. cubensis* outbreak.

An additional aspect provides a method for reducing the risk of a *Pseudoperonospora cubensis* outbreak by a *P. cubensis* that infects cucumber and cantaloupe, comprising: contacting a sample from a plant or an environmental sample with an oligonucleotide that hybridizes to the nucleotide sequence of SEQ ID NO:16, and/or a fragment thereof, but does not hybridize to the nucleotide sequence of SEQ ID NO:52, and/or a fragment thereof; detecting whether the nucleotide sequence of SEQ ID NO:16, and/or fragment thereof, is present by detecting binding between the oligonucleotide and the nucleotide sequence of SEQ ID NO:16, and/or fragment thereof, wherein the presence of binding between the oligonucleotide and the nucleotide sequence of SEQ ID NO:16 and/or fragment thereof, identifies the *P. cubensis* as a type that infects cucumber and cantaloupe; and implementing a treatment regimen against the type of *P. cubensis* that infects cucumber and cantaloupe, thereby reducing the risk of an outbreak by *P. cubensis* that infects cucumber and cantaloupe.

A further aspect provides a method for reducing the risk of a *Pseudoperonospora cubensis* outbreak by a type of *P. cubensis* that infects pumpkin, watermelon, and squash, comprising: contacting a sample from a plant or an environmental sample with an oligonucleotide that hybridizes to the nucleotide sequence of SEQ ID NO:52, and/or a fragment thereof, but does not hybridize to the nucleotide sequence of SEQ ID NO:16, and/or a fragment thereof; and detecting whether the nucleotide sequence of SEQ ID NO:52, and/or fragment thereof, is present by detecting binding between the oligonucleotide and the nucleotide sequence of SEQ ID NO:52, and/or fragment thereof, wherein the presence of binding between the oligonucleotide and the nucleotide sequence of SEQ ID NO:52, and/or fragment thereof, identifies the *P. cubensis* as a type that infects pumpkin, watermelon, and squash; and implementing a treatment regimen against the type of *P. cubensis* that infects pumpkin, watermelon, and squash, thereby reducing the risk of an outbreak by *P. cubensis* that infects pumpkin, watermelon, and squash.

Another aspect of the invention provides a method for reducing the risk of a *P. cubensis* outbreak by a *P. cubensis* that infects cucumber and cantaloupe, comprising: contacting a sample from a plant or an environmental sample with a pair of oligonucleotides that hybridize to the nucleotide sequence of SEQ ID NO:16, and/or a fragment thereof, under conditions whereby nucleic acid amplification can occur, thereby producing an amplification product; detecting whether the nucleotide sequence of SEQ ID NO:16, and/or fragment thereof, is present by detecting binding between the amplification product and an oligonucleotide probe that hybridizes to the nucleotide sequence of SEQ ID NO:16, and/or a fragment thereof, but does not hybridize to the nucleotide sequence of SEQ ID NO:52, and/or a fragment thereof, wherein the presence of binding between the oligonucleotide probe and the amplification product identifies the *P. cubensis* as the type that infects cucumber and cantaloupe; and implementing a treatment regimen against the type of *P. cubensis* that infects cucumber and cantaloupe thereby reducing the risk of an outbreak by *P. cubensis* that infects cucumber and cantaloupe.

In another aspect, a method for reducing the risk of a *P. cubensis* outbreak by a *P. cubensis* infects pumpkin, watermelon, and squash is provided, comprising: contacting a sample from a plant or an environmental sample with a pair of oligonucleotides that hybridize to the nucleotide sequence of SEQ ID NO:52, and/or a fragment thereof, under conditions whereby nucleic acid amplification can occur, thereby producing an amplification product; detecting whether the nucleotide sequence of SEQ ID NO:52, and/or a fragment thereof, is present by detecting binding between the amplification product and an oligonucleotide probe that hybridizes to the nucleotide sequence of SEQ ID NO:52, and/or a fragment thereof, but does not hybridize to the nucleotide sequence of SEQ ID NO:16, and/or a fragment thereof, wherein the presence of binding between the oligonucleotide probe and the amplification product identifies the *P. cubensis* as the type that infects pumpkin, watermelon, and squash; and implementing a treatment regimen against the type of *P. cubensis* that infects pumpkin, watermelon, and squash, thereby reducing the risk of an outbreak by *P. cubensis* that infects pumpkin, watermelon, and squash.

In an additional aspect, a method of selecting a cucurbit plant comprising at least one gene that confers resistance to *P. cubensis* is provided, comprising introducing into the cucurbit plant at least one nucleotide sequence selected from the group of (a) a nucleotide sequence of any one of SEQ ID NOs:1-52, or a complement thereof; (b) a nucleotide sequence having at least about 80% sequence identity to the nucleotide sequence of (a); (c) a nucleotide sequence which anneals under stringent hybridization conditions to the nucleotide sequence of any of (a) and/or (b), or a complement thereof; and (d) a nucleotide sequence that differs from the nucleotide sequence of any of (a) to (c) above due to the degeneracy of the genetic code, wherein the expression of the at least one nucleotide sequence produces a hypersensitive response in a cucurbit plant comprising a gene that confers resistance to *P. cubensis*, thereby identifying the cucurbit plant as comprising a gene that confers resistance to *P. cubensis*; and selecting the plant having the hypersensitive response and identified as comprising the gene that confers resistance to *P. cubensis.*

Further provided are methods of producing a plant having increased resistance to *P. cubensis*, comprising: (a) selecting a cucurbit plant according to the methods of the invention; (b) crossing the selected plant with a second cucurbit plant; and (c) selecting progeny having increased resistance to *P. cubensis*, thereby producing a plant having increased resistance to *P. cubensis.*

In a further aspect, the invention provides an isolated nucleic acid molecule comprising: ((a) a nucleotide sequence of any one of SEQ ID NOs:1-52, or a complement thereof; (b) a nucleotide sequence having at least about 80% sequence identity to the nucleotide sequence of (a); (c) a nucleotide sequence which anneals under stringent hybridization conditions to the nucleotide sequence of any of (a) and/or (b), or a complement thereof; (d) a nucleotide sequence that differs from the nucleotide sequence of any of (a) to (c) above due to the degeneracy of the genetic code; and (e) a fragment of a nucleotide sequence of any of (a) to (d) above.

In an additional aspect of the invention, a recombinant nucleic acid construct is provided, the recombinant nucleic acid construct comprising at least one an isolated nucleic acid molecule of the invention.

In a further aspect, an isolated polypeptide is provided comprising: (a) an amino acid sequence encoded by a nucleotide sequence of any one of SEQ ID NOs:1-52, or a complement thereof; and (b) an amino acid sequence having at least about 80% sequence identity to the amino acid sequence of (a); and a fragment of any of (a) and/or (b). Additionally provided is a polyclonal or monoclonal antibody specifically reactive with the isolated polypeptides of the invention.

A further aspect of the invention provides a method for determining a risk of a *Pseudoperonospora cubensis* outbreak, comprising: contacting a sample from a cucurbit plant or from an environmental sample with an oligonucleotide that hybridizes to an isolated nucleic acid molecule and/or an antibody of the invention; and detecting whether the isolated nucleic acid molecule, or fragment thereof, is present by detecting binding between the oligonucleotide and the isolated nucleic acid molecule, or fragment thereof, and/or detecting whether a polypeptide encoded by the isolated nucleic acid molecule, or fragment thereof, is present by detecting binding between the antibody and the polypeptide, wherein the presence of the isolated nucleic acid molecule and/or the polypeptide indicates the presence of *P. cubensis* in the sample and the risk of a *P. cubensis* outbreak.

In another aspect, the invention provides a method for determining a risk of a *Pseudoperonospora cubensis* outbreak, comprising: contacting a sample from a cucurbit plant or an environmental sample with a pair oligonucleotides that hybridize to an isolated nucleic acid molecule of the invention, under conditions whereby nucleic acid amplification can occur, thereby producing an amplification product; detecting the amplification product, wherein the presence of binding between the oligonucleotide probe and the amplification product identifies the presence of *P. cubensis* and the risk of a *P. cubensis* outbreak.

A further aspect provides a method of selecting a treatment regimen for a *P. cubensis* infection of a cucurbit plant, comprising: contacting a sample from the cucurbit plant with an oligonucleotide that hybridizes to the isolated nucleic acid molecule to an isolated nucleic acid molecule and/or an antibody of the invention; detecting whether the isolated nucleic acid molecule and/or a fragment thereof is present by detecting binding between the oligonucleotide and the isolated nucleic acid molecule, and/or detecting whether a polypeptide encoded by the isolated nucleic acid molecule and/or a fragment thereof is present by detecting binding between the antibody and the polypeptide, thereby identifying a *P. cubensis* infection when the presence of the isolated nucleic acid molecule and/or polypeptide in the sample is detected; and selecting a treatment regimen for the *P. cubensis* infection.

Additionally provided is a method of selecting a treatment regimen for a *P. cubensis* infection of a cucurbit plant, comprising: contacting a sample from the cucurbit plant with a pair oligonucleotides that hybridize to the isolated nucleic acid molecule of the invention, under conditions whereby nucleic acid amplification can occur, thereby producing an amplification product; detecting the amplification product, wherein the presence of binding between the oligonucleotide probe and the amplification product identifies the presence of *P. cubensis* in the sample; and selecting a treatment regimen for the *P. cubensis* infection.

A further aspect of the invention provides a method for reducing the risk of a *P. cubensis* outbreak, comprising: contacting a sample from a cucurbit plant or from an environmental sample with an oligonucleotide that hybridizes to an isolated nucleic acid molecule and/or an antibody of the invention; detecting whether the isolated nucleic acid molecule, and/or a fragment thereof, is present by detecting binding between the oligonucleotide and the isolated nucleic acid molecule, and/or detecting whether a polypeptide encoded by the isolated nucleic acid molecule, and/or a fragment thereof, is present by detecting binding between the antibody and the polypeptide, wherein the presence of the isolated nucleic acid molecule and/or the polypeptide identifies the presence of *P. cubensis*; and implementing a treatment regimen for a *P. cubensis* infection, thereby reducing the risk of a *P. cubensis* outbreak.

A further aspect of the invention provides a method for reducing the risk of a *P. cubensis* outbreak, comprising: contacting a sample from a cucurbit plant or an environmental sample with a pair oligonucleotides that hybridize to an isolated nucleic acid molecule of the invention, under conditions whereby nucleic acid amplification can occur, thereby producing an amplification product; detecting the amplification product, wherein the presence of the amplification product identifies the presence of *P. cubensis* in the sample; and implementing a treatment regimen for a *P. cubensis* infection, thereby reducing the risk of a *P. cubensis* outbreak.

In a still further aspect, a method of distinguishing a type of *P. cubensis* that infects cucumber and cantaloupe from a type of *P. cubensis* that infects pumpkin, watermelon, and squash, comprising: contacting a sample from a cucurbit plant or from an environmental sample with a first oligonucleotide that hybridizes to the nucleotide sequence of SEQ ID NO:16 and/or a fragment thereof, but not to the nucleotide sequence of SEQ ID NO:52, and/or fragment thereof, and/or a second oligonucleotide that hybridizes to the nucleotide sequence of SEQ ID NO:52, and/or a fragment thereof, but not to the nucleotide sequence of SEQ ID NO:52, and/or fragment thereof; detecting whether the nucleotide sequence of SEQ ID NO:16, and/or fragment thereof, is present by detecting binding between the first oligonucleotide and the nucleotide sequence of SEQ ID NO:16, and/or fragment thereof, and/or whether the nucleotide sequence of SEQ ID NO:52, and/or fragment thereof, is present by detecting binding between the second oligonucleotide and the nucleotide sequence of SEQ ID NO:52, and/or fragment thereof; and identifying a type of *P. cubensis* that infects cucumber and cantaloupe when binding is detected between the first oligonucleotide and the nucleotide sequence of SEQ ID NO:16, and/or fragment thereof, and identifying a type of *P. cubensis* that infects pumpkin, watermelon, and squash when binding is detected between the second oligonucleotide and the nucleotide sequence of SEQ ID NO:52, and/or fragment thereof, thereby distinguishing the type of *P. cubensis* that infects cucumber and cantaloupe from the type of *P. cubensis* that infects pumpkin, watermelon, and squash in the sample.

Further provided is method of distinguishing a type of *P. cubensis* that infects cucumber and cantaloupe from a type of *P. cubensis* that infects pumpkin, watermelon, and squash, comprising: contacting a sample from a cucurbit plant or from an environmental sample with a first antibody that hybridizes to a polypeptide encoded by the nucleotide sequence of SEQ ID NO:16, and/or a fragment thereof, and not to a polypeptide encoded by the nucleotide sequence of SEQ ID NO:52, or fragment thereof, and/or with a second antibody that hybridizes to a polypeptide encoded by the nucleotide sequence of SEQ ID NO:52, and/or a fragment thereof, and not to a polypeptide encoded by the nucleotide sequence of SEQ ID NO:16, or fragment thereof; detecting whether the nucleotide sequence of SEQ ID NO:16, and/or fragment thereof, is present by detecting binding between the first antibody and the polypeptide encoded by the nucleotide sequence of SEQ ID NO:16, and/or fragment thereof, and/or whether the nucleotide sequence of SEQ ID NO:52 and/or fragment thereof is present by detecting binding between the second antibody and the polypeptide encoded by the nucleotide sequence of SEQ ID NO:52 and/or fragment thereof; and identifying a type of *P. cubensis* that infects cucumber and cantaloupe when binding is detected between the first antibody and the polypeptide encoded by the nucleotide sequence of SEQ ID NO:16, and/or fragment thereof, and identifying a type of *P. cubensis* that infects pumpkin, watermelon, and squash when binding is detected between the second antibody and the polypeptide encoded by the nucleotide sequence of SEQ ID NO:52, and/or fragment thereof, thereby distinguishing the type of *P. cubensis* that infects cucumber and cantaloupe from the type of *P. cubensis* that infects pumpkin, watermelon, and squash.

In a still further aspect, a method of distinguishing a type of *P. cubensis* that infects cucumber and cantaloupe from a type of *P. cubensis* that infects pumpkin, watermelon, and squash is provided, comprising: contacting a sample from a plant or an environmental sample with a pair of oligonucleotides that hybridize to the nucleotide sequence of SEQ ID NO:16, and/or a fragment thereof, and to the nucleotide sequence of SEQ ID NO:52, and/or a fragment thereof, under conditions whereby nucleic acid amplification can occur, thereby producing an amplification product; detecting whether the nucleotide sequence of SEQ ID NO:16, and/or fragment thereof, is present by detecting binding between the amplification product and a first oligonucleotide probe that hybridizes to the nucleotide sequence of SEQ ID NO:16, and/or fragment thereof, and not to the nucleotide sequence of SEQ ID NO:52, and/or fragment thereof, and/or whether the nucleotide sequence of SEQ ID NO:52, and/or fragment thereof, is present by detecting binding between the amplification product and a second oligonucleotide probe that hybridizes to the nucleotide sequence of SEQ ID NO:52, and/or fragment thereof, and not to the nucleotide sequence of SEQ ID NO:16 and/or fragment thereof; and identifying a type of *P. cubensis* that infects cucumber and cantaloupe when binding is detected between the amplification product and the first oligonucleotide probe, and identifying a type of *P. cubensis* that infects pumpkin, watermelon, and squash when binding is detected between the amplification product and the second oligonucleotide probe, thereby distinguishing the type of *P. cubensis* that infects cucumber and cantaloupe from the type of *P. cubensis* that infects pumpkin, watermelon, and squash.

These and other aspects of the invention are set forth in more detail in the description of the invention below.

BRIEF DESCRIPTION OF THE DRAWINGS

FIG. 1A: early infection (<30% severity) on a cucumber leaf; FIG. 1B: advanced infection with characteristic angular lesions delimited by leaf veins; and FIG. 1C: profuse pathogen sporulation on the underside of the leaf. FIG. 1D: early infection on a cantaloupe leaf; FIG. 1E: advanced infection with irregular, necrotic lesions; and FIG. 1F: little pathogen sporulation on the underside of the leaf. FIG. 1G: infected watermelon leaf with rounded, necrotic lesions; and FIG. 1H: little pathogen sporulation on the underside of the leaf.

FIG. 6A shows uniquely (dark grey) and multiple (light grey) mapped RNAseq reads to the *P. cubensis* genome. FIG. 6B shows uniquely (dark grey) and multiple (light grey) mapped RNAseq reads to the *C. sativus* genome.

DETAILED DESCRIPTION

Figures 1A, 1B, 1C, 1D, 1E, 1F, 1G, 1H:
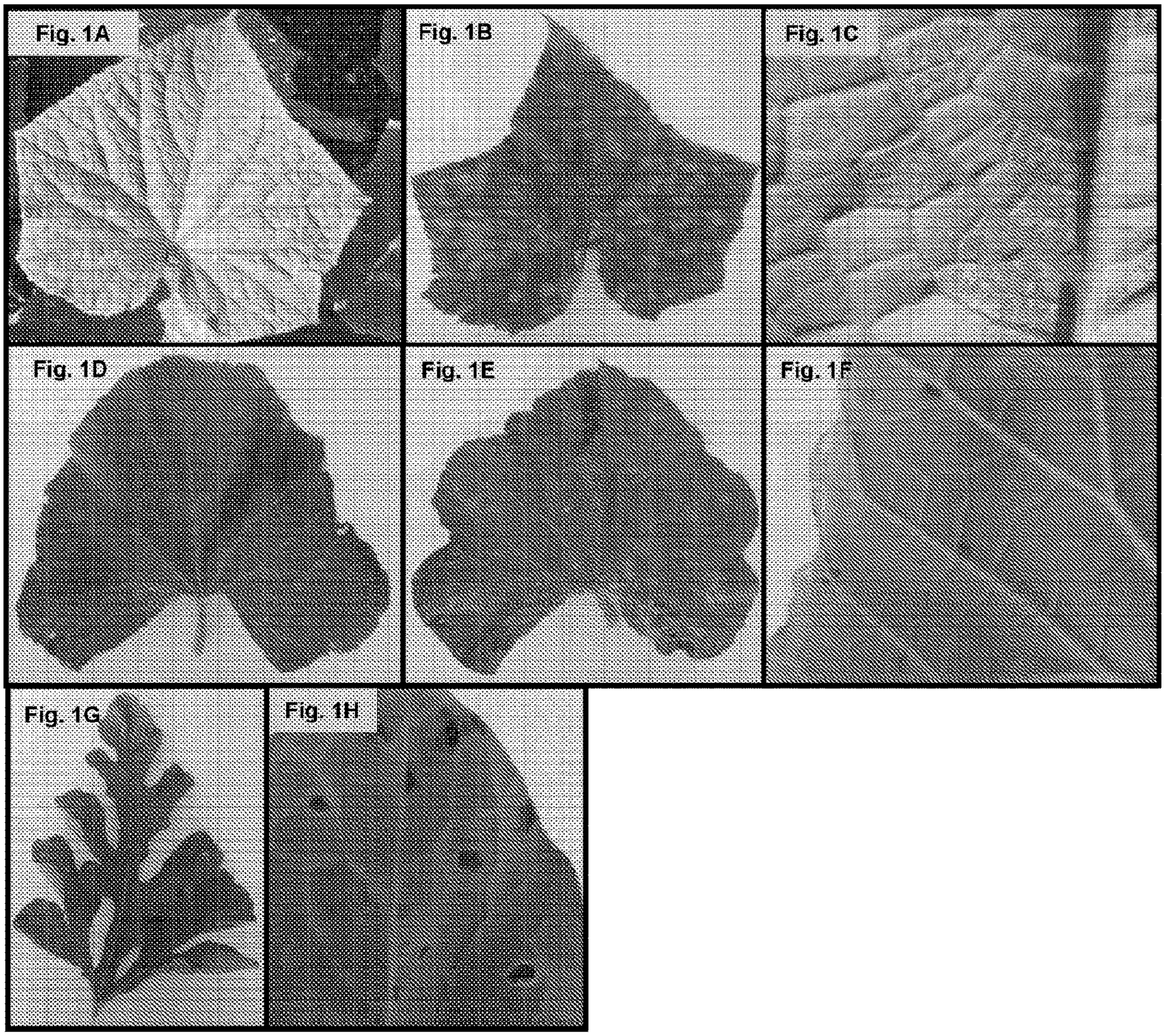
FIG. 1A-1H shows downy mildew symptoms in different cucurbits caused by *Pseudoperonospora cubensis*.

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like refers to variations of ±20%, ±10%, +5%, +1%, +0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "increased," "enhance," "enhanced," "enhancing," and "enhancement" (and grammatical variations thereof) describe an elevation of at least about 5%, 10%, 15%, 20%, 25%, 50%, 75%, 100%, 150%, 200%, 300%, 400%, 500% or more as compared to a control.

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control. In particular embodiments, the reduction can result in no or essentially no (i.e., an insignificant amount, e.g., less than about 10% or even 5%) detectable activity or amount.

As used herein, a "sample from a plant" and a "sample from a cucurbit plant" may be taken from any plant, plant part or portion thereof, including but not limited to a leaf, seed, flower, fruit, stem, and the like.

The term "cucurbit plant" as used herein, refers to any plant in the Cucurbitaceae family, including any wild genus or species, breeding line, and/or commercial line. Non-limiting examples of a cucurbit genus useful with this invention includes *Cucumis* spp., *Cucurbita* spp., and/or *Citrullus* spp. Exemplary cucurbit plants useful with this invention include, but are not limited to, cucumber, watermelon, squash, pumpkin and/or cantaloupe.

As used herein, an "environmental sample" includes but is not limited to a sample taken from the air (e.g., an air sampler, a spore trap, and any other method for collecting one or more spores for testing).

As used herein, the terms "express," "expresses," "expressed" or "expression," and the like, with respect to a nucleotide sequence (e.g., RNA or DNA) indicates that the nucleotide sequence is transcribed and, optionally, translated. Thus, a nucleotide sequence may express a polypeptide of interest or a functional untranslated RNA. A "functional" RNA includes any untranslated RNA that has a biological function in a cell, e.g., regulation of gene expression. Such functional RNAs include but are not limited to RNAi (e.g., siRNA, shRNA, antisense RNA), miRNA, ribozymes, RNA aptamers, and the like.

As used herein, "nucleic acid," "nucleotide sequence," and "polynucleotide" are used interchangeably and encompass both RNA and DNA, including cDNA, genomic DNA, mRNA, synthetic (e.g., chemically synthesized) DNA or RNA and chimeras of RNA and DNA. The term polynucleotide, nucleotide sequence, or nucleic acid refers to a chain of nucleotides without regard to length of the chain. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. The present invention further provides a nucleic acid that is the complement (which can be either a full complement or a partial complement) of a nucleic acid, nucleotide sequence, or polynucleotide of this invention.

As used herein, the term "gene" refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The terms "complementary" or "complementarity," as used herein, refer to the natural binding of polynucleotides under permissive salt and temperature conditions by base-pairing. For example, the sequence "A-G-T" binds to the complementary sequence "T-C-A." Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands. Thus, a nucleic acid (e.g., polynucleotide, oligonucleotide, and the like) of the invention can be about 70% to about 100% complementary to a target nucleic acid (e.g., a polynucleotide having the nucleotide sequence of any of SEQ ID NOs:1-52; e.g., about 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100%, or any range or value therein) and therefore hybridizes to that target nucleic acid. In particular embodiments, an oligonucleotide of the invention can be about 80 to about 100%, about 85% to about 100%, about 90% to about 100%, about 95% to about 100%, and the like, complementary to a target nucleic acid.

The term "oligonucleotide" refers to a nucleic acid sequence of at least about five nucleotides to about 500 nucleotides, for example, about 10 to 20, about 15 to 30, about 20 to 25, about 20 to 40, about 20 to 50, about 25 to 100, about 50 to 100, about 25 to 150, about 50 to 150, about 50 to 200, about 50 to 250, and the like nucleotides, which can be used, for example, as a primer in a PCR amplification and/or as a probe in a hybridization assay or in a microarray. In particular embodiments, the oligonucleotides of the invention can be at least about five to about 500 consecutive nucleotides of a nucleotide sequence of SEQ ID NOs:1-52. Oligonucleotides can be natural or synthetic, e.g., DNA, RNA, modified backbones, etc. Peptide nucleic acids (PNAs) can also be used as probes in the methods of this invention.

Thus, the present invention further provides fragments or oligonucleotides of the nucleic acids of this invention (e.g., SEQ ID NOs: 1-52), which can be used, for example as primers and/or probes. Thus, in some embodiments, the present invention provides a fragment or oligonucleotide, which is a nucleotide sequence that comprises, consists essentially of and/or consists of at least, for example, 5, 10, 15, 20, 25, 30, 35, 40, 45, 50, 55, 60, 65, 70, 75, 80, 85, 90, 95, 100, 110. 120, 125, 135, 150, 160, 170, 175, 200, 225, 250, 275, 300, 325, 350, 375, 400, 425, 450, 475 or 500 contiguous nucleotides of a nucleic acid of this invention (e.g., the nucleotide sequences of SEQ ID NOs: 1-52). Such fragments or oligonucleotides can be detectably labeled or modified, for example, to include and/or incorporate a restriction enzyme cleavage site when employed as a primer in an amplification (e.g., PCR) assay.

The terms "coding region" and "coding sequence" are used interchangeably and refer to a polynucleotide region that encodes a polypeptide or functional RNA and, when placed under the control of appropriate regulatory sequences, expresses the encoded polypeptide or functional RNA. The boundaries of a coding region are generally determined by a translation start codon at its 5' end and a translation stop codon at its 3' end. A coding region can encode one or more polypeptides or functional RNAs. For instance, a coding region can encode a polypeptide or functional RNA that is subsequently processed into two or more polypeptides or functional RNAs. A regulatory sequence or regulatory region is a nucleotide sequence that regulates expression of a coding region to which it is operably linked. Nonlimiting examples of regulatory sequences include promoters, transcription initiation sites, translation start sites, internal ribosome entry sites, translation stop sites, and terminators. "Operably linked" refers to a juxtaposition wherein the components so described are in a relationship permitting them to function in their intended manner. A regulatory sequence is "operably linked" to a coding region when it is joined in such a way that expression of the coding region is achieved under conditions compatible with the regulatory sequence.

The term "fragment" or "portion," as applied to a polynucleotide, will be understood to mean a nucleotide sequence of reduced length relative to a reference nucleic acid or nucleotide sequence and comprising, consisting essentially of, and/or consisting of a nucleotide sequence of contiguous nucleotides identical (e.g., 100% identical) or almost identical (e.g., 90%, 92%, 95%, 98%, 99% identical) to the reference nucleic acid or nucleotide sequence. Such a nucleic acid fragment according to the invention may be, where appropriate, included in a larger polynucleotide of which it is a constituent. In some embodiments, such fragments can comprise, consist essentially of, and/or consist of oligonucleotides having a length of at least about 8, 9, 10, 11, 12, 13, 14, 15, 16, 17, 18, 19, 20, 21, 22, 23, 24, 25, 30, 35, 40, 45, 50, 55, 60, 70, 75, 80, 85, 90, 95, 100, 110, 115, 120, 125, 130, 135, 140, 145, 150, 155, 160, 165, 170, 175, 180, 185, 190, 195, 200, 210, 215, 220, 225, 230, 235, 240, 245, 250, or more consecutive nucleotides (up to nearly the full length) of a nucleic acid or nucleotide sequence according to the invention.

The term "fragment" or "portion," as applied to a polypeptide, will be understood to mean an amino acid sequence of reduced length relative to a reference polypeptide or amino acid sequence and comprising, consisting essentially of, and/or consisting of an amino acid sequence of contiguous amino acids identical or almost identical (e.g., 90%, 92%, 95%, 98%, 99% identical) to the reference polypeptide or amino acid sequence. Such a polypeptide fragment according to the invention may be, where appropriate, included in a larger polypeptide of which it is a constituent. In some embodiments, such fragments can comprise, consist essentially of, and/or consist of peptides having a length of at least about 4, 5, 6, 7, 8, 9, 10, 11, 12, 13, 14, 15, 20, 25, 30, 35, 40, 45, 50, 75, 100, 150, 200, or more consecutive amino acids (up to nearly the full length) of a polypeptide or amino acid sequence according to the invention.

Polypeptides and fragments thereof of the invention (e.g., polypeptide, and fragments thereof, encoded by the nucleotide sequences of the invention, e.g., SEQ ID NOs:1-52) may be modified for use by the addition, at the amino- and/or carboxyl-terminal ends, of a blocking agent. Such blocking agents can include, without limitation, additional related or unrelated peptide sequences that can be attached to the amino and/or carboxyl terminal residues of the peptide to be administered. For example, one or more non-naturally occurring amino acids, such as D-alanine, can be added to the termini. Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Additionally, the peptide terminus can be modified, e.g., by acetylation of the N-terminus and/or amidation of the C-terminus. Likewise, the peptides can be covalently or noncovalently coupled to pharmaceutically acceptable "carrier" proteins prior to use.

In particular embodiments, nucleic acids of the present invention may encode any suitable epitope tag, including, but not limited to, poly-Arg tags (e.g., RRRRR (SEQ ID NO:53) and RRRRRR (SEQ ID NO:54) and poly-His tags (e.g., HHHHHH (SEQ ID NO:55)). In some embodiments, the nucleic acid may comprise a nucleotide sequence encoding a poly-Arg tag, a poly-His tag, a FLAG tag (i.e., DYKDDDDK (SEQ ID NO:56)), a Strep-tag II™ (GE Healthcare, Pittsburgh, Pa., USA) (i.e., WSHPQFEK (SEQ ID NO:57)), and/or a c-myc tag (i.e., EQKLISEEDL (SEQ ID NO:58)). Thus in some embodiments, the polynucleotides, nucleic acid molecules, and nucleotide sequences of the invention (e.g., SEQ ID Nos:1-52) may be modified to comprise an epitope tag.

Similarly, in some embodiments, proteins of the present invention may comprise any suitable epitope tag, including, but not limited to, poly-Arg tags (e.g., RRRRR (SEQ ID NO:53) and RRRRRR (SEQ ID NO:54) and poly-His tags (e.g., HHHHHH (SEQ ID NO:55)). In some embodiments, the polypeptide may comprise a poly-Arg tag, a poly-His tag, a FLAG tag (i.e., DYKDDDDK (SEQ ID NO:56)), a Strep-tag II™ (GE Healthcare, Pittsburgh, Pa., USA) (i.e., WSHPQFEK (SEQ ID NO:57)), and/or a c-myc tag (i.e., EQKLISEEDL (SEQ ID NO:58)). Thus in some embodiments, the polypeptides and fragments thereof of the invention (e.g., polypeptide, and fragments thereof, encoded by the nucleotide sequences of the invention, e.g., SEQ ID NOs:1-52) may be modified to comprise an epitope tag.

The term "isolated" can refer to a nucleic acid, nucleotide sequence or polypeptide that is substantially free of cellular material, viral material, and/or culture medium (when produced by recombinant DNA techniques), or chemical precursors or other chemicals (when chemically synthesized). Moreover, an "isolated fragment" is a fragment of a nucleic acid, nucleotide sequence or polypeptide that is not naturally occurring as a fragment and would not be found in the natural state. "Isolated" does not mean that the preparation is technically pure (homogeneous), but it is sufficiently pure to provide the polypeptide or nucleic acid in a form in which it can be used for the intended purpose.

In some embodiments, the recombinant nucleic acid construct, nucleotide sequences and polypeptides of the invention are "isolated." An "isolated" nucleic acid molecule, an "isolated" nucleotide sequence or an "isolated" polypeptide is a nucleic acid molecule, nucleotide sequence or polypeptide that, by the hand of man, exists apart from its native environment and is therefore not a product of nature. An isolated nucleic acid molecule, nucleotide sequence or polypeptide may exist in a purified form that is at least partially separated from at least some of the other components of the naturally occurring organism or virus, for example, the cell or viral structural components or other polypeptides or nucleic acids commonly found associated with the polynucleotide. In representative embodiments, the isolated nucleic acid molecule, the isolated nucleotide sequence and/or the isolated polypeptide is at least about 1%, 5%, 10%, 20%, 30%, 40%, 50%, 60%, 70%, 80%, 90%, 95%, or more pure.

In other embodiments, the recombinant nucleic acid construct, nucleotide sequence or polypeptide may exist in a non-native environment such as, for example, a recombinant host cell. Thus, for example, with respect to nucleotide sequences, the term "isolated" means that it is separated from the chromosome and/or cell in which it naturally occurs. A polynucleotide is also isolated if it is separated from the chromosome and/or cell in which it naturally occurs in and is then inserted into a genetic context, a chromosome and/or a cell in which it does not naturally occur (e.g., a different host cell, different regulatory sequences, and/or different position in the genome than as found in nature). Accordingly, the recombinant nucleic acid molecules, nucleotide sequences and their encoded polypeptides are "isolated" in that, by the hand of man, they exist apart from their native environment and therefore are not products of nature, however, in some embodiments, they can be introduced into and exist in a recombinant host cell.

In some embodiments, the nucleotide sequences and/or recombinant nucleic acid molecules of the invention can be operatively associated with a variety of promoters for expression in plant cells. Thus, in representative embodiments, a recombinant nucleic acid of this invention can further comprise one or more promoters operably linked to one or more nucleotide sequences.

By "operably linked" or "operably associated" as used herein, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, sequences can be present between a promoter and a nucleotide sequence, and the promoter can still be considered "operably linked" to the nucleotide sequence.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to said nucleotide sequence of the invention.

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: Computational Molecular Biology (Lesk, A. M., ed.) Oxford University Press, New York (1988); Biocomputing: Informatics and Genome Projects (Smith, D. W., ed.) Academic Press, New York (1993); Computer Analysis of Sequence Data, Part I (Griffin, A. M., and Griffin, H. G., eds.) Humana Press, New Jersey (1994); Sequence Analysis in Molecular Biology (von Heinje, G., ed.) Academic Press (1987); and Sequence Analysis Primer (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

As used herein, the phrase "substantially identical," in the context of two nucleic acid molecules, nucleotide sequences or protein sequences, refers to two or more sequences or subsequences that have at least about 80%, least about 85%, at least about 90%, at least about 95%, at least about 96%, at least about 97%, at least about 98%, or at least about 99% nucleotide or amino acid residue identity, when compared and aligned for maximum correspondence, as measured using one of the following sequence comparison algorithms or by visual inspection.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence. As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). In some embodiments, "percent identity" can refer to the percentage of identical amino acids in an amino acid sequence.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

The percent of sequence identity can be determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *J Mol. Biol.* 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, *Adv. Appl. Math.* 2:482 (1981); Smith et al., *Nucleic Acids Res.* 11:2205 (1983)).

Useful methods for determining sequence identity are also disclosed in Guide to Huge Computers (Martin J. Bishop, ed., Academic Press, San Diego (1994)), and Carillo, H., and Lipton, D., *Applied Math* 48:1073(1988)). More particularly, preferred computer programs for determining sequence identity include but are not limited to the Basic Local Alignment Search Tool (BLAST) programs which are publicly available from National Center Biotechnology Information (NCBI) at the National Library of Medicine, National Institute of Health, Bethesda, Md. 20894; see BLAST Manual, Altschul et al., NCBI, NLM, NIH; (Altschul et al., *J. Mol. Biol.* 215:403 (1990)); version 2.0 or higher of BLAST programs allows the introduction of gaps (deletions and insertions) into alignments; for peptide sequence BLASTX can be used to determine sequence identity; and, for polynucleotide sequence BLASTN can be used to determine sequence identity.

Two nucleotide sequences can be considered to be substantially complementary when the two sequences hybridize to each other under stringent conditions. In representative embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 400° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

The following are examples of sets of hybridization/wash conditions that may be used to clone homologous nucleotide sequences that are substantially identical to reference nucleotide sequences of the invention or may be used for hybridization conditions for probes and/or primers in amplification assays. In one embodiment, a reference nucleotide sequence hybridizes to the "test" nucleotide sequence in 7% sodium dodecyl sulfate (SDS), 0.5 M $NaPO_4$, 1 mM EDTA at 50° C. with washing in 2×SSC, 0.1% SDS at 50° C. In another embodiment, the reference nucleotide sequence hybridizes to the "test" nucleotide sequence in 7% sodium dodecyl sulfate (SDS), 0.5 M $NaPO_4$, 1 mM EDTA at 50° C. with washing in 1×SSC, 0.1% SDS at 50° C. or in 7% sodium dodecyl sulfate (SDS), 0.5 M $NaPO_4$, 1 mM EDTA at 50° C. with washing in 0.5×SSC, 0.1% SDS at 50° C. In still further embodiments, the reference nucleotide sequence hybridizes to the "test" nucleotide sequence in 7% sodium dodecyl sulfate (SDS), 0.5 M $NaPO_4$, 1 mM EDTA at 50° C. with washing in 0.1×SSC, 0.1% SDS at 50° C., or in 7% sodium dodecyl sulfate (SDS), 0.5 M $NaPO_4$, 1 mM EDTA at 50° C. with washing in 0.1×SSC, 0.1% SDS at 65° C.

A "promoter" is a nucleotide sequence that controls or regulates the transcription of a nucleotide sequence (i.e., a coding sequence) that is operably associated with the promoter. The coding sequence may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. The promoter region may comprise other elements that act as regulators of gene expression. These include a TATA box consensus sequence, and often a CAAT box consensus sequence (Breathnach and Chambon, (1981)

*Annu. Rev. Biochem.* 50:349). Any promoter useful for initiation of transcription in a cell of a plant can be used in the expression cassettes of the present invention. Promoters can include, for example, constitutive, inducible, temporally regulated, developmentally regulated, chemically regulated, tissue-preferred and/or tissue-specific promoters for use in the preparation of recombinant nucleic acid molecules, i.e., "chimeric genes" or "chimeric polynucleotides." In particular aspects, a "promoter" useful with the invention is a promoter capable of initiating transcription of a nucleotide sequence in a cell of interest. The choice of promoter will vary depending on the temporal and spatial requirements for expression, and also depending on the host cell to be transformed. A promoter can be identified in and isolated from the organism to be transformed and then inserted into the nucleic acid construct to be used in transformation of the organism.

Non-limiting examples of a promoter include the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. *Plant Cell Rep.* 23:727-735 (2005); Li et al. *Gene* 403:132-142 (2007); Li et al. *Mol Biol. Rep.* 37:1143-1154 (2010)). PrbcS1 and Pactin are constitutive promoters and Pnr and Pdca1 are inducible promoters. Pnr is induced by nitrate and repressed by ammonium (Li et al. *Gene* 403:132-142 (2007)) and Pdca1 is induced by salt (Li et al. *Mol Biol. Rep.* 37:1143-1154 (2010)).

Examples of constitutive promoters useful for plants include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) *Nature* 313:810-812), CaMV 19S promoter (Lawton et al. (1987) *Plant Mol. Biol.* 9:315-324), nos promoter (Ebert et al. (1987) *Proc. Natl. Acad. Sci USA* 84:5745-5749), Adh promoter (Walker et al. (1987) *Proc. Natl. Acad. Sci. USA* 84:6624-6629), sucrose synthase promoter (Yang & Russell (1990) *Proc. Natl. Acad. Sci. USA* 87:4144-4148), the 35S promoter and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79: 87-94), maize (Christensen et al., 1989. *Plant Molec. Biol.* 12: 619-632), and *arabidopsis* (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the nucleotide sequences of the invention in transgenic plants, especially monocotyledons. Further, the promoter expression cassettes described by McElroy et al. (*Mol. Gen. Genet.* 231: 150-160 (1991)) can be easily modified for the expression of the nucleotide sequences of the invention and are particularly suitable for use in monocotyledonous hosts.

In some embodiments, a recombinant nucleic acid construct of the invention can be an "expression cassette" or can be comprised within an expression cassette. As used herein, "expression cassette" means a recombinant nucleic acid molecule comprising a nucleotide sequence of interest (e.g., a nucleotide sequence of any one of SEQ ID NOs:1-52, or a complement thereof, a nucleotide sequence having at least about 80% identity to of any of SEQ ID NOs:1-52, or a complement thereof; a fragment thereof; or any combination thereof), wherein said nucleotide sequence is operably associated with at least one control sequence (e.g., a promoter). Thus, some embodiments of the invention provide expression cassettes designed to express the nucleotides sequences of the invention in a cell.

An expression cassette comprising a nucleotide sequence of interest may be chimeric, meaning that at least one of its components is heterologous with respect to at least one of its other components. An expression cassette may also be one that is naturally occurring but has been obtained in a recombinant form useful for heterologous expression.

An expression cassette also can optionally include a transcriptional and/or translational termination region (i.e., termination region) that is functional in the cell in which the nucleotide sequence of interest is to be expressed. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the host organism, or may be derived from another source (i.e., foreign or heterologous to the promoter, the nucleotide sequence of interest, the host organism, or any combination thereof). In addition, in some embodiments, a coding sequence's native transcription terminator can be used.

An expression cassette of the invention also can include a nucleotide sequence for a selectable marker, which can be used to select a transformed organism and/or cell. As used herein, "selectable marker" means a nucleotide sequence that when expressed imparts a distinct phenotype to the transformed organism or cell expressing the marker and thus allows such transformed organisms or cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening. Of course, many examples of suitable selectable markers useful in various organisms are known in the art and can be used in the expression cassettes described herein.

In addition to expression cassettes, the nucleic acid molecules and nucleotide sequences described herein can be used in connection with vectors. The term "vector" refers to a composition for transferring, delivering or introducing a nucleic acid (or nucleic acids) into a cell. A vector comprises a nucleic acid molecule comprising the nucleotide sequence(s) to be transferred, delivered or introduced. Vectors for use in transformation of plants and other organisms are well known in the art. Non-limiting examples of general classes of vectors include a viral vector including but not limited to a plasmid vector, a phage vector, a phagemid vector, a cosmid vector, a fosmid vector, a bacteriophage, an artificial chromosome, or an *Agrobacterium* binary vector in double or single stranded linear or circular form which may or may not be self transmissible or mobilizable. A vector as defined herein can transform prokaryotic or eukaryotic host either by integration into the cellular genome or exist extrachromosomally (e.g. autonomous replicating plasmid with an origin of replication). Additionally included are shuttle vectors by which is meant a DNA vehicle capable, naturally or by design, of replication in two different host organisms, which may be selected from prokaryotic and eukaryotic organisms. In some representative embodiments, the nucleic acid in the vector is under the control of, and operably linked to, an appropriate promoter or other regulatory elements for transcription in a host cell such as a microbial, e.g. bacterial, or a plant cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell.

The inventors have discovered nucleotide sequences and the polypeptides encoded by these nucleotide sequences that may be useful for diagnosing a *Pseudoperonospora cubensis* infection in a cucurbit plant, and for distinguishing *P. cubensis* from *Pseudoperonospora humuli*, as well as for distinguishing between different types of *P. cubensis*. As understood in the art, downy mildew pathogens including *P. cubensis* can be spread by seed and other contaminated plant material. Further, downy mildew pathogens can spread for miles by wind. Thus, when an outbreak of *P. cubensis* occurs in a first region, a second region that is downwind may be at risk for an outbreak too. Environmental and plant samples in the second region may be tested to evaluate the risk that an outbreak will occur in that region. Typically, the samples are evaluated by manual counting of the spores. The present invention provides a substantial advantage over the prior art by providing more sensitive and efficient methods for detecting *P. cubensis*, and for distinguishing between *P. cubensis* and *P. humuli* infections and between types of *P. cubensis* that infect cucumber and cantaloupe and types that infect pumpkin, watermelon, and squash.

Accordingly, the present invention provides an isolated nucleic acid molecule is provided comprising: (a) a nucleotide sequence of any one of SEQ ID NOs:1-52, or a complement thereof; (b) a nucleotide sequence having at least about 80% sequence identity to the nucleotide sequence of (a); (c) a nucleotide sequence which anneals under stringent hybridization conditions to the nucleotide sequence of any of (a) and/or (b), or a complement thereof; (d) a nucleotide sequence that differs from the nucleotide sequence of any of (a) to (c) above due to the degeneracy of the genetic code; and (e) a fragment of a nucleotide sequence of any of (a) to (d) above. In some embodiments, the invention provides a recombinant nucleic acid construct comprising at least one isolated nucleic acid molecule of the invention. In some embodiments, the isolated nucleic acid molecule may be operatively linked to a heterologous promoter. These isolated nucleic acids may be used as diagnostic markers for the presence of *P. cubensis*, and for distinguishing between *P. cubensis* and *P. humuli* infections and between types of *P. cubensis* that infect cucumber and cantaloupe and types that infect pumpkin, watermelon, and squash.

In some embodiments, an isolated polypeptide is provided comprising: (a) an amino acid sequence encoded by a nucleotide sequence of any one of SEQ ID NOs:1-52, or a complement thereof; and (b) an amino acid sequence having at least about 80% sequence identity to the amino acid sequence of (a); and a fragment of any of (a) and/or (b). In some embodiments, a polyclonal and/or monoclonal antibody is provided that is specifically reactive with an isolated polypeptide of the invention. Methods for making polyclonal or monoclonal antibodies are well-known in the art. Similarly to the isolated nucleic acids of the invention, the polypeptides encoded by the isolated nucleic acids of the invention and the polyclonal and/or monoclonal antibodies that are specifically reactive with an isolated polypeptide of the invention may be used as diagnostic markers for the presence of *P. cubensis*, and for distinguishing between *P. cubensis* and *P. humuli* infections and between the type of *P. cubensis* that infect cucumber and cantaloupe and the type that infect pumpkin, watermelon, and squash.

Accordingly, in some embodiments, the invention provides a method of diagnosing a *Pseudoperonospora cubensis* infection in a cucurbit plant, comprising detecting at least one polynucleotide selected from the group of nucleotide sequences of SEQ ID NOs:1-52, or a fragment thereof, in a sample from the cucurbit plant, thereby diagnosing a *P. cubensis* infection.

In some embodiments, a method of diagnosing a *Pseudoperonospora cubensis* infection in a cucurbit plant is provided, comprising: contacting a sample from the cucurbit plant with an oligonucleotide that hybridizes to a polynucleotide comprising, consisting essentially of or consisting of any one of the nucleotide sequences of SEQ ID NOs:1-52, or a fragment thereof; and detecting binding between the oligonucleotide and the polynucleotide, thereby diagnosing a *P. cubensis* infection.

A further embodiment provides a method of diagnosing a *Pseudoperonospora cubensis* infection in a cucurbit plant, comprising: contacting a sample from the cucurbit plant with a pair of oligonucleotides that hybridize to a polynucleotide comprising, consisting essentially of or consisting of any one of the nucleotide sequences of SEQ ID NOs:1-52, or a fragment thereof, under conditions whereby nucleic acid amplification can occur, thereby producing an amplification product; and detecting the amplification product, wherein the presence of the amplification product identifies the presence of *P. cubensis*, thereby diagnosing the cucurbit plant as having a *P. cubensis* infection. In some embodiments, detecting whether the polynucleotide, or fragment thereof, is present comprises detecting binding between the amplification product and an oligonucleotide probe that hybridizes to the polynucleotide, or fragment thereof.

In some embodiments, a method of diagnosing an infection in a cucurbit plant by a type of *Pseudoperonospora cubensis* that infects cucumber and cantaloupe is provided, comprising: contacting a sample from the cucurbit plant with an oligonucleotide that hybridizes to the nucleotide sequence of SEQ ID NO:16, and/or a fragment thereof, but does not hybridize to the nucleotide sequence of SEQ ID NO:52, and/or a fragment thereof; and detecting whether the nucleotide sequence of SEQ ID NO:16 and/or fragment thereof is present by detecting binding between the oligonucleotide and the nucleotide sequence of SEQ ID NO:16, and/or fragment thereof, wherein the presence of binding between the oligonucleotide and the nucleotide sequence of SEQ ID NO:16, and/or fragment thereof, identifies the *P. cubensis* as a type that infects cucumber and cantaloupe, thereby diagnosing an infection by the type of *P. cubensis* that infects cucumber and cantaloupe.

In some embodiments, a method of diagnosing an infection in a cucurbit plant by a type of *Pseudoperonospora cubensis* that infects pumpkin, watermelon, and squash is provided, comprising: contacting a sample from the cucurbit plant with an oligonucleotide that hybridizes to the nucleotide sequence of SEQ ID NO:52, and/or a fragment thereof, but does not hybridize to the nucleotide sequence of SEQ ID NO:16, and/or a fragment thereof; and detecting whether the nucleotide sequence of SEQ ID NO:52 and/or fragment thereof is present by detecting binding between the oligonucleotide and the nucleotide sequence of SEQ ID NO:52, and/or fragment thereof, wherein the presence of binding between the oligonucleotide and the nucleotide sequence of SEQ ID NO:52, and/or fragment thereof, identifies the *P. cubensis* as a type that infects cucumber and cantaloupe, thereby diagnosing an infection by the type of *P. cubensis* that infects pumpkin, watermelon, and squash.

In some embodiments, a method of diagnosing an infection in a cucurbit plant by a type of *Pseudoperonospora cubensis* that infects cucumber and cantaloupe is provided, comprising: contacting a sample from the cucurbit plant with a pair of oligonucleotides that hybridize to the nucleotide sequence of SEQ ID NO:16, and/or a fragment thereof, under conditions whereby nucleic acid amplification can occur, thereby producing an amplification product; and detecting whether the nucleotide sequence of SEQ ID NO:16, and/or fragment thereof, is present by detecting binding between the amplification product and an oligonucleotide probe that hybridizes to the nucleotide sequence of SEQ ID NO:16, and/or a fragment thereof, but does not hybridize to the nucleotide sequence of SEQ ID NO:52, and/or a fragment thereof, wherein the presence of the amplification product identifies the *P. cubensis* as the type that infects cucumber and cantaloupe, thereby diagnosing the infection of the cucurbit plant as being by a type of *P. cubensis* that infects cucumber and cantaloupe.

In some embodiments, the invention provides a method of diagnosing an infection in a cucurbit plant by a type of *Pseudoperonospora cubensis* that infects pumpkin, watermelon, and squash, comprising: contacting a sample from the cucurbit plant with a pair of oligonucleotides that hybridize to the nucleotide sequence of SEQ ID NO:52, and/or a fragment thereof, under conditions whereby nucleic acid amplification can occur, thereby producing an amplification product; and detecting whether the nucleotide sequence of SEQ ID NO:52, and/or fragment thereof, is present by detecting binding between the amplification product and an oligonucleotide probe that hybridizes to the nucleotide sequence of SEQ ID NO:52, and/or a fragment thereof, but does not hybridize to the nucleotide sequence of SEQ ID NO:16, and/or a fragment thereof, wherein the presence of the amplification product identifies the *P. cubensis* as the type that infects cucumber and cantaloupe, thereby diagnosing the infection of the cucurbit plant as being by a type of *P. cubensis* that infects cucumber and cantaloupe.

In some embodiments, a method of diagnosing an infection in a cucurbit plant by a type of *Pseudoperonospora cubensis* that infects cucumber and cantaloupe (type 2) or by a type of *P. cubensis* that infects pumpkin, watermelon, and squash (type 1) is provided, comprising: contacting a sample from a cucurbit plant with a first oligonucleotide that hybridizes to the nucleotide sequence of SEQ ID NO:16, and/or a fragment thereof, but does not hybridize to the nucleotide sequence of SEQ ID NO:52, and/or a fragment thereof, and a second oligonucleotide that hybridizes to the nucleotide sequence of SEQ ID NO:52, and/or a fragment thereof, but does not hybridize to the nucleotide sequence of SEQ ID NO:16, and/or a fragment thereof; and detecting whether the nucleotide sequence of SEQ ID NO:16 and/or fragment thereof is present by detecting binding between the first oligonucleotide and the nucleotide sequence of SEQ ID NO:16, and/or fragment thereof, and/or whether the nucleotide sequence of SEQ ID NO:52, and/or fragment thereof, is present by detecting binding between the second oligonucleotide and the nucleotide sequence of SEQ ID NO:52, and/or fragment thereof, wherein the presence of binding between the first oligonucleotide and the nucleotide sequence of SEQ ID NO:16, and/or fragment thereof, identifies the *P. cubensis* as a type that infects cucumber and cantaloupe, thereby diagnosing an infection by the type of *P. cubensis* that infects cucumber and cantaloupe, and the presence of binding between the second oligonucleotide and the nucleotide sequence of SEQ ID NO:52, and/or fragment thereof, identifies the *P. cubensis* as a type that infects pumpkin, watermelon, and squash, thereby diagnosing an infection by a type of *P. cubensis* that infects pumpkin, watermelon, and squash.

In further embodiments, a method of diagnosing an infection in a cucurbit plant by a type of *Pseudoperonospora cubensis* that infects cucumber and cantaloupe or, by a type of *P. cubensis* that infects pumpkin, watermelon, and squash is provided, comprising: contacting a sample from a cucurbit plant suspected of being infected with *P. cubensis* with a pair of oligonucleotides that hybridize to the nucleotide sequence of SEQ ID NO:16, and/or a fragment thereof, and to the nucleotide sequence of SEQ ID NO:52, and/or a fragment thereof, under conditions whereby nucleic acid amplification can occur, thereby producing an amplification product; and detecting whether the nucleotide sequence of SEQ ID NO:16, and/or fragment thereof, is present by detecting binding between the amplification product and a first oligonucleotide probe that hybridizes to the nucleotide sequence of SEQ ID NO:16, and/or a fragment thereof, but does not hybridize to the nucleotide sequence of SEQ ID NO:52, and/or a fragment thereof, and/or whether the nucleotide sequence of SEQ ID NO:52, and/or a fragment thereof, is present by detecting binding between the amplification product and a second oligonucleotide probe that hybridizes to the nucleotide sequence of SEQ ID NO:52, and/or a fragment thereof, but does not hybridize to the nucleotide sequence of SEQ ID NO:16, and/or a fragment thereof, wherein the presence of binding between the first oligonucleotide probe and the amplification product identifies the *P. cubensis* as the type that infects cucumber and cantaloupe, thereby diagnosing the infection of the cucurbit plant as being by a type of *P. cubensis* that infects cucumber and cantaloupe, and the presence of binding between the second oligonucleotide probe and the amplification product identifies the *P. cubensis* as a type that infects pumpkin, watermelon, and squash, thereby diagnosing an infection by a type of *P. cubensis* that infects pumpkin, watermelon, and squash.

In some embodiments, a method for determining a risk of a *Pseudoperonospora cubensis* outbreak is provided, comprising: detecting at least one polynucleotide comprising, consisting essentially of or consisting of any one of the nucleotide sequences of SEQ ID NOs:1-52, or a fragment thereof, in a sample from a plant or in an environmental sample, wherein the presence of the at least one polynucleotide indicates the presence of *P. cubensis* and the risk of a *P. cubensis* outbreak A further embodiment of the invention provides a method for determining a risk of a *Pseudoperonospora cubensis* outbreak, comprising: contacting a sample from a plant or an environmental sample with an oligonucleotide that hybridizes to a polynucleotide comprising, consisting essentially of or consisting of any one of the nucleotide sequences of SEQ ID NOs:1-52, or a fragment thereof; and detecting binding between the oligonucleotide and the polynucleotide, wherein the presence of the polynucleotide or fragment thereof, indicates the presence of *P. cubensis* and the risk of a *P. cubensis* outbreak.

Some embodiments of the invention provide a method for determining a risk of a *Pseudoperonospora cubensis* outbreak, comprising:

contacting a sample from a cucurbit plant or an environmental sample with a pair of oligonucleotides that hybridize to a polynucleotide comprising, consisting essentially of or consisting of any one of the nucleotide sequences of SEQ ID NOs:1-52, or a fragment thereof, under conditions whereby nucleic acid amplification can occur, thereby producing an amplification product; and detecting the amplification product, wherein the presence of the amplification product identifies the presence of *P. cubensis* and the risk of a *P. cubensis* outbreak. In some embodiments, detecting whether the polynucleotide and/or fragment thereof is present comprises detecting binding between the amplification product and an oligonucleotide probe that hybridizes to the polynucleotide, and/or fragment thereof.

In some embodiments, a method for determining a risk of a *Pseudoperonospora cubensis* outbreak by a type of *P. cubensis* that infects cucumber and cantaloupe is provided, comprising: contacting a sample from a plant or an environmental sample with an oligonucleotide that hybridizes to the nucleotide sequence of SEQ ID NO:16, and/or a fragment thereof, but does not hybridize to the nucleotide sequence of SEQ ID NO:52, and/or a fragment thereof, and detecting whether the nucleotide sequence of SEQ ID NO:16 and/or the fragment thereof is present by detecting binding between the oligonucleotide and the nucleotide sequence of SEQ ID NO:16, and/or fragment thereof, wherein the presence of binding between the oligonucleotide and the nucleotide sequence of SEQ ID NO:16, and/or fragment thereof, indicates the presence of the type of *P. cubensis* that infects cucumber and cantaloupe and the risk of a *P. cubensis* outbreak by the type of *P. cubensis* that infects cucumber and cantaloupe In some embodiments, a method for determining a risk of a *Pseudoperonospora cubensis* outbreak by a type of *P. cubensis* that infects pumpkin, watermelon, and squash is provided, comprising: contacting a sample from a plant or an environmental sample with an oligonucleotide that hybridizes to the nucleotide sequence of SEQ ID NO:52, and/or a fragment thereof, but does not hybridize to the nucleotide sequence of SEQ ID NO:16, and/or a fragment thereof, and detecting whether the nucleotide sequence of SEQ ID NO:52 and/or the fragment thereof is present by detecting binding between the oligonucleotide and the nucleotide sequence of SEQ ID NO:52, and/or fragment thereof, wherein the presence of binding between the oligonucleotide and the nucleotide sequence of SEQ ID NO:52, and/or fragment thereof, indicates the presence of the type of *P. cubensis* that infects pumpkin, watermelon, and squash and the risk of a *P. cubensis* outbreak by the type of *P. cubensis* that infects pumpkin, watermelon, and squash.

In some embodiments, a method for determining a risk of a *Pseudoperonospora cubensis* outbreak by a type of *P. cubensis* that infects cucumber and cantaloupe is provided, comprising: contacting a sample from a plant or an environmental sample with a pair of oligonucleotides that hybridize to the nucleotide sequence of SEQ ID NO:16, and/or a fragment thereof, under conditions whereby nucleic acid amplification can occur, thereby producing an amplification product; and detecting whether the nucleotide sequence of SEQ ID NO:16, and/or fragment thereof, is present by detecting binding between the amplification product and an oligonucleotide probe that hybridizes to the nucleotide sequence of SEQ ID NO:16, and/or a fragment thereof, but does not hybridize to the nucleotide sequence of SEQ ID NO:52, and/or a fragment thereof, wherein the presence of binding between the oligonucleotide probe and the amplification product indicates the presence of the type of *P. cubensis* that infects cucumber and cantaloupe and the risk of a *P. cubensis* outbreak by the type of *P. cubensis* that infects cucumber and cantaloupe.

In some embodiments, a method for determining a risk of a *Pseudoperonospora cubensis* outbreak by a type of *P. cubensis* that infects pumpkin, watermelon, and squash is provided, comprising: contacting a sample from a plant or an environmental sample with a pair of oligonucleotides that hybridize to the nucleotide sequence of SEQ ID NO:52, and/or a fragment thereof, under conditions whereby nucleic acid amplification can occur, thereby producing an amplification product; and detecting whether the nucleotide sequence of SEQ ID NO:52, and/or a fragment thereof, is present by detecting binding between the amplification product and an oligonucleotide probe that hybridizes to the nucleotide sequence of SEQ ID NO:52, and/or a fragment thereof, but does not hybridize to the nucleotide sequence of SEQ ID NO:16, and/or a fragment thereof, wherein the presence of binding between the oligonucleotide probe and the amplification product indicates the presence of the type of *P. cubensis* that infects pumpkin, watermelon, and squash and the risk of a *P. cubensis* outbreak by the type of *P. cubensis* that infects pumpkin, watermelon, and squash.

A further embodiment provides a method for determining a risk of a *Pseudoperonospora cubensis* outbreak by a type of *P. cubensis* that infects cucumber and cantaloupe or by a type of *P. cubensis* that infects pumpkin, watermelon, and squash, comprising: contacting a sample from a plant or an environmental sample with a first oligonucleotide that hybridizes to the nucleotide sequence of SEQ ID NO:16, and/or a fragment thereof, but does not hybridize to the nucleotide sequence of SEQ ID NO:52, and/or a fragment thereof, and a second oligonucleotide that hybridizes to the nucleotide sequence of SEQ ID NO:52, and/or a fragment thereof, but does not hybridize to the nucleotide sequence of SEQ ID NO:16, and/or a fragment thereof; and detecting whether the nucleotide sequence of SEQ ID NO:16 and/or fragment thereof is present by detecting binding between the first oligonucleotide and the nucleotide sequence of SEQ ID NO:16, and/or fragment thereof, and/or whether the nucleotide sequence of SEQ ID NO:52, and/or fragment thereof, is present by detecting binding between the second oligonucleotide and the nucleotide sequence of SEQ ID NO:52, and/or fragment thereof, wherein the presence of binding between the first oligonucleotide and the nucleotide sequence of SEQ ID NO:16, and/or fragment thereof, indicates the presence of the type of *P. cubensis* that infects cucumber and cantaloupe and a risk of a *P. cubensis* outbreak by the type of *P. cubensis* that infects cucumber and cantaloupe, and the presence of binding between the second oligonucleotide and the nucleotide sequence of SEQ ID NO:52, and/or fragment thereof, indicates the presence of the type of *P. cubensis* that infects pumpkin, watermelon, and squash and a risk of a *P. cubensis* outbreak by the type of *P. cubensis* that infects pumpkin, watermelon, and squash.

A further embodiment provides a method for determining a risk of a *Pseudoperonospora cubensis* outbreak by a type of *P. cubensis* that infects cucumber and cantaloupe or by a type of *P. cubensis* that infects pumpkin, watermelon, and squash, comprising: contacting a sample from a plant or an environmental sample with a pair of oligonucleotides that hybridize to the nucleotide sequence of SEQ ID NO:16, and/or a fragment thereof, and to the nucleotide sequence of SEQ ID NO:52, and/or a fragment thereof, under conditions whereby nucleic acid amplification can occur, thereby producing an amplification product; and detecting whether the nucleotide sequence of SEQ ID NO:16, and/or fragment thereof, is present by detecting binding between the amplification product and a first oligonucleotide probe that hybridizes to the nucleotide sequence of SEQ ID NO:16, and/or a fragment thereof, but does not hybridize to the nucleotide sequence of SEQ ID NO:52, and/or a fragment thereof, and/or whether the nucleotide sequence of SEQ ID NO:52, and/or a fragment thereof, is present by detecting binding between the amplification product and a second oligonucleotide probe that hybridizes to the nucleotide sequence of SEQ ID NO:52, and/or a fragment thereof, but does not hybridize to the nucleotide sequence of SEQ ID NO:16, and/or a fragment thereof, wherein the presence of binding between the first oligonucleotide probe and the amplification product indicates the presence of the type of *P. cubensis* that infects cucumber and cantaloupe and a risk of a *P. cubensis* outbreak by the type of *P. cubensis* that infects cucumber and cantaloupe, and the presence of binding between the second oligonucleotide probe and the amplification product indicates the presence of the type of *P. cubensis* that infects pumpkin, watermelon, and squash and a risk of a *P. cubensis* outbreak by the type of *P. cubensis* that infects pumpkin, watermelon, and squash.

In some embodiments, the sample may be taken from a region suspected of being at risk for an outbreak of infection by *P. cubensis*, or from a neighboring region. A region may be determined to be at risk for an outbreak by the detection of at least one of the nucleotide sequences of SEQ ID NOs:1-52 or a fragment thereof.

In additional embodiments, a method of selecting a treatment regimen for a *P. cubensis* infection is provided, comprising: detecting in a sample from the plant at least one polynucleotide selected from the group of nucleotide sequences of SEQ ID NOs:1-52, and/or a fragment thereof, thereby identifying a *P. cubensis* infection; and selecting a treatment regimen for the *P. cubensis* infection.

A further embodiment provides a method of selecting a treatment regimen for a *P. cubensis* infection, comprising: contacting a sample from the plant with an oligonucleotide that hybridizes to a polynucleotide selected from the group of nucleotide sequences of SEQ ID NOs:1-52, and/or a fragment thereof; detecting binding between the oligonucleotide and the nucleotide sequence, thereby identifying a *P. cubensis* infection; and selecting a treatment regimen for the *P. cubensis* infection.

In some embodiments, a method of selecting a treatment regimen for a *P. cubensis* infection is provided, comprising: contacting a sample from the cucurbit plant with a pair of oligonucleotides that hybridize a polynucleotide selected from the group of nucleotide sequences of SEQ ID NOs:1-52, and/or a fragment thereof, under conditions whereby nucleic acid amplification can occur, thereby producing an amplification product; and detecting the amplification product, wherein the presence of the amplification product identifies the presence of *P. cubensis*, thereby identifying a *P. cubensis* infection; and selecting a treatment regimen for the *P. cubensis* infection. In some embodiments, detecting whether the polynucleotide and/or fragment thereof is present comprises detecting binding between the amplification product and an oligonucleotide probe that hybridizes to the polynucleotide, and/or fragment thereof.

In some embodiments, a method of selecting a treatment regimen for an infection in a cucurbit plant by a type of *P. cubensis* that infects cucumber and cantaloupe is provided, comprising: contacting a sample from the cucurbit plant with an oligonucleotide that hybridizes to the nucleotide sequence of SEQ ID NO:16, and/or a fragment thereof, but does not hybridize to the nucleotide sequence of SEQ ID NO:52; and detecting whether the nucleotide sequence of SEQ ID NO:16, and/or fragment thereof, is present by detecting binding between the oligonucleotide and the nucleotide sequence of SEQ ID NO:16, and/or fragment thereof, wherein the presence of binding between the oligonucleotide and the nucleotide sequence of SEQ ID NO:16, and/or fragment thereof, identifies the *P. cubensis* as a type that infects cucumber and cantaloupe; and selecting a treatment regimen effective against the type of *P. cubensis* that infects cucumber and cantaloupe.

In some embodiments, a method of selecting a treatment regimen for an infection in a cucurbit plant by a type of *P. cubensis* that infects pumpkin, watermelon, and squash is provided, comprising: contacting a sample from the cucurbit plant with an oligonucleotide that hybridizes to the nucleotide sequence of SEQ ID NO:52, and/or a fragment thereof, but does not hybridize to the nucleotide sequence of SEQ ID NO:16; and detecting whether the nucleotide sequence of SEQ ID NO:52, and/or fragment thereof, is present by detecting binding between the oligonucleotide and the nucleotide sequence of SEQ ID NO:52, and/or fragment thereof, wherein the presence of binding between the oligonucleotide and the nucleotide sequence of SEQ ID NO:52, and/or fragment thereof, identifies the *P. cubensis* as a type that infects pumpkin, watermelon, and squash; and selecting a treatment regimen effective against the type of *P. cubensis* that infects pumpkin, watermelon, and squash.

In some embodiments, a method of selecting a treatment regimen for an infection in a cucurbit plant by a type of *P. cubensis* that infects cucumber and cantaloupe is provided, comprising: contacting a sample from the cucurbit plant with a pair of oligonucleotides that hybridize to the nucleotide sequence of SEQ ID NO:16, and/or a fragment thereof, under conditions whereby nucleic acid amplification can occur, thereby producing an amplification product; and detecting whether the nucleotide sequence of SEQ ID NO:16, and/or fragment thereof, is present by detecting binding between the amplification product and an oligonucleotide probe that hybridizes to the nucleotide sequence of SEQ ID NO:16, and/or a fragment thereof, but does not hybridize to the nucleotide sequence of SEQ ID NO:52, and/or a fragment thereof, wherein the presence of binding between the oligonucleotide probe and the amplification product identifies the *P. cubensis* as the type that infects cucumber and cantaloupe; and selecting a treatment regimen effective against the type of *P. cubensis* that infects cucumber and cantaloupe.

In some embodiments, a method of selecting a treatment regimen for an infection in a cucurbit plant by a type of *P. cubensis* that infects pumpkin, watermelon, and squash is provided, comprising: contacting a sample from a cucurbit plant with a pair of oligonucleotides that hybridize to the nucleotide sequence of SEQ ID NO:52, and/or a fragment thereof, under conditions whereby nucleic acid amplification can occur, thereby producing an amplification product; and detecting whether the nucleotide sequence of SEQ ID NO:52, and/or a fragment thereof, is present by detecting binding between the amplification product and an oligonucleotide probe that hybridizes to the nucleotide sequence of SEQ ID NO:52, and/or a fragment thereof, but does not hybridize to the nucleotide sequence of SEQ ID NO:16, and/or a fragment thereof, wherein the presence of binding between the oligonucleotide probe and the amplification product identifies the *P. cubensis* as the type that infects pumpkin, watermelon, and squash; and selecting a treatment regimen effective against the type of *P. cubensis* that infects pumpkin, watermelon, and squash.

In further embodiments, a method of selecting a treatment regimen for an infection in a cucurbit plant by a type of *P. cubensis* that infects cucumber and cantaloupe or for a type of *P. cubensis* that infects pumpkin, watermelon, and squash is provided, comprising: contacting a sample from a cucurbit plant suspected of being infected with *P. cubensis* with a first oligonucleotide that hybridizes to the nucleotide sequence of SEQ ID NO:16, and/or a fragment thereof, but does not hybridize to the nucleotide sequence of SEQ ID NO:52, and/or a fragment thereof, and a second oligonucleotide that hybridizes to the nucleotide sequence of SEQ ID NO:52, and/or a fragment thereof, but does not hybridize to the nucleotide sequence of SEQ ID NO:16, and/or a fragment thereof; and detecting whether the nucleotide sequence of SEQ ID NO:16, and/or fragment thereof, is present by detecting binding between the first oligonucleotide and the nucleotide sequence of SEQ ID NO:16, and/or fragment thereof, and/or whether the nucleotide sequence of SEQ ID NO:52, and/or fragment thereof, is present by detecting binding between the second oligonucleotide and the nucleotide sequence of SEQ ID NO:52, and/or fragment thereof, wherein the presence of binding between the first oligonucleotide and the nucleotide sequence of SEQ ID NO:16, and/or fragment thereof, identifies the *P. cubensis* as a type that infects cucumber and cantaloupe, and the presence of binding between the oligonucleotide and the nucleotide sequence of SEQ ID NO:52, and/or fragment thereof, identifies the *P. cubensis* as a type that infects pumpkin, watermelon, and squash; and selecting a treatment regimen effective against the type of *P. cubensis* identified.

In a further embodiment, a method of selecting a treatment regimen for an infection in a cucurbit plant by a type of *P. cubensis* that infects cucumber and cantaloupe or for a type of *P. cubensis* that infects pumpkin, watermelon, and squash is provided, comprising: contacting a sample from a cucurbit plant suspected of being infected with *P. cubensis* with a pair of oligonucleotides that hybridize to the nucleotide sequence of SEQ ID NO:16, and/or a fragment thereof, and to the nucleotide sequence of SEQ ID NO:52, and/or a fragment thereof, under conditions whereby nucleic acid amplification can occur, thereby producing an amplification product; and detecting whether the nucleotide sequence of SEQ ID NO:16, and/or fragment thereof, is present by detecting binding between the amplification product and a first oligonucleotide probe that hybridizes to the nucleotide sequence of SEQ ID NO:16, and/or a fragment thereof, but does not hybridize to the nucleotide sequence of SEQ ID NO:52, and/or a fragment thereof, and/or whether the nucleotide sequence of SEQ ID NO:52, and/or a fragment thereof, is present by detecting binding between the amplification product and a second oligonucleotide probe that hybridizes to the nucleotide sequence of SEQ ID NO:52, and/or a fragment thereof, but does not hybridize to the nucleotide sequence of SEQ ID NO:16, and/or a fragment thereof, wherein the presence of binding between the first oligonucleotide probe and the amplification product identifies the *P. cubensis* as the type that infects cucumber and cantaloupe, and the presence of binding between the second oligonucleotide probe and the amplification product identifies the *P. cubensis* as a type that infects pumpkin, watermelon, and squash, selecting a treatment regimen effective against the type of *P. cubensis* identified.

In some embodiments, the invention provides a method for reducing the risk of a *P. cubensis* outbreak is provided, comprising: detecting in a sample from a cucurbit plant or in an environmental sample at least one polynucleotide selected from the group of nucleotide sequences of SEQ ID NOs:1-52 and/or a fragment thereof, thereby identifying the presence of *P. cubensis* in the sample; and implementing a treatment regimen for a *P. cubensis* infection, thereby reducing the risk of a *P. cubensis* outbreak.

An additional embodiment provides a method for reducing the risk of a *P. cubensis* outbreak, comprising: contacting a sample from a cucurbit plant or an environmental sample with an oligonucleotide that hybridizes to a polynucleotide selected from the group of nucleotide sequences of SEQ ID NOs:1-52, or a fragment thereof; detecting binding between the oligonucleotide and the polynucleotide and/or fragment thereof, thereby identifying the presence of *P. cubensis* in the sample; and implementing a treatment regimen for a *P. cubensis* infection, thereby reducing the risk of a *P. cubensis* outbreak.

A further embodiment provides a method for reducing the risk of a *P. cubensis* outbreak, comprising: contacting a sample from a cucurbit plant or an environmental sample with a pair of oligonucleotides that hybridize to a polynucleotide selected from the group of nucleotide sequences of SEQ ID NOs:1-52, or a fragment thereof, under conditions whereby nucleic acid amplification can occur, thereby producing an amplification product; detecting the amplification product, wherein the presence of the amplification product identifies the presence of *P. cubensis*; and implementing a treatment regimen for a *P. cubensis* infection, thereby reducing the risk of a *P. cubensis* outbreak. In some embodiments, detecting whether the polynucleotide and/or fragment thereof is present comprises detecting binding between the amplification product and an oligonucleotide probe that hybridizes to the polynucleotide, and/or fragment thereof.

In some embodiments, a method for reducing the risk of a *Pseudoperonospora cubensis* outbreak by a *P. cubensis* that infects cucumber and cantaloupe is provided, comprising: contacting a sample from a plant or an environmental sample with an oligonucleotide that hybridizes to the nucleotide sequence of SEQ ID NO:16, and/or a fragment thereof, but does not hybridize to the nucleotide sequence of SEQ ID NO:52, and/or a fragment thereof; detecting whether the nucleotide sequence of SEQ ID NO:16, and/or fragment thereof, is present by detecting binding between the oligonucleotide and the nucleotide sequence of SEQ ID NO:16, and/or fragment thereof, wherein the presence of binding between the oligonucleotide and the nucleotide sequence of SEQ ID NO:16 and/or fragment thereof, identifies the *P. cubensis* as a type that infects cucumber and cantaloupe; and implementing a treatment regimen against the type of *P. cubensis* that infects cucumber and cantaloupe, thereby reducing the risk of an outbreak by *P. cubensis* that infects cucumber and cantaloupe.

In some embodiments, a method for reducing the risk of a *Pseudoperonospora cubensis* outbreak by a type of *P. cubensis* that infects pumpkin, watermelon, and squash is provided, comprising: contacting a sample from a plant or an environmental sample with an oligonucleotide that hybridizes to the nucleotide sequence of SEQ ID NO:52, and/or a fragment thereof, but does not hybridize to the nucleotide sequence of SEQ ID NO:16, and/or a fragment thereof; and detecting whether the nucleotide sequence of SEQ ID NO:52, and/or fragment thereof, is present by detecting binding between the oligonucleotide and the nucleotide sequence of SEQ ID NO:52, and/or fragment thereof, wherein the presence of binding between the oligonucleotide and the nucleotide sequence of SEQ ID NO:52, and/or fragment thereof, identifies the *P. cubensis* as a type that infects pumpkin, watermelon, and squash; and implementing a treatment regimen against the type of *P. cubensis* that infects pumpkin, watermelon, and squash, thereby reducing the risk of an outbreak by *P. cubensis* that infects pumpkin, watermelon, and squash.

In some embodiments, a method for reducing the risk of a *P. cubensis* outbreak by a *P. cubensis* that infects cucumber and cantaloupe is provided, comprising: contacting a sample from a plant or an environmental sample with a pair of oligonucleotides that hybridize to the nucleotide sequence of SEQ ID NO:16, and/or a fragment thereof, under conditions whereby nucleic acid amplification can occur, thereby producing an amplification product; detecting whether the nucleotide sequence of SEQ ID NO:16, and/or fragment thereof, is present by detecting binding between the amplification product and an oligonucleotide probe that hybridizes to the nucleotide sequence of SEQ ID NO:16, and/or a fragment thereof, but does not hybridize to the nucleotide sequence of SEQ ID NO:52, and/or a fragment thereof, wherein the presence of binding between the oligonucleotide probe and the amplification product identifies the *P. cubensis* as the type that infects cucumber and cantaloupe; and implementing a treatment regimen against the type of *P. cubensis* that infects cucumber and cantaloupe thereby reducing the risk of an outbreak by *P. cubensis* that infects cucumber and cantaloupe.

In some embodiments, a method for reducing the risk of a *P. cubensis* outbreak by a *P. cubensis* infects pumpkin, watermelon, and squash is provided, comprising: contacting a sample from a plant or an environmental sample with a pair of oligonucleotides that hybridize to the nucleotide sequence of SEQ ID NO:52, and/or a fragment thereof, under conditions whereby nucleic acid amplification can occur, thereby producing an amplification product; detecting whether the nucleotide sequence of SEQ ID NO:52, and/or a fragment thereof, is present by detecting binding between the amplification product and an oligonucleotide probe that hybridizes to the nucleotide sequence of SEQ ID NO:52, and/or a fragment thereof, but does not hybridize to the nucleotide sequence of SEQ ID NO:16, and/or a fragment thereof, wherein the presence of binding between the oligonucleotide probe and the amplification product identifies the *P. cubensis* as the type that infects pumpkin, watermelon, and squash; and implementing a treatment regimen against the type of *P. cubensis* that infects pumpkin, watermelon, and squash, thereby reducing the risk of an outbreak by *P. cubensis* that infects pumpkin, watermelon, and squash.

Another embodiment of the invention provides a method for reducing the risk of a *Pseudoperonospora cubensis* outbreak by a *P. cubensis* that infects cucumber and cantaloupe or by a type of *P. cubensis* that infects pumpkin, watermelon, and squash, comprising: contacting a sample from a plant or an environmental sample with a first oligonucleotide that hybridizes to the nucleotide sequence of SEQ ID NO:16, and/or a fragment thereof, but does not hybridize to the nucleotide sequence of SEQ ID NO:52, and/or a fragment thereof, and a second oligonucleotide that hybridizes to the nucleotide sequence of SEQ ID NO:52, and/or a fragment thereof, but does not hybridize to the nucleotide sequence of SEQ ID NO:16, and/or a fragment thereof; and detecting whether the nucleotide sequence of SEQ ID NO:16, and/or fragment thereof, is present by detecting binding between the first oligonucleotide and the nucleotide sequence of SEQ ID NO:16, and/or fragment thereof, and/or whether the nucleotide sequence of SEQ ID NO:52, and/or fragment thereof, is present by detecting binding between the second oligonucleotide and the nucleotide sequence of SEQ ID NO:52, and/or fragment thereof, wherein the presence of binding between the first oligonucleotide and the nucleotide sequence of SEQ ID NO:16 and/or fragment thereof, identifies the *P. cubensis* as a type that infects cucumber and cantaloupe, and the presence of binding between the second oligonucleotide and the nucleotide sequence of SEQ ID NO:52, and/or fragment thereof, identifies the *P. cubensis* as a type that infects pumpkin, watermelon, and squash; and implementing a treatment regimen against the type of *P. cubensis* that infects cucumber and cantaloupe or against the type of *P. cubensis* that infects pumpkin, watermelon, and squash, thereby reducing the risk of an outbreak by *P. cubensis* that infects cucumber and cantaloupe and/or by the type of *P. cubensis* that infects pumpkin, watermelon, and squash.

In another embodiment, a method for reducing the risk of a *P. cubensis* outbreak by a *P. cubensis* that infects cucumber and cantaloupe, or by a *P. cubensis* that infects pumpkin, watermelon, and squash is provided, comprising: contacting a sample from a plant or an environmental sample with a pair of oligonucleotides that hybridize to the nucleotide sequence of SEQ ID NO:16, and/or a fragment thereof, and to the nucleotide sequence of SEQ ID NO:52, and/or a fragment thereof, under conditions whereby nucleic acid amplification can occur, thereby producing an amplification product; detecting whether the nucleotide sequence of SEQ ID NO:16, and/or fragment thereof, is present by detecting binding between the amplification product and a first oligonucleotide probe that hybridizes to the nucleotide sequence of SEQ ID NO:16, and/or a fragment thereof, but does not hybridize to the nucleotide sequence of SEQ ID NO:52, and/or a fragment thereof, and/or whether the nucleotide sequence of SEQ ID NO:52, and/or a fragment thereof, is present by detecting binding between the amplification product and a second oligonucleotide probe that hybridizes to the nucleotide sequence of SEQ ID NO:52, and/or a fragment thereof, but does not hybridize to the nucleotide sequence of SEQ ID NO:16, and/or a fragment thereof, wherein the presence of binding between the first oligonucleotide probe and the amplification product identifies the *P. cubensis* as the type that infects cucumber and cantaloupe, and the presence of binding between the second oligonucleotide probe and the amplification product identifies the *P. cubensis* as a type that infects pumpkin, watermelon, and squash; and implementing a treatment regimen against the type of *P. cubensis* that infects cucumber and cantaloupe or against the type of *P. cubensis* that infects pumpkin, watermelon, and squash, thereby reducing the risk of an outbreak by *P. cubensis* that infects cucumber and cantaloupe and/or by the type of *P. cubensis* that infects pumpkin, watermelon, and squash.

In representative embodiments, the polynucleotide that is selected for diagnosing a *P. cubensis* infection, determining or reducing the risk of a *P. cubensis* outbreak, and/or selecting a treatment regimen for a *P. cubensis* infection may be the nucleotide sequence of SEQ ID NO:2, SEQ ID NO:13, SEQ ID NO:16, SEQ ID NO:17, SEQ ID NO:24, SEQ ID NO:39, SEQ ID NO:43, SEQ ID NO:52, or a fragment thereof, or any combination thereof.

A further embodiment of the invention provides a method for determining a risk of a *Pseudoperonospora cubensis* outbreak, comprising: contacting a sample from a cucurbit plant or from an environmental sample with an oligonucleotide that hybridizes to an isolated nucleic acid molecule and/or with an antibody of the invention; and detecting whether the isolated nucleic acid molecule, or fragment thereof, is present by detecting binding between the oligonucleotide and the isolated nucleic acid molecule, or fragment thereof, and/or detecting whether a polypeptide encoded by the isolated nucleic acid molecule, or fragment thereof, is present by detecting binding between the antibody and the polypeptide, wherein the presence of the isolated nucleic acid molecule and/or the polypeptide indicates the presence of *P. cubensis* in the sample and the risk of a *P. cubensis* outbreak.

In another embodiment, the invention provides a method for determining a risk of a *Pseudoperonospora cubensis* outbreak, comprising: contacting a sample from a cucurbit plant or an environmental sample with a pair oligonucleotides that hybridize to an isolated nucleic acid molecule of the invention, under conditions whereby nucleic acid amplification can occur, thereby producing an amplification product; detecting the amplification product, wherein the presence of binding between the oligonucleotide probe and the amplification product identifies the presence of *P. cubensis* and the risk of a *P. cubensis* outbreak.

A further embodiment provides a method of selecting a treatment regimen for a *P. cubensis* infection of a cucurbit plant, comprising: contacting a sample from a cucurbit plant suspected of being infected with *P. cubensis* with an oligonucleotide that hybridizes to an isolated nucleic acid molecule and/or with an antibody of the invention;

detecting whether the isolated nucleic acid molecule and/or a fragment thereof is present by detecting binding between the oligonucleotide and the isolated nucleic acid molecule, and/or detecting whether a polypeptide encoded by the isolated nucleic acid molecule and/or a fragment thereof is present by detecting binding between the antibody and the polypeptide, thereby identifying a *P. cubensis* infection when the presence of the isolated nucleic acid molecule and/or polypeptide is detected; and selecting a treatment regimen for the *P. cubensis* infection.

Additionally provided is a method of selecting a treatment regimen for a *P. cubensis* infection of a cucurbit plant, comprising: contacting a sample from a cucurbit plant suspected of being infected with *P. cubensis* with a pair oligonucleotides that hybridize to an isolated nucleic acid molecule of the invention, under conditions whereby nucleic acid amplification can occur, thereby producing an amplification product; detecting the amplification product, wherein the presence of binding between the oligonucleotide probe and the amplification product identifies the presence of *P. cubensis* in the sample; and selecting a treatment regimen for the *P. cubensis* infection.

A further embodiment of the invention provides a method for reducing the risk of a *P. cubensis* outbreak, comprising: contacting a sample from a cucurbit plant or from an environmental sample with an oligonucleotide that hybridizes to an isolated nucleic acid molecule and/or with an antibody of the invention; detecting whether the isolated nucleic acid molecule, and/or a fragment thereof, is present by detecting binding between the oligonucleotide and the isolated nucleic acid molecule, and/or detecting whether a polypeptide encoded by the isolated nucleic acid molecule, and/or a fragment thereof, is present by detecting binding between the antibody and the polypeptide, wherein the presence of the isolated nucleic acid molecule and/or the polypeptide identifies the presence of *P. cubensis*; and implementing a treatment regimen for a *P. cubensis* infection, thereby reducing the risk of a *P. cubensis* outbreak.

A further embodiment of the invention provides a method for reducing the risk of a *P. cubensis* outbreak, comprising: contacting a sample from a cucurbit plant or an environmental sample with a pair oligonucleotides that hybridize to an isolated nucleic acid molecule of the invention, under conditions whereby nucleic acid amplification can occur, thereby producing an amplification product; detecting the amplification product, wherein the presence of the amplification product identifies the presence of *P. cubensis* in the sample; and implementing a treatment regimen for a *P. cubensis* infection, thereby reducing the risk of a *P. cubensis* outbreak.

In a still further embodiment, a method of distinguishing a type of *P. cubensis* that infects cucumber and cantaloupe from a type of *P. cubensis* that infects pumpkin, watermelon, and squash, comprising: contacting a sample from a cucurbit plant or from an environmental sample with a first oligonucleotide that hybridizes to the nucleotide sequence of SEQ ID NO:16 and/or a fragment thereof, but not to the nucleotide sequence of SEQ ID NO:52, and/or fragment thereof, and/or a second oligonucleotide that hybridizes to the nucleotide sequence of SEQ ID NO:52, and/or a fragment thereof, but not to the nucleotide sequence of SEQ ID NO:52, and/or fragment thereof; detecting whether the nucleotide sequence of SEQ ID NO:16, and/or fragment thereof, is present by detecting binding between the first oligonucleotide and the nucleotide sequence of SEQ ID NO:16, and/or fragment thereof, and/or whether the nucleotide sequence of SEQ ID NO:52, and/or fragment thereof, is present by detecting binding between the second oligonucleotide and the nucleotide sequence of SEQ ID NO:52, and/or fragment thereof; and identifying a type of *P. cubensis* that infects cucumber and cantaloupe when binding is detected between the first oligonucleotide and the nucleotide sequence of SEQ ID NO:16, and/or fragment thereof, and identifying a type of *P. cubensis* that infects pumpkin, watermelon, and squash when binding is detected between the second oligonucleotide and the nucleotide sequence of SEQ ID NO:52, and/or fragment thereof, thereby distinguishing the type of *P. cubensis* that infects cucumber and cantaloupe from the type of *P. cubensis* that infects pumpkin, watermelon, and squash in the sample.

In a still further embodiment, a method of distinguishing a type of *P. cubensis* that infects cucumber and cantaloupe from a type of *P. cubensis* that infects pumpkin, watermelon, and squash is provided, comprising: contacting a sample from a cucurbit plant or from an environmental sample with a first antibody that hybridizes to a polypeptide encoded by the nucleotide sequence of SEQ ID NO:16, and/or a fragment thereof, and not to a polypeptide encoded by the nucleotide sequence of SEQ ID NO:52, or fragment thereof, and/or with a second antibody that hybridizes to a polypeptide encoded by the nucleotide sequence of SEQ ID NO:52, and/or a fragment thereof, and not to a polypeptide encoded by the nucleotide sequence of SEQ ID NO:16, or fragment thereof; detecting whether the nucleotide sequence of SEQ ID NO:16, and/or fragment thereof, is present by detecting binding between the first antibody and the polypeptide encoded by the nucleotide sequence of SEQ ID NO:16, and/or fragment thereof, and/or whether the nucleotide sequence of SEQ ID NO:52 and/or fragment thereof is present by detecting binding between the second antibody and the polypeptide encoded by the nucleotide sequence of SEQ ID NO:52 and/or fragment thereof; and identifying a type of *P. cubensis* that infects cucumber and cantaloupe when binding is detected between the first antibody and the polypeptide encoded by the nucleotide sequence of SEQ ID NO:16, and/or fragment thereof, and identifying a type of *P. cubensis* that infects pumpkin, watermelon, and squash when binding is detected between the second antibody and the polypeptide encoded by the nucleotide sequence of SEQ ID NO:52, and/or fragment thereof, thereby distinguishing the type of *P. cubensis* that infects cucumber and cantaloupe from the type of *P. cubensis* that infects pumpkin, watermelon, and squash.

In an additional embodiment, a method of distinguishing a type of *P. cubensis* that infects cucumber and cantaloupe from a type of *P. cubensis* that infects pumpkin, watermelon, and squash is provided, comprising: contacting a sample from a plant or an environmental sample with a pair of oligonucleotides that hybridize to the nucleotide sequence of SEQ ID NO:16, and/or a fragment thereof, and to the nucleotide sequence of SEQ ID NO:52, and/or a fragment thereof, under conditions whereby nucleic acid amplification can occur, thereby producing an amplification product; detecting whether the nucleotide sequence of SEQ ID NO:16, and/or fragment thereof, is present by detecting binding between the amplification product and a first oligonucleotide probe that hybridizes to the nucleotide sequence of SEQ ID NO:16, and/or fragment thereof, and not to the nucleotide sequence of SEQ ID NO:52, and/or fragment thereof, and/or whether the nucleotide sequence of SEQ ID NO:52, and/or fragment thereof, is present by detecting binding between the amplification product and a second oligonucleotide probe that hybridizes to the nucleotide sequence of SEQ ID NO:52, and/or fragment thereof, and not to the nucleotide sequence of SEQ ID NO:16 and/or fragment thereof; and identifying a type of *P. cubensis* that infects cucumber and cantaloupe when binding is detected between the amplification product and the first oligonucleotide probe, and identifying a type of *P. cubensis* that infects pumpkin, watermelon, and squash when binding is detected between the amplification product and the second oligonucleotide probe, thereby distinguishing the type of *P. cubensis* that infects cucumber and cantaloupe from the type of *P. cubensis* that infects pumpkin, watermelon, and squash.

In some embodiments, "detecting" may comprise hybridizing an oligonucleotide (e.g., an oligonucleotide probe, oligonucleotide primer, nucleic acid probe, or nucleic acid primer) to a nucleotide sequence of any one of SEQ ID NOs:1-52, wherein the oligonucleotide may comprise, consist essentially of, or consist of at least about 10 consecutive nucleotides of the nucleotide sequence selected from the group of nucleotide sequences of SEQ ID NOs:1-52 (e.g., about 10, 11, 12, 13, 14, 15, 16, 17, 18, 19, 20, 21, 22, 23, 24, 25, 30, 35, 40, 45, 50, 55, 60, 70, 75, 80, 85, 90, 95, 100, 110, 115, 120, 125, 130, 135, 140, 145, 150, 155, 160, 165, 170, 175, 180, 185, 190, 195, 200 consecutive nucleotides, or more, or any range or value therein), and the presence of *P. cubensis* is detected when the oligonucleotide hybridizes to the at least one nucleotide sequence in the sample. In some embodiments, the oligonucleotide may comprise, consist essentially of, or consist of about 10 to about 2000 consecutive nucleotides of any one of the nucleotide sequences of SEQ ID NOs:1-52 (e.g., about 10 to about 30, about 10 to about 50, about 10 to about 80, about 10 to about 100, about 10 to about 150, about 10 to about 200, about 10 to about 250, about 10 to about 300, about 10 to about 350, about 10 to about 400, about 10 to about 450, about 10 to about 500, about 10 to about 550, about 10 to about 600, about 10 to about 650, about 10 to about 700, about 10 to about 750, about 10 to about 800, about 10 to about 850, about 10 to about 900, about 10 to about 950, about 10 to about 1000, about 10 to about 1100, about 10 to about 1200, about 10 to about 1300, about 10 to about 1400, about 10 to about 1500, about 10 to about 1600, about 10 to about 1700, about 10 to about 1800, about 10 to about 1900, about 10 to about 2000, about 100 to about 200, about 100 to about 250, about 100 to about 300, about 100 to about 350, about 100 to about 400, about 100 to about 450, about 100 to about 500, about 100 to about 550, about 100 to about 600, about 100 to about 650, about 100 to about 700, about 100 to about 750, about 100 to about 800, about 100 to about 850, about 100 to about 900, about 100 to about 950, about 100 to about 1000, about 100 to about 1500, about 100 to about 2000, about 200 to about 400, about 200 to about 500, about 200 to about 600, about 200 to about 800, about 200 to about 1000, about 200 to about 2000, about 500 to about 600, about 500 to about 800, about 500 to about 1000, about 500 to about 2000, or any range or value therein, of consecutive nucleotides of any one of the nucleotide sequences of SEQ ID NOs:1-52). In some embodiments, the percent identity between the oligonucleotide and the reference nucleotide can be between 70% to 100% (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100%, or any range or value therein).

Thus, an oligonucleotide useful with this invention may comprise, consist essentially of, or consist of about 50% to about 100% (e.g., about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100%, or any range or value therein) complementarity to a nucleotide sequence of SEQ ID NOs:1-52. As understood in the art, the percent complementarity between an oligonucleotide and reference polynucleotide may depend on the length of the oligonucleotide. Thus, in some embodiments, an oligonucleotide comprising, consisting essentially of, or consisting of at least about at least about 10 nucleotides can be about 80% to about 100%, about 85% to about 100%, about 90% to about 100%, about 95% to about 100% (e.g., at least about 80, 81, 82, 83, 84, 85 86, 87, 88, 89, 90, 91, 92, 93, 94, 95, 96, 97, 98, 99, 100%, or any range or value therein) complementary to a portion of consecutive nucleotides of a reference polynucleotide comprising, consisting essentially of, consisting of the nucleotide sequence of any one of SEQ ID NOs:1-52. In some embodiments, an oligonucleotide comprising, consisting essentially of, or consisting of at least about 10 to about 30 nucleotides, or about 10 to about 50 nucleotides, can be about 90% to about 100% (e.g., at least about 90, 91, 92, 93, 94, 95, 96, 97, 98, 99, 100%, or any range or value therein) complementary to a portion of consecutive nucleotides of a nucleotide sequence of any one of SEQ ID NOs:1-52. In some embodiments, an oligonucleotide comprising, consisting essentially of, or consisting of at least about 10 to about 100, about 30 to about 100 nucleotides, or about 50 to about 100 nucleotides can be about 80% to about 100%, about 85% to about 100%, about 90% to about 100%, about 95% to about 100% (e.g., about 80, 81, 82, 83, 84, 85 86, 87, 88, 89, 90, 91, 92, 93, 94, 95, 96, 97, 98, 99, 100%, or any range or value therein) complementary to a portion of consecutive nucleotides of a nucleotide sequence of any one of SEQ ID NOs:1-52. In further embodiments, an oligonucleotide comprising, consisting essentially of, or consisting of at least about 100 to about 500 nucleotides can be about 70% to about 100% complementary to a portion of consecutive nucleotides of a nucleotide sequence of any one of SEQ ID NOs:1-52 (e.g.; about 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100%, or any range or value therein). In still further embodiments, an oligonucleotide comprising, consisting essentially of, or consisting of at least about 100 to about 1000 nucleotides can be about 70% to about 100% complementary to a portion of consecutive nucleotides of a nucleotide sequence of any one of SEQ ID NOs:1-52. In some embodiments, an oligonucleotide comprising, consisting essentially of, or consisting of at least about 1000 to about 2000 nucleotides can be about 50% to about 100% complementary to a portion of consecutive nucleotides of a nucleotide sequence of any one of SEQ ID NOs:1-52 (e.g., about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100%, or any range or value therein).

A pair of oligonucleotides as used herein means two oligonucleotides that may be used, for example, as primers to carry out an amplification reaction (e.g., PCR). Those of skill in the art are aware of the requirements for amplification primers and can develop primers to amplify any region of a known nucleotide sequence.

Detecting may comprise any method known or later developed to detect the presence of a nucleic acid or a polypeptide. A nucleic acid and/or polypeptide may be also be distinguished from another nucleic acid and/or polypeptide by analysis of the length of the nucleic acid or polypeptide or by sequencing. Methods for detecting the presence of a nucleic acid or a polypeptide, or determining its length or sequence are known and include, but are not limited to, Southern analysis, PCR amplification for detection of a polynucleotide, Northern blots, RNase protection, primer-extension, RT-PCR amplification for detecting RNA transcripts, enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

In some embodiments, detecting a nucleotide sequence of the invention (e.g., SEQ ID NOs:1-52, or a fragment thereof) in a sample includes but is not limited to an amplification reaction, an amplification reaction with a single base extension, matrix-assisted laser desorption/ionization-time of flight mass spectrometry (MALDI-TOF-MS), sequencing, hybridization, restriction endonuclease digestion analysis, electrophoresis, or any combination thereof.

In some embodiments, more than one nucleotide sequence of SEQ ID NOs:1-52 (e.g., 1, 2, 3, 4, 5, 6, 7, 8, 9, 10, or more) may be detected by contacting a sample with more than one oligonucleotide probe or more than one pair of oligonucleotide primers.

In some embodiments, the detecting may comprise amplifying a fragment comprising at least about 25 consecutive nucleotides of a nucleotide sequence of SEQ ID NOs:1-52, or any combination thereof, detecting the presence of the fragment, wherein the presence of the fragment indicates the presence of *P. cubensis* in the sample. In some embodiments, the fragment can be about 15 consecutive nucleotides to the full length of the nucleotide sequence (e.g., about 15, 16, 17, 18, 19, 20, 21, 22, 23, 24, 25, 26, 27, 28, 29, 30, 31, 32, 33, 34, 35 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1100, 1200, 1300, 1500, 1600, 1700, 1800, 1900, 2000, 2100, 2200, 2300, 2400, 2500 consecutive nucleotides, or any range or value therein). In some embodiments, the fragment can be about 15 consecutive nucleotides to 50 consecutive nucleotides, about 25 consecutive nucleotides to 50 consecutive nucleotides, about 25 consecutive nucleotides to 75 consecutive nucleotides, about 25 consecutive nucleotides to 100 consecutive nucleotides, about 50 consecutive nucleotides to 100 consecutive nucleotides, about 50 consecutive nucleotides to 150 consecutive nucleotides, about 50 consecutive nucleotides to 200 consecutive nucleotides, about 100 consecutive nucleotides to 150 consecutive nucleotides, about 100 consecutive nucleotides to 200 consecutive nucleotides, about 100 consecutive nucleotides to 250 consecutive nucleotides, about 100 consecutive nucleotides to 350 consecutive nucleotides, about 100 consecutive nucleotides to 500 consecutive nucleotides, about 200 consecutive nucleotides to 250 consecutive nucleotides, about 200 consecutive nucleotides to 350 consecutive nucleotides, about 200 consecutive nucleotides to 450 consecutive nucleotides, about 200 consecutive nucleotides to 500 consecutive nucleotides, about 200 consecutive nucleotides to 600 consecutive nucleotides, about 300 consecutive nucleotides to 500 consecutive nucleotides, about 400 consecutive nucleotides to 500 consecutive nucleotides, about 400 consecutive nucleotides to 600 consecutive nucleotides, about 400 consecutive nucleotides to 700 consecutive nucleotides, about 400 consecutive nucleotides to 800 consecutive nucleotides, about 500 consecutive nucleotides to 1000 consecutive nucleotides, about 500 consecutive nucleotides to 1200 consecutive nucleotides, about 500 consecutive nucleotides to 1500 consecutive nucleotides, about 750 consecutive nucleotides to 1000 consecutive nucleotides, about 750 consecutive nucleotides to 1500 consecutive nucleotides, about 1000 consecutive nucleotides to 1500 consecutive nucleotides, about 1000 consecutive nucleotides to 2000 consecutive nucleotides, about 1000 consecutive nucleotides to 2500 consecutive nucleotides, and any value or range therein). In further embodiments, a method of amplifying can comprise amplifying the full length of an nucleotide sequence of any one or more of SEQ ID NOs:1-52.

Once *P. cubensis* is identified in a sample or the type of *P. cubensis* is identified in a sample (e.g., whether the *P. cubensis* is identified as a type that infects cucumber and cantaloupe or a type that infects pumpkin, watermelon, and squash) a treatment regimen may be selected and/or implemented. Any effective treatment(s) known or later developed for treating a *P. cubensis* infection may be used with the methods of the invention. Non-limiting examples of compositions that may be used in a treatment regimen for a *P. cubensis* infection of a cucurbit plant includes, but is not limited to, oxathiapiprolin, cyazofamid, propamocarb, famoxadone and cymoxanil, ametoctradin and dimethomorph, mancozeb, mancozeb+zoxamide, and/or chlorothalonil. In some embodiments, a treatment for a type of *P. cubensis* that infects cucumber and cantaloupe may differ from a treatment for a type of *P. cubensis* that infects pumpkin, watermelon, and squash by the timing of the treatment. For example cucumber and cantaloupe typically become infected earlier in the growing season, thus, the treatments begin earlier and more sprays are required in contrast to the other crops, which typically become infected later in the growing season By the terms "treat," "treating," or "treatment of" (and grammatical variations thereof) it is meant that the severity of a plant's condition is reduced, at least partially improved or ameliorated and/or that some alleviation, mitigation or decrease in at least one symptom is achieved and/or there is a delay in the progression of the disease or disorder. The terms “treat,” “treating,” or “treatment of” are also meant to refer to the prevention or reduction in the severity of a *P. cubensis* infection or outbreak, which may be measured by a reduction in the number of plants infected and/or the severity of the condition of the plants, which condition may be at least partially improved or ameliorated and/or that some alleviation, mitigation or decrease in at least one symptom is achieved and/or there is a delay in the progression of the disease or disorder. An “effective treatment” as used herein is a treatment that is sufficient to reduce the severity of a plant’s condition due to infection by *P. cubensis* (e.g., at least partially improve or ameliorate said condition), to alleviate, mitigate or decrease at least one symptom due to a *P. cubensis* infection and/or results in a delay in the progression of the disease or disorder. An effective treatment further refers to a treatment that alleviates, mitigates or reduces a *P. cubensis* outbreak or its severity; that is the treatment mitigates or reduces the number of plants that become infected. Those skilled in the art will appreciate that for a treatment to be effective it need not be complete or curative, as long as some benefit is provided to the crop, the plant and/or plant part.

In addition, to methods for identifying *P. cubensis* and diagnosing *P. cubensis* infections, the present invention further provides methods for selecting genes from cucurbits that may be useful for conferring resistance to *P. cubensis*. Thus, in some embodiments, a method for selecting a cucurbit plant comprising at least one gene that confers resistance to *P. cubensis* is provided, comprising introducing into the cucurbit plant at least one of (a) a nucleotide sequence of any one of SEQ ID NOs:1-52, or a complement thereof; (b) a nucleotide sequence having at least about 80% sequence identity to the nucleotide sequence of any one of (a); (c) a nucleotide sequence which anneals under stringent hybridization conditions to the nucleotide sequence of any one of (a) to (b), or a complement thereof; and (d) a nucleotide sequence that differs from the nucleotide sequences of any one of (a) to (c) above due to the degeneracy of the genetic code, wherein the expression of the at least one nucleotide sequence produces a hypersensitive response in a cucurbit plant comprising a gene that confers resistance to *P. cubensis*, thereby identifying the cucurbit plant as comprising a gene that confers resistance to *P. cubensis*; and selecting the plant having the hypersensitive response and identified as comprising the gene that confers resistance to *P. cubensis*. In some embodiments, the at least one nucleotide sequence of SEQ ID NOs:1-52, or fragment thereof, may be comprised in recombinant nucleic acid construct and/or an expression vector.

In some embodiments, a method of producing a plant having increased resistance to *P. cubensis* is provided, comprising: (a) introducing into the cucurbit plant at least one of (i) a nucleotide sequence of any one of SEQ ID NOs:1-52, or a complement thereof; (ii) a nucleotide sequence having at least about 80% sequence identity to the nucleotide sequence of any one of (i); (iii) a nucleotide sequence which anneals under stringent hybridization conditions to the nucleotide sequence of any one of (i) to (ii), or a complement thereof; and (iv) a nucleotide sequence that differs from the nucleotide sequences of any one of (i) to (iii) above due to the degeneracy of the genetic code, wherein the expression of the at least one nucleotide sequence produces a hypersensitive response in a cucurbit plant comprising a gene that confers resistance to *P. cubensis*, thereby identifying the cucurbit plant as comprising a gene that confers resistance to *P. cubensis*; selecting a plant having the hypersensitive response and identified as comprising the gene that confers resistance to *P. cubensis*; (b) crossing the selected plant with a second cucurbit plant; and (c) selecting progeny comprising increased resistance to *P. cubensis*, thereby producing a plant having increased resistance to *P. cubensis*.

In representative embodiments, the at least one nucleotide sequence of SEQ ID NOs:1-52, or a fragment thereof, that is introduced may be the nucleotide sequence of SEQ ID NO:2, SEQ ID NO:13, SEQ ID NO:16, SEQ ID NO:17, SEQ ID NO:24, SEQ ID NO:39, SEQ ID NO:43, SEQ ID NO:52, or a fragment thereof, or any combination thereof.

“Introducing,” in the context of a polynucleotide of interest (e.g., a nucleotide sequence encoding an amino acid sequence having at least about 80% identity to any of SEQ ID NOs:1-52, a nucleotide sequence having at least about 80% identity to any of SEQ ID NOs:1-52, and/or functional fragments thereof), means presenting the polynucleotide of interest to the cell of an organism in such a manner that the nucleotide sequence gains access to the interior of the cell. The methods of the invention do not depend on a particular method for introducing one or more nucleotide sequences into an organism, only that they gain access to the interior of at least one cell of the organism. Where more than one nucleotide sequence is to be introduced, these nucleotide sequences can be assembled as part of a single polynucleotide or nucleic acid construct, or as separate polynucleotide or nucleic acid constructs, and can be located on the same or different expression constructs or transformation vectors. Accordingly, these polynucleotides may be introduced into cells in a single transformation event, in separate transformation events, or, for example, they may be incorporated into an organism as part of a breeding protocol.

The term “transformation” as used herein refers to the introduction of a heterologous nucleic acid into a cell. Transformation of a cell may be stable or transient. Thus, in some embodiments, a cell of the invention may be stably transformed with a nucleotide sequence of the invention. In other embodiments, a cell may be transiently transformed with a nucleotide sequence of the invention. In particular embodiments, the plant leaf is infiltrated with a vector comprising a nucleotide sequence of the invention and the cells are transiently transformed.

“Transient transformation” in the context of a polynucleotide means that a polynucleotide is introduced into the cell and does not integrate into the genome of the cell.

By “stably introducing” or “stably introduced” in the context of a polynucleotide introduced into a cell is intended that the introduced polynucleotide is stably incorporated into the genome of the cell, and thus the cell is stably transformed with the polynucleotide.

“Stable transformation” or “stably transformed” as used herein means that a polynucleotide is introduced into a cell and integrates into the genome of the cell. As such, the integrated polynucleotide is capable of being inherited by the progeny thereof, more particularly, by the progeny of multiple successive generations. “Genome” as used herein also includes the nuclear, mitochondrial, and plastid genome, and therefore includes integration of the nucleic acid into, for example, the chloroplast or mitochondrial genome. Stable transformation as used herein can also refer to a transgene that is maintained extrachromasomally, for example, as a minichromosome.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences, which specifically hybridize with a nucleotide sequence of a transgene introduced into an organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

The term "hypersensitive response" as used herein refers to the plant response characterized by rapid cell death in a limited region surrounding an infection. A hypersensitive response may serve to restrict the growth and spread of pathogens to other parts of the plant.

Any cucurbit now known or later identified may be useful with any of the methods of this invention. Thus, in some embodiments, a cucurbit plant may be a wild cucurbit, a cucurbit breeding line, or a commercial cucurbit line. In some embodiments, the cucurbit plant may be from the Cucurbitaceae plant family. In some embodiments, a cucurbit plant may be from a genus in the Cucurbitaceae plant family as set forth in Table 1, or any cultivar, variety or line therein. In representative embodiments, the cucurbit plant may be in the genus of *Cucumis* spp. *Cucurbita* spp., *Citrullus* spp, *Lagenaria* spp., or *Luffa* spp., or any cultivar, variety or line therein. In some embodiments, the cucurbit plant may be a cucumber plant, a watermelon plant, a squash plant, a pumpkin plant, and/or a cantaloupe plant, or any cultivar, variety or line thereof. In some aspects, a cucurbit plant, as used herein, can be one that is suspected of being infected with *P. cubensis*.

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1. Sample Preparation for Sequencing and Candidate Validation

Isolates of *P. cubensis* and *P. humuli* used in this study for genome and transcriptome sequencing are listed in Table 1. Isolates were propagated on detached leaves to minimize contamination from other pathogens and insects and to obtain high quality RNA and DNA for sequencing. *P. cubensis* and *P. humuli* isolates were propagated on the host that they were originally isolated from. Detached leaves were placed upside down on moist sterile paper towels inside clear acrylic boxes, spray inoculated with a sporangial suspension of 1 to $3\times10^4$ sporangia/ml for each isolate, and incubated at 25° C. with an 12 h light/dark cycle in a precision plant growth chamber (Thermo Fisher Scientific, Waltham, Mass.). Sporangia were dislodged from leaves using a Preval® sprayer (Preval, Coal City, Ill.) with sterile water, collected into a tube, and pelleted by centrifugation. Sporangia intended for use in RNA extractions were then suspended in RNALater@ (ThermoFisher Scientific, Waltham, Mass.) at a sporangial concentration of 1 mg/µl, while sporangia for DNA extraction were suspended in sterile water. Additional samples used for the diagnostic candidate validation included infected lesions with sporulation or no sporulation collected from field samples (Table 2), mycelia from other oomycetes (Table 2), and uninfected plant tissue grown in the laboratory (Table 3). Samples were stored in microcentrifuge tubes in liquid nitrogen for long-term preservation.

Example 2. RNA and DNA Extraction, Library Preparation, and Sequencing

In preparation for RNA and DNA extraction, 50 µl of sporangial suspension from each isolate was collected in a microcentrifuge tube with 500 µm glass beads (Sigma, St. Louis, Mo.) and 1 mg polyvinyl polypyrrolidone (PVPP). Infected lesions, uninfected plant tissue, and other oomycete tissues were each collected into microcentrifuge tubes with three 2.3 mm Zircon beads (Biospec, Bartlesville, Okla.), 50 mg 500 µm glass beads (Sigma), and 1 mg PVPP. All tissues for RNA and DNA extraction were lysed using an OMNI International Bead Ruptor (OMNI International, Tulsa, Okla.). RNA was extracted using the Qiagen Plant RNeasy® Kit (Qiagen, Valencia, Calif.) with an on-column DNAse digestion using the Qiagen DNAse Digest (Qiagen), both according to manufacturer's instructions. RNA was eluted with 30 to 100 µl DEPC-treated water and re-precipitated using 1/10 volume of 3M sodium acetate and two volumes of 96% ethanol, washed with 500 µl 80% ethanol and re-suspended with 30-1001 µl DEPC-treated water. DNA extractions were completed using 500 µl SDS extraction buffer (200 mM Tris-HCl pH8, 250 mM NaCl, 25 mM EDTA, 0.5% SDS) followed by one 500 µl phenol and two 500 µl chloroform extractions. DNA was precipitated with 0.5 volume of 100% isopropanol, washed with 500 µl 80% ethanol, suspended in 100 µl sterile distilled water, then re-precipitated with sodium acetate and ethanol as described above, and re-suspended in sterile 30 to 100 µl distilled water. RNA samples for sequencing were quantified using the Qubit® RNA HS assay (Life Technologies, Grand Island, N.Y.), DNA samples for sequencing using the Qubit® DNA BR assay (Life Technologies), and DNA samples for the diagnostic screen were quantified using a Nanodrop 1000 (Thermo Fisher Scientific, Waltham, Mass.). Total RNA was checked for integrity and quality using the Agilent Bioanalyzer 2100 (Agilent Technologies, Santa Clara, Calif.). DNA quality assessment was based on gel electrophoresis on a 1% agarose gel containing 0.2 µg/ml ethidium bromide, followed by detection with a Biorad Geldoc™ Imager using Quantity One® software (Biorad, Hercules, Calif.).

High quality total RNA and DNA were submitted to the Michigan State University Research Technology Support Facility (MSU-RTSF) for Illumina Truseq® RNA (350 bp insert size) and DNA (500 bp insert size) library preparation (Illumina, San Diego, Calif.). RNA and DNA libraries were barcoded and multiplexed for 50 bp single-end RNA-seq and 100 bp paired-end DNA-seq, respectively. All samples were run on an Illumina HiSeq® 2500 (Illumina, San Diego, Calif.) and base calling and quality values were determined using the Illumina software as part of the service provided by the MSU-RTSF.

Example 3. Identification of Candidate Diagnostic Markers and Primer Design

Figure 2:
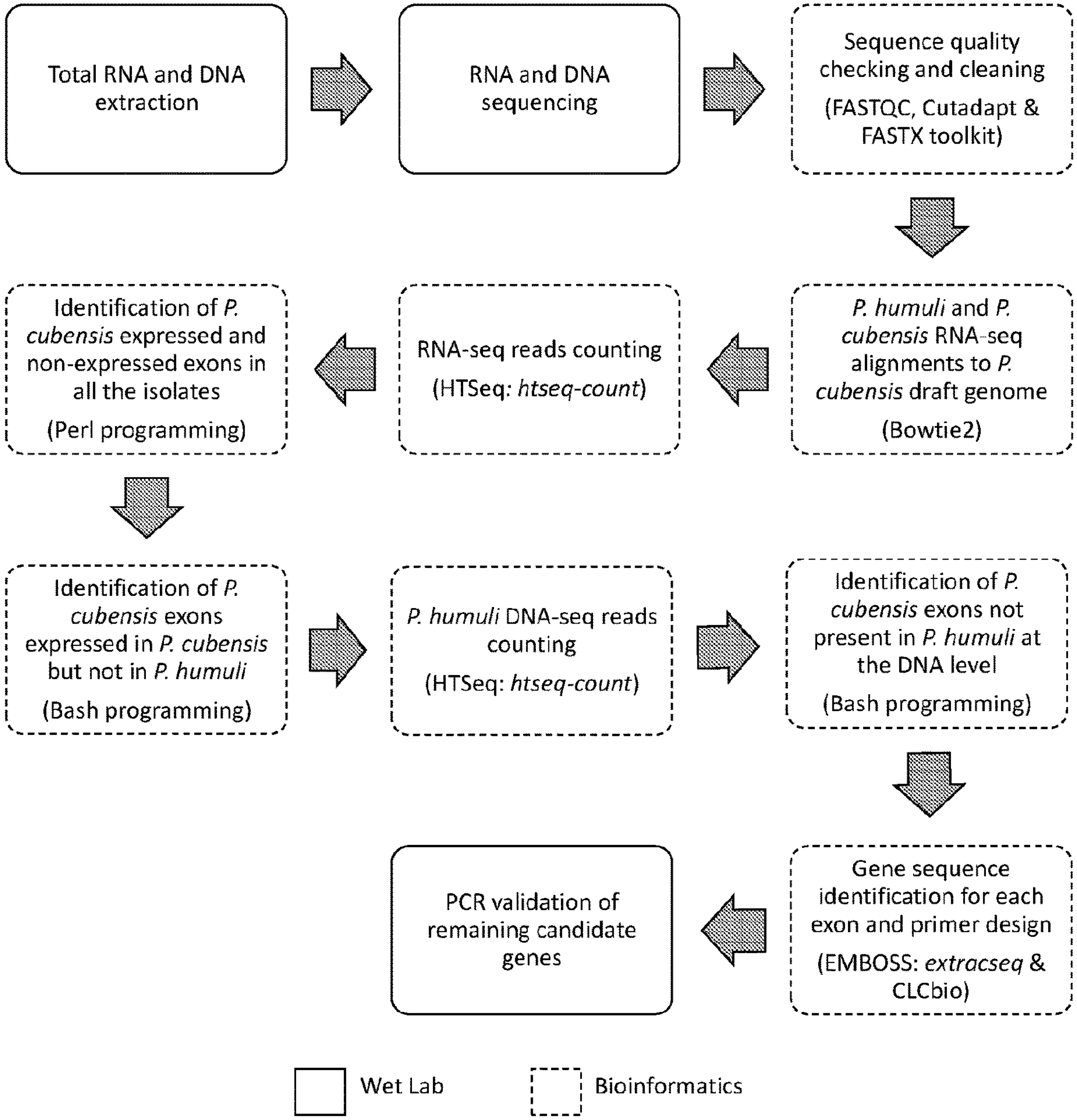
FIG. 2 provides a flow diagram outlining an approach of the present inventors for identifying candidate diagnostic markers for *Pseudoperonospora cubensis.*

RNA-seq and DNA-seq reads were analyzed for quality using FastQC (v. 0.10.1) (Andrews, 2012). Cutadapt (v. 1.8.1) (Martin, 2012) and FASTX-Toolkit (v. 0.0.13) (Hannon, 2010) were used to remove adaptors and trim low quality sequences from the dataset, respectively. Due to the obligate nature of *P. cubensis* and *P. humuli*, one may find plant contamination in the RNA and DNA samples. Thus, to determine the level of plant contamination in the samples RNA-seq reads were aligned with the *Cucumis sativus* (cucumber) genome (Huang et al., 2009) using Bowtie2 short read aligner (v. 2.1.0) (Langmead et al., 2009). To identify diagnostic candidates, RNA-seq reads from *P. cubensis* and *P. humuli* were aligned to the *P. cubensis* draft genome (Savory et al., 2012a; Savory et al., 2012b) using Bowtie2 short read aligner (v.2.1.0). The number of aligned reads in each exon of the *P. cubensis* draft genome was quantifed using htseq-count from HTSeq (v. 0.6.1) (Anders et al., 2015) with default parameters. Exons in the *P. cubensis* draft genome with at least two mapped reads from *P. cubensis* RNA-seq samples and less than two mapped reads from *P. humuli* RNA-seq samples were identified and selected using Perl and Bash programming. Exons present in all *P. cubensis* RNA-seq samples (>2 mapped reads) but absent in all *P. humuli* RNA-seq samples (<2 mapped reads) were matched to specific genes using the *P. cubensis* draft genome GFF3 file coordinates (Savory et al., 2012a). To further reduce the number of diagnostic candidates to validate with PCR, DNA-seq data was aligned in single end mode to the *P. cubensis* draft genome using Bowtie2 (v. 2.1.0) (Langmead et al., 2009) and mapped reads were quantified using htseq-count from HTSeq (v. 0.6.1) (Anders et al., 2015). Candidates were eliminated if two or more DNA-seq reads from *P. humuli* were present in the candidate exon. Approximately 50% of the remaining candidates were validated by PCR against a larger selection of lesions infected with *P. cubensis* or *P. humuli*, other oomycete isolates (Table 2), and host plants (Table 3) to eliminate candidates that occur infrequently, or that are present in more distantly related oomycetes, or in the host (FIG. 2). To determine if candidate diagnostic markers were in putative single copy genes, a self-BLASTP (Altschul et al., 1990) analysis of the *P. cubensis* predicted proteome (Savory et al., 2012a) using an E-value cutoff of $1e^{-10}$ was performed. Candidates were considered single copy if protein sequences had only one match to the proteome. Since several candidate diagnostic markers were annotated as genes of unknown function, a BLASTX analysis against *Phytophthora infestans, Phytophthora capsici* and *Hyaloperonospera arabidopsis* proteins was performed to improve gene functional annotation. The collection of protein sequences were downloaded from NCBI on 3 Jun. 2015 and an E-value cutoff of 1e° 5 was used to define homologous sequences. To further determine that candidates were specific to *P. cubensis*, gene sequences of the diagnostic candidates were used to perform a BLASTN (Altschul et al., 1990) search against the NCBI nucleotide collection (nr/nt)(non-redundant nucleotide) database using default parameters to retain candidates with no significant sequence similarity to other organisms for laboratory validation.

Example 4. Validation of Diagnostic Candidates

Fasta sequences of genes containing candidate diagnostic exons and the 200 bp region flanking each gene were selected using extracseq from EMBOSS (v. 6.5.7). Primers were designed for *P. cubensis* diagnostic candidates selected for validation within 200 bp 5' and 3' end of the candidate gene using CLC Genomics Workbench (CLCbio, Boston, Mass.) and IDT Oligo Analyzer (Integrated DNA Technologies, Coralville, Iowa). The *P. cubensis* draft genome and the RNA-seq and DNA-seq read alignments were imported into RNA-seq tools of the CLC Genomics Workbench to identify primers flanking diagnostic candidates. Primers were designed to produce product sizes between 200 and 1,200 bp with an annealing temperature of 55 to 57° C., and were ordered through IDT (Integrated DNA Technologies). The PCR reactions, completed according to manufacturer's guidelines, contained 1× Promega GoTaq® Green Master Mix (Promega, Durham, N.C.), 10 μM of forward and reverse primers, and 10 μM DNA, and were amplified with a program starting with 94° C. for 3 minutes, followed by 35 cycles of 94° C. for 30 seconds, 55° C. for 30 seconds, 72° C. for 30 seconds, with a final elongation step of 72'C for 5 minutes. Products were analyzed by gel electrophoresis on a 2% agarose gel containing 0.2 μg/ml ethidium bromide, followed by detection with a Biorad Geldoc™ Imager using Quantity One® software (Bio-Rad, Hercules, Calif.). Product sizes were estimated by comparison to the Life Technologies 100 bp DNA ladder. Diagnostic candidates with product sizes similar in *P. cubensis* and *P. humuli* samples, as well as any that were amplified in any of the plant hosts or other oomycetes screened were eliminated. Candidates remaining after at least three validation iterations were considered highly specific diagnostic molecular markers for *P. cubensis* (e.g., SEQ ID NOs:1-52).

Example 5. Identification of Diagnostic Markers

The approach used in our study successfully identified seven diagnostic markers for *P. cubensis* by using comparative genomics with the closely related species *P. humuli*, a previously published *P. cubensis* draft genome assembly (Savory et al., 2012b), minimal additional genomic data, and validation of diagnostic candidates with diverse samples (FIG. 2).

Figure 6A:
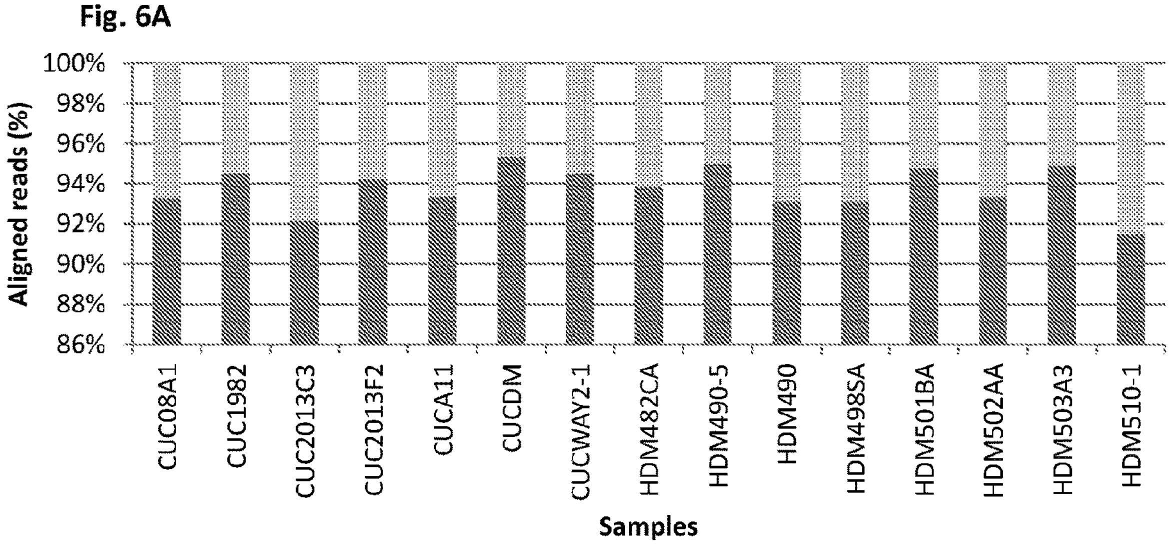
FIGS. 6A-6B provide the percentage of uniquely and multiple mapped reads when aligning to *Pseudoperonospora cubensis* and *Cucumis sativus* genomes using Bowtie2.
Figure 6B:
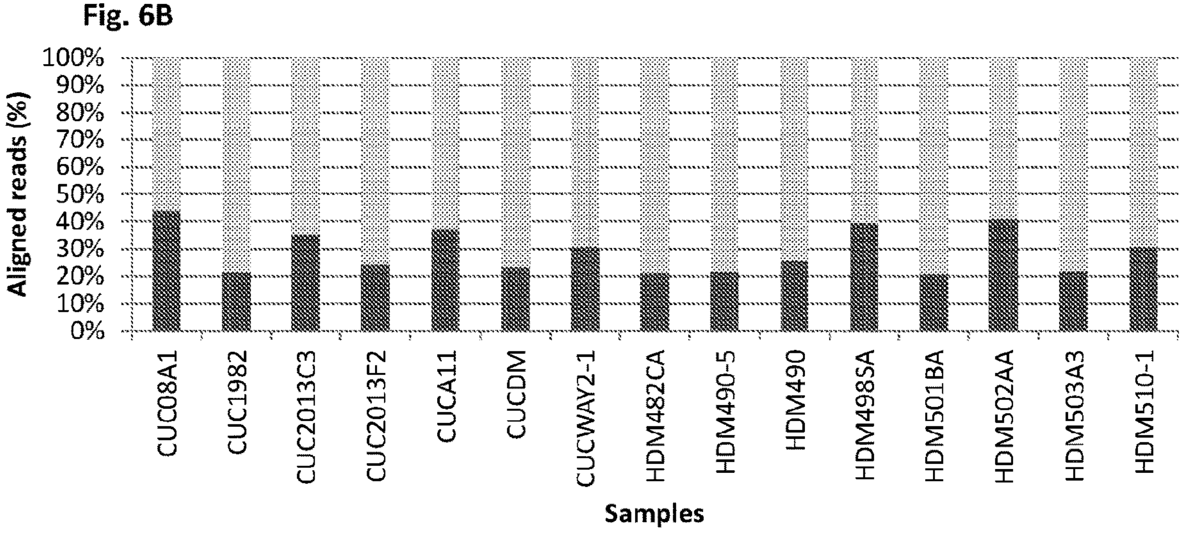

A range of 11,942,671 to 29,304,711 million of RNA-seq and 36,599,100 million of DNA-seq reads were obtained and checked for quality (Table 4). In general, only 0.21 to 0.49% of reads were removed from RNA-seq samples and 40% from DNA-seq samples due to low quality and plant contamination (Table 4). High quality RNA-seq and DNA-seq reads aligned to the *P. cubensis* draft genome confirmed that the majority of sequences were from the pathogens (Table 4). The highest and lowest percentages of total aligned RNA-seq reads for *P. cubensis* samples to the *P. cubensis* genome were 95% and 79.9%, respectively. For *P. humuli* samples, the highest and lowest percentage of total aligned RNA-seq reads to the *P. cubensis* draft genome was 92.3% and 66.9%, respectively, and 97.5% and 96% was the highest and lowest total alignment percentage for DNA-seq reads. A small percentage of RNA-seq reads of *P. cubensis* (0.5% to 6.7%) and *P. humuli* (0.5% to 7.5%) isolates aligned to the *C. sativus* reference genome. Similarly, a low percentage (12 to 13%) of DNA-seq reads from a single *P. humuli* isolate aligned to the *C. sativus* reference genome (Table 4). The total *P. cubensis* and *P. humuli* RNA-seq and DNA-seq reads aligned to the *P. cubensis* draft genome and the *C. sativus* reference genome for each sample were sorted in uniquely mapped reads and multiple mapped reads to further assess read quality. A range of 92% to 96% of uniquely mapped reads was observed, confirming the good quality of the RNA-seq reads (FIG. 6).

Figure 3:
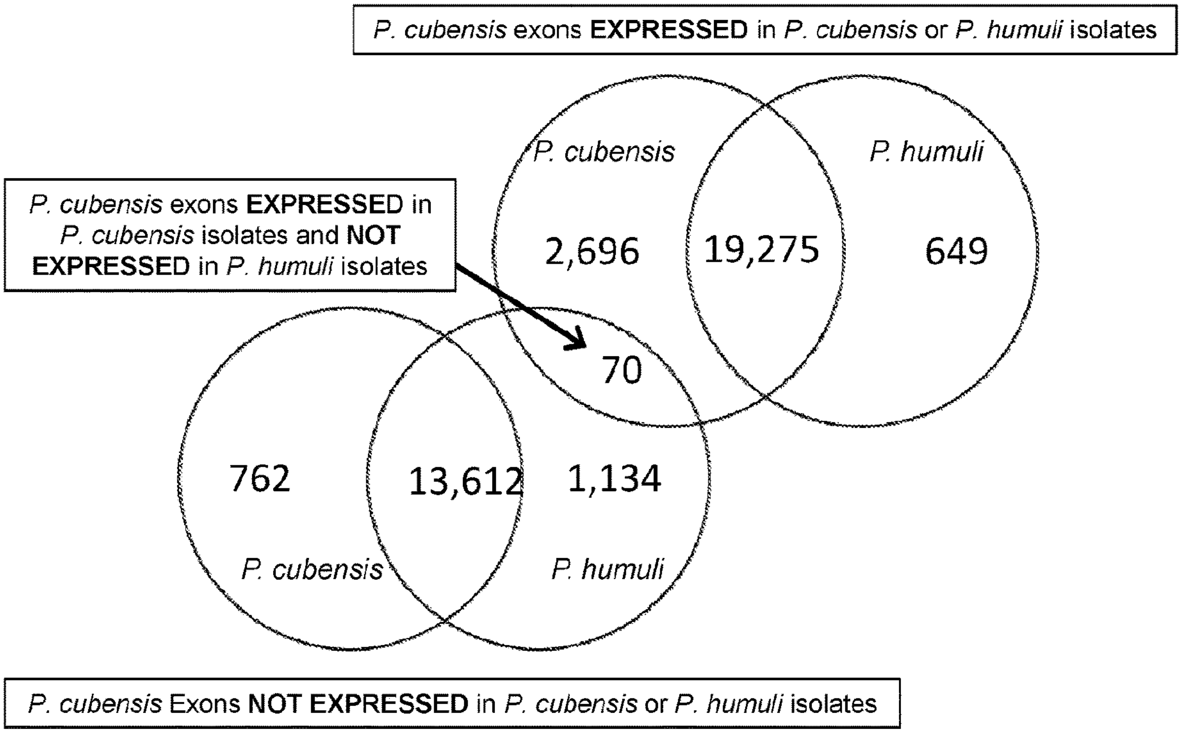
FIG. 3 provides a Venn diagram describing results from HTSeq analysis. The number of expressed and not-expressed *Pseudoperonospora cubensis* exons in *P. cubensis* and *Pseudoperonospora humuli* isolates sequenced are shown in the Venn diagram.

An analysis of exon expression performed on mapped RNA-seq reads indicated that 2,696 *P. cubensis* exons were expressed in all *P. cubensis* isolates, 649 *P. cubensis* exons were expressed in all *P. humuli* isolates, and 19,275 *P. cubensis* exons were expressed in all sequenced isolates of both species. Moreover, 762 and 1,134 *P. cubensis* exons were found to be not expressed in any *P. cubensis* and *P. humuli* isolates, respectively, and 13,612 *P. cubensis* exons were not expressed in isolates of either species. A total of 70 *P. cubensis* exons were identified from 51 genes that were expressed in all *P. cubensis* isolates and not in any *P. humuli* isolates sequenced (FIG. 3, Table 6). Self-BLASTP analyses revealed that six of the 51 candidate diagnostic genes were putative single copy genes (Table 6). Of the 51 identified genes, 29 were annotated as genes or proteins of unknown function. The remaining 22 genes had functional annotations related to virulence (elicitins, elicitors, NPP1 and CRN proteins) and signaling, among others. BLAST® searches performed against a protein database from *P. infestans, P. capsici* and *H. arabidopsidis* allowed annotation of three more genes. These three genes were putatively identified as involved in functions related to virulence (c27478.0e0) (SEQ ID NO:20), glycolysis (c30239.0e0), and chromatin remodeling (c2555.4e5) (SEQ ID NO:18) (Table 6). Candidate c2163.6e5 (SEQ ID NO:12) had 78% identity (38% query cover and $5e^{-87}$ E value) with a *Phytophthora sojae* hypothetical protein (XM_009528096.1), c31609.0e0 (SEQ ID NO:25) had 93% identity (17% query cover and $2e^{-06}$ E value) with an *Aphanomyces invadans* protein kinase (XM_008871021.1), and c6944.1e0-1 (SEQ ID NO:46) had 89% identity (24% query cover and $8e^{-65}$ E value) with a *Phytophthora parasitica* hypothetical protein (XM_008912304.1).

Validation of Diagnostic Candidates

An additional filtering step using HTSeq and DNA-seq data from a single *P. humuli* isolate allowed us to eliminate 29 *P. cubensis* exons in 21 genes that were not present in the RNA-seq data of *P. humuli* but were present at the DNA level (Table 6). Of the remaining 30 genes determined to contain 41 exons unique to *P. cubensis* after bioinformatics analyses, a subset of 16 genes containing 26 exons (about 50% of candidates) were chosen for PCR validation with 96 diverse isolates (Table 2). An initial screening with 15 *P. cubensis* and nine *P. humuli* samples eliminated 15 candidate exons in eight genes that had a product in *P. humuli* samples indistinguishable in size from the PCR product obtained in *P. cubensis* samples. The final screening for the remaining 11 exons in eight genes included 49 *P. cubensis,* 34 *P. humuli*, five *P. belbahrii*, three *P. obducens*, six *Phytophthora capsici* and 8 *Phytophthora infestans* samples or isolates (Table 2). Eight plant hosts were also included in the validation due to the obligate nature of *P. cubensis* and comprised cucumber, cantaloupe, butternut squash, acorn squash, pumpkin, watermelon, basil, and hop (Table 3). This final screening eliminated 1 exon in 1 gene that had a product in *P. obducens* samples indistinguishable in size from the PCR product obtained in *P. cubensis* samples (Table 6). No other candidates presented amplification of a product in other samples that could not be distinguished from *P. cubensis.*

Figure 4:
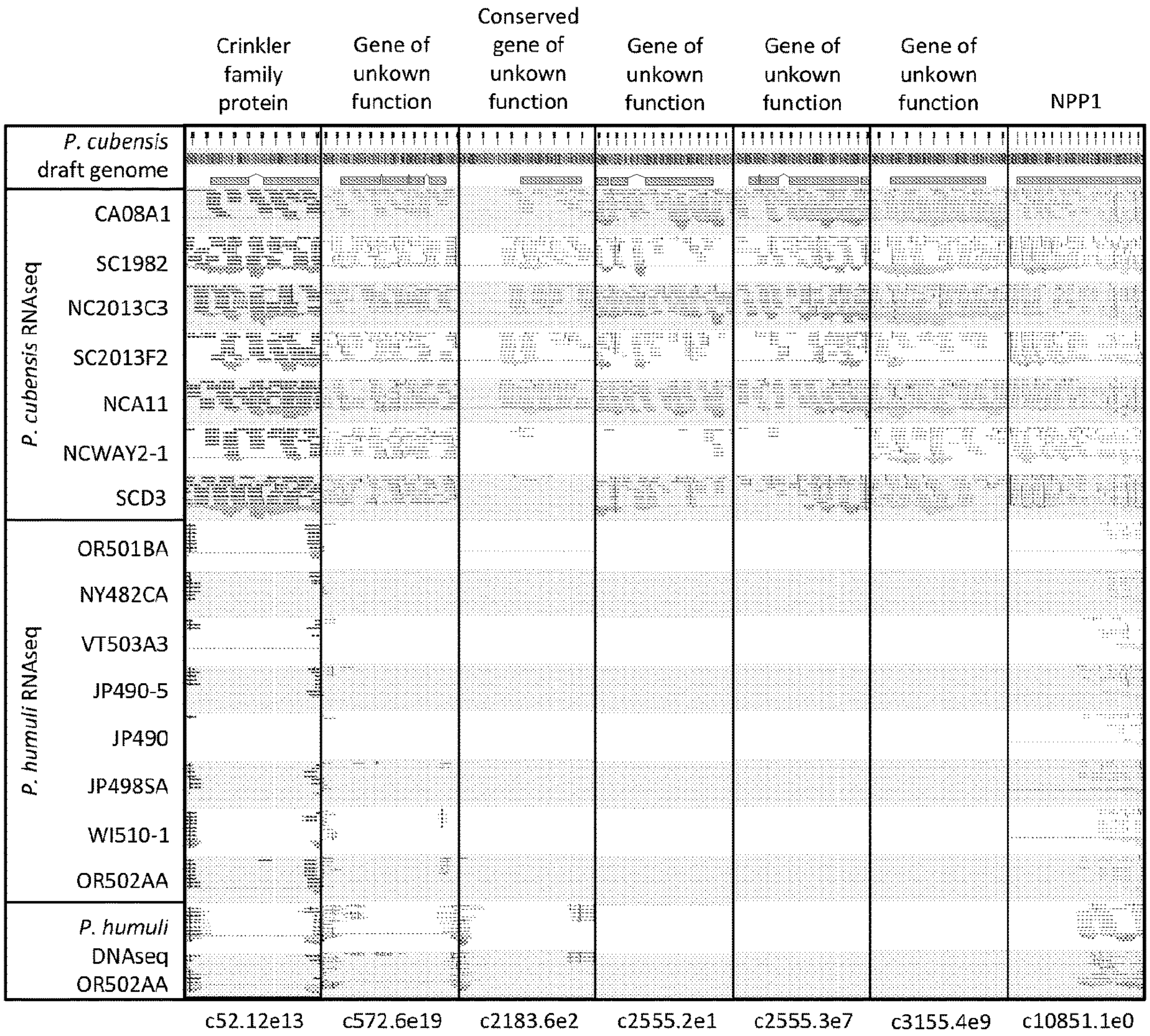
FIG. 4 shows the use of next generation sequencing to identify species-specific regions in *Pseudoperonospora. cubensis* utilizing comparative genomics with the closely related species *P. humuli*. Seven species-specific regions (c52.12e13, c572.6e19, c2183.6e2, c2555.2e1, c2555.3e7, c3155.4e9, c10851.1e0) are shown in the figure as columns with the gene functional annotation above each column and the candidate diagnostic code below each column. The *P. cubensis* genome panel shows predicted genes in the *P. cubensis* genome that are absent or have missing exons in the *P. humuli* genome. RNA-seq was performed in a diverse panel of *P. cubensis* (CA08A1, SC1982, NC2013C3, SC2013F2, NCA11, NCWAY2-1, SCD3) and *P. humuli* (OR501BA, NY482CA, VT503A3, JP490-5, JP498SA, WI510-1, OR502AA) isolates to detect transcripts always present in *P. cubensis* but not present in *P. humuli* by mapping reads to the *P. cubensis* genome using HTSeq. To confirm the absence of the exon or gene at the DNA level in *P. humuli* and develop a PCR-based assay, DNA-seq was performed on *P. humuli* (OR502AA). Primers were designed flanking each gene to detect a size difference in PCR products between *P. cubensis* and *P. humuli* due to the absence of exons or genes in *P. humuli*. This figure was generated using the CLC Genomics Workbench (CLCbio, Boston, Mass.).

These remaining 10 exons in 7 genes (c10851.1e0, c2555.2e1, c2555.3e7, c3155.4e9, c52.12e13, c572.6e19, and c2183.6e2; SEQ ID NOs:2, 17, 16, 24, 39, 43, and 13, respectively) are considered highly specific diagnostic molecular markers for *P. cubensis* that can be used to distinguish it from its sister species *P. humuli* (Table 5, FIG. 4). Two (c2555.2e1 (SEQ ID NO:17) and c2555.3e7 (SEQ ID NO:16)) of these genes were found to be putative single copy genes through self-BLASTP analyses (Table 5, Table 6). PCR assays with the designed primers and gel electrophoresis of the seven final diagnostic candidates revealed that three candidates (c2555.2e1 (SEQ ID NO:17), c2555.3e7 (SEQ ID NO:16), and c10851.1e0 (SEQ ID NO:2)) did not produce a PCR product in any *P. humuli* samples tested, while four candidates (c52.12e13 (SEQ ID NO:39), c572.6e19 (SEQ ID NO:43), c2183.6e2 (SEQ ID NO:13), and c3155.4e9 (SEQ ID NO:24)) produced a PCR product of different size in some or all of the *P. humuli* samples tested. All diagnostic candidates successfully detected *P. cubensis* in hosts such as watermelon, cantaloupe, and buffalo gourd that typically have lower pathogen sporulation (Table 2, FIG. 5). Interestingly, one diagnostic candidate (c2555.3e7) (SEQ ID NO:16) with unknown function had polymorphism among *P. cubensis* samples tested depending on the host. Samples from infected watermelon, pumpkin, and butternut squash had a larger PCR product than those from cucumber, cantaloupe, and buffalo gourd.

Example 6

Next Generation Sequencing allows for development of sequence-based, culture-independent diagnostics of pathogens (Pallen et al., 2010). A recent study used genomics approaches to develop diagnostics for obligate pathogens of humans such as *Parachlamydia acanthamoebae* (Greub et al., 2009). In that study, a draft genome sequence of the emergent pathogen *P. acanthamoebae* was obtained and used in combination with proteomics to identify immunogenic proteins and develop a serological diagnostic assay (Greub et al., 2009). However, there have been few examples of genomics-enabled diagnostics development for plant pathogens (Studholme et al., 2011; De Boer and Lopez, 2012), and most of these studies have been applied to either bacterial (Lang et al., 2010) or viral pathogens (Adams et al., 2009; Studholme et al., 2011). In this study, we used a comparative genomics strategy to develop species-specific molecular diagnostics for the obligate oomycete *P. cubensis*, a devastating downy mildew pathogen of cucurbit crops (Savory et al., 2011).

A draft *P. cubensis* genome was available for this study; however, this genome is not of finished quality (N50 contig size of 4.0 Kbp) (Savory et al., 2012a; Savory et al., 2012b). Nonetheless, our study highlights the usefulness of genomic data even in unfinished format for marker development, especially for obligate pathogens where genomic resources are scarce and obtaining adequate amounts of DNA for laboratory testing may be difficult (Baxter et al., 2010; Links et al., 2011). The RNA-seq data allowed us to identify diagnostic candidates with differential expression between *P. cubensis* and *P. humuli*, but conserved within each species, and thus, robust across isolates of these two frequently indistinguishable pathogens. The DNA-seq data allowed confirmation of presence or absence of an exon or a gene at the DNA level in *P. humuli*, since no genomic data is available for this pathogen. Prior knowledge of the genetic structure of *P. cubensis* and *P. humuli* (Mitchell et al., 2011; Quesada-Ocampo et al., 2012) informed our selection of diverse samples for sequencing and likely improved the efficient elimination of unsuitable candidates and increased validation success. The close relatedness between *P. cubensis* and *P. humuli* allowed for rapid identification of lineage-specific regions in *P. cubensis* that can be used for diagnostics, highlighting the importance of resolving phylogenetic relationships for development of robust diagnostics (Choi et al., 2005; Mitchell et al., 2011). Interestingly, several of the candidates identified had no significant sequence similarity to other organisms or informative functional annotation, while other candidates had gene functions that suggest that they may be related to stress (virulence), as has been observed for lineage-specific genes in plants (Campbell et al., 2007; Lin et al., 2010).

Since the diagnostic candidates were selected based on absence of an exon or a complete gene in *P. humuli*, we show that diagnostic assays can be implemented as conventional PCR-based diagnostics that detect presence of product, product size differences, and or potentially with serological assays. In this study, we pursued validation of diagnostic candidates through PCR methods since such assays can be readily adopted by Plant Disease Clinics as well as extension personnel, while serological methods frequently require adoption and commercialization (De Boer and Lopez, 2012). Nonetheless, since some of the diagnostic candidates identified in this study are present in *P. cubensis* but completely absent in *P. humuli* at the DNA level and potentially the protein level, they could be used for future development of serological-based diagnostics once monoclonal antibodies are developed for the *P. cubensis*-specific protein. A clear advantage of serological diagnostics is that it can be incorporated in field-friendly formats that can be used directly by growers, extension agents, and agricultural consultants, as is the case with the *Phytophthora* ImmunoStrip® (Adgia, Elkhart, Ind.) (De Boer and Lopez, 2012).

Figure 5:
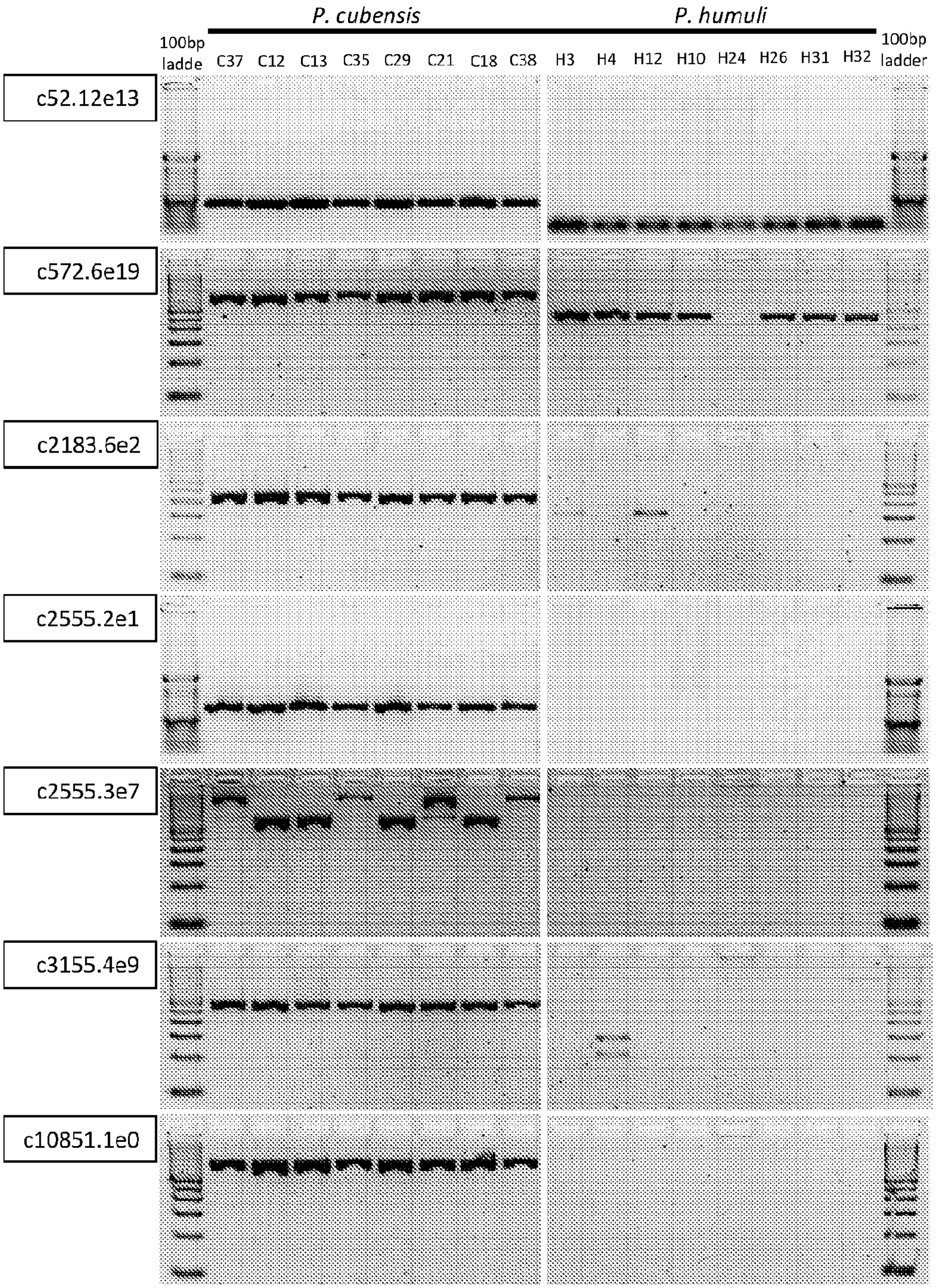
FIG. 5 provides gel electrophoresis images showing seven *P. cubensis* diagnostic candidate PCR products (c52.12e13, c572.6e19, c2183.6e2, c2555.2e1, c2555.3e7, c3155.4e9, c10851.1e0) for diverse cucurbit downy mildew (C37, C12, C13, C35, C29, C21, C18, C38) and hop downy mildew samples (H3, H4, H12, H10, H24, H26, H31, H32). See Table 2 for sample information and Table 5 for primer information. Diagnostic candidate codes corresponding to each gel are indicated on the left hand side of each gel image.

Accurate and timely identification of plant pathogens is the first step towards successful mitigation of crop diseases (De Boer and Lopez, 2012). In cucumber, downy mildew symptoms have very characteristic angular leaf spots delimited by leaf veins and profuse sporulation on the underside of the leaf, making diagnosis simple by visual means once the disease has >30% of severity on a leaf (Holmes et al., 2015) (see also, FIG. 1). However, diagnosis during early stages of infection when fungicide applications would be most effective, or in hosts such as watermelon were symptoms are nondescript, can be difficult and delay disease mitigation efforts (Holmes et al., 2015). Recently, *P. cubensis* was also reported to be seed borne as is the case with other downy mildew pathogens such as *P. belbahrii* (Cohen et al., 2014). The contribution of seed borne inoculum to yearly cucurbit downy mildew epidemics remains unclear but movement of infected plant material likely plays a role in *P. cubensis* population changes in the US (Cohen et al., 2014; Holmes et al., 2015). Molecular diagnostics could be used for detection of early infections or infected seed in combination with appropriate sampling strategies, which would prevent pathogen introduction into new regions (De Boer and Lopez, 2012). PCR assays with the seven nuclear genes identified in our study successfully detected *P. cubensis* in infected tissue of all plant hosts tested, including watermelon, which typically yields low quantities of pathogen DNA due to small lesions and poor sporulation of the pathogen on this host (FIG. 5).

Another common method for detection of oomycetes is the use of spore traps, which is especially useful for monitoring airborne inoculum of downy mildew pathogens since many species are spread via airborne sporangia (Gent et al., 2009; Granke et al., 2013; Klosterman et al., 2014).

In spore traps, pathogen sporangia are impacted on adhesive tape or grease covered rods on hourly, weekly, or daily time intervals that can later be stained and counted under a microscope (Jackson and Bayliss, 2011). In Michigan, a defined threshold of sporangia per week is used to determine when it is prudent to begin fungicide sprays for *P. cubensis* since sporangia concentrations are associated with the timing of downy mildew occurrence (Granke et al., 2014). A drawback of volumetric spore traps that has limited their deployment is the time and labor needed to enumerate sporangia (Granke and Hausbeck, 2011), and often morphological characters such as spore type and size overlap between closely related organisms (Runge et al., 2012). Limitations of tape-based spore traps have been addressed in other downy mildew pathogens by combining spore trapping with molecular detection and quantification of the pathogen (Gent et al., 2009; Klosterman et al., 2014). Due to its usefulness in identification of fungi and oomycetes, internal transcribed spacer (ITS) and other ribosomal DNA sequences have become common markers for diagnostics (Schoch et al., 2012), including for many of the downy mildew pathogens (Belbahri et al., 2005; Valsesia et al., 2005; Hukkanen et al., 2006; Gent et al., 2009; Zipper et al., 2009; Montes-Borrego et al., 2010; Mota et al., 2011; Ioos et al., 2012; Testen et al., 2013; Feng et al., 2014; Klosterman et al., 2014). However, in closely related species there may be insufficient variability in the ITS (Gent et al., 2009; Klosterman et al., 2014), or copy number variation (Martin, 1990; Belbahri et al., 2008) for useful delineation. Other assays utilizing locked nucleic acid probes and high resolution melt curve analysis can partially overcome this limitation, but add expense to the diagnostics (Summers et al., 2015). Two of the seven diagnostic markers identified in our study are putative single-copy markers (c2555.2e1 and c2555.3e7), making them attractive candidates for developing real-time PCR assays for *P. cubensis* inoculum monitoring efforts. Candidates c2555.2e1 and c2555.3e7 were also two of the three candidates that had no amplification in any *P. humuli* samples tested under the PCR conditions and using the primers designed in this study (FIG. 5).

Beyond the traditional use of plant disease diagnostics for agricultural decision-making, the need for rapid diagnostics has dramatically increased due to globalization of agricultural products (De Boer and Lopez, 2012). Losses due to invasive plant pathogens could be reduced if improved disease detection methods were available (De Boer and Lopez, 2012). For obligate parasites, such as downy mildew pathogens, development and validation of molecular assays may be complicated by lack of available genetic material, minimal sequence data to identify diagnostic markers, and unresolved phylogenetic status within the different genera (Thines et al., 2009). NGS and bioinformatics approaches allowed us to develop diagnostic markers that can differentiate *P. cubensis* from *P. humuli*. The approach detailed in this study also may also be amenable to identifying strains or pathotypes of *P. cubensis*. Similar approaches can also be applied to other plant pathogens with scarce genomic resources for rapid development of diagnostic markers.

REFERENCES

Adams et al. 2009. Next-generation sequencing and metagenomic analysis: a universal diagnostic tool in plant virology. Molecular Plant Pathology 10:537-545.

Altschul et al. 1990. Basic local alignment search tool. J Mol Biol 215:403-410.

Anders et al. 2015. HTSeq—a Python framework to work with high-throughput sequencing data. Bioinformatics 31:166-169.

Andrews, S. (2012). FastQC A Quality Control tool for High Throughput Sequence Data. In Babraham Bioinformatics (Babraham Institute).

Baxter, L., et al. 2010. Signatures of adaptation to obligate biotrophy in the Hyaloperonospora arabidopsidis genome. Science 330:1549-1551.

Belbahri et al. 2005. Phylogenetic analysis and real time PCR detection of a presumbably undescribed *Peronospora* species on sweet basil and sage. Mycol Res 109: 1276-1287.

Belbahri et al. 2008. Intraspecific and within-isolate sequence variation in the ITS rRNA gene region of *Pythium mercuriale* sp. nov. (Pythiaceae).

Campbell et al. 2007. Identification and Characterization of Lineage-Specific Genes within the Poaceae. Plant Physiology 145:1311-1322.

Choi et al. 2005. A re-consideration of *Pseudoperonospora cubensis* and *P. humuli* based on molecular and morphological data. Mycological Research 109:841-848.

Cohen, Y., Rubin, A. E., Galperin, M., Ploch, S., Runge, F., and Thines, M. 2014. Seed Transmission of *Pseudoperonospora cubensis*. PLoS ONE 9:e109766.

Cohen et al. 2015. Resurgence of *Pseudoperonospora cubensis*—the agent of cucurbit downy mildew. Phytopathology 105:998-1012.

De Boer, S. H., and Lopez, M. a. M. 2012. New Grower-Friendly Methods for Plant Pathogen Monitoring. Annual Review of Phytopathology 50:197-218.

Djalali Farahani-Kofoet, R., Romer, P., and Grosch, R. 2012. Systemic spread of downy mildew in basil plants and detection of the pathogen in seed and plant samples. Mycol Progress 11:961-966.

Feng et al. 2014. Multiplex real-time PCR assays for detection of four seedborne spinach pathogens. Journal of Applied Microbiology 117:472-484.

Fisher et al. 2012. Emerging fungal threats to animal, plant and ecosystem health. Nature 484:186-194.

Fry et al. 2015. Five Reasons to consider *Phytophthora infestans* a re-emerging pathogen. Phytopathology 105: 966-981.

Gascuel et al. 2015. The sunflower downy mildew pathogen *Plasmopara halstedii*. Molecular Plant Pathology 16:109-122.

Gent, D. H., and Ocamb, C. M. 2009. Predicting Infection Risk of Hop by *Pseudoperonspora humuli*. Phytopathology 99:1190-1198.

Gent et al. 2009. PCR detection of *Pseudoperonospora humuli* in air samples from hop yards. Plant Pathology 58:1081-1091.

Gent et al. 2015. Pre- and post-infection activity of fungicides in control of hop downy mildew. Plant Disease 99:858-865.

Granke, L. L., and Hausbeck, M. K. 2011. Dynamics of *Pseudoperonospora cubensis* Sporangia in Commercial Cucurbit Fields in Michigan. Plant Disease 95:1392-1400.

Granke, L. L., Morrice, J. J., and Hausbeck, M. K. 2013. Relationships Between Airborne *Pseudoperonospora cubensis* Sporangia, Environmental Conditions, and Cucumber Downy Mildew Severity. Plant Disease 98:674-681.

Granke, L. L., Morrice, J. J., and Hausbeck, M. K. 2014. Relationships between airborne *Pseudoperonospora cubensis* sporangia, environmental conditions, and cucumber downy mildew severity. Plant Dis. 98:674-681.

Greub et al. 2009. High Throughput Sequencing and Proteomics to Identify Immunogenic Proteins of a New Pathogen: The Dirty Genome Approach. PLoS ONE 4:e8423.

Hannon, G. (2010). FASTX Toolkit (Cold Spring Harbor Laboratory).

Holmes et al. 2015. Resurgence of Cucurbit Downy Mildew in the United States: A Watershed Event for Research and Extension. Plant Disease 99:428-441.

Homa et al. 2014. Evaluation of Fungicides for the Control of *Peronospora belbahrii* on Sweet Basil in New Jersey. Plant Disease 98:1561-1566.

Huang et al. 2009. The genome of the cucumber, *Cucumis sativus* L. Nat Genet 41:1275-1281.

Hukkanen et al. 2006. Quantification of downy mildew (*Peronospora sparsa*) in *Rubus* species using real-time PCR. Eur J Plant Pathol 116:225-235.

Ioos et al. 2012. An optimized duplex real-time PCR tool for sensitive detection of the quarantine oomycete *Plasmopara halstedii* in sunflower seeds. Phytopathology 102:908-917.

Jackson, S. L., and Bayliss, K. L. 2011. Spore traps need improvement to fulfil plant biosecurity requirements. Plant Pathology 60:801-810.

Klosterman et al. 2014. Coupling Spore Traps and Quantitative PCR Assays for Detection of the Downy Mildew Pathogens of Spinach (*Peronospora effusa*) and Beet (*P. schachtii*). Phytopathology 104:1349-1359.

Lang et al. 2010. Genomics-Based Diagnostic Marker Development for *Xanthomonas oryzae* pv. *oryzae* and *X. oryzae* pv. oryzicola. Plant Disease 94:311-319.

Langmead et al. 2009. Ultrafast and memory-efficient alignment of short DNA sequences to the human genome. Genome Biol 10:R25.

Links et al. 2011. De novo sequence assembly of *Albugo candida* reveals a small genome relative to other biotrophic oomycetes. BMC Genomics 12:503.

Martin, F. N. 1990. Variation in the ribosomal DNA repeat unit within single-oospore isolates of the genus *Pythium*. Genome 33:585-591.

Martin, F. N., Abad, Z. G., Balci, Y., and Ivors, K. 2012. Identification and Detection of *Phytophthora*: Reviewing Our Progress, Identifying Our Needs. Plant Disease 96:1080-1103.

Martin, M. 2012. Cutadapt removes adapter sequences from high-throughput sequencing reads. 50 Bioinformatics in Action 17:10-12.

Michelmore, R., and Wong, J. 2008. Classical and molecular genetics of *Bremia lactucae*, cause of lettuce downy mildew. Eur J Plant Pathol 122:19-30.

Mitchell et al. 2011. Genetic and Pathogenic Relatedness of *Pseudoperonospora cubensis* and *P. humuli*. Phytopathology 101:805-818.

Montes-Borrego, M., Munoz-Ledesma, F. J., Jimenez-Diaz, R. M., and Landa, B. B. 2010. Real-Time PCR Quantification of *Peronospora arborescens*, the Opium Poppy Downy Mildew Pathogen, in Seed Stocks and Symptomless Infected Plants. Plant Disease 95:143-152.

Mota, M., Caldeira, C., and Monteiro, A. A. 2011. Molecular detection of contaminating fungi in lettuce. Acta Horticulturae 917:217-223.

Ojiambo, P. S., Paul, P. A., and Holmes, G. J. 2010. A Quantitative Review of Fungicide Efficacy for Managing Downy Mildew in Cucurbits. Phytopathology 100:1066-1076.

Ojiambo et al. 2015. Epidemiology and Population Biology of *Pseudoperonospora cubensis*: A Model System for Management of Downy Mildews. Annual Review of Phytopathology 53:223-246.

Pallen, M. J., Loman, N. J., and Penn, C. W. 2010. High-throughput sequencing and clinical microbiology: progress, opportunities and challenges. Current Opinion in Microbiology 13:625-631.

Quesada-Ocampo et al. 2012. The genetic structure of *Pseudoperonospora cubensis* populations. Plant Dis. 96:1459-1470.

Roberts, P. D., Raid, R. N., Harmon, P. F., Jordan, S. A., and Palmateer, A. J. 2009. First Report of Downy Mildew Caused by a *Peronospora* sp. on Basil in Florida and the United States. Plant Disease 93:199-199.

Runge, F., and Thines, M. 2009. A potential perennial host for *Pseudoperonospora cubensis* in temperate regions. Eur J Plant Pathol 123:483-486.

Runge et al. 2012. Which Morphological Characteristics Are Most Influenced by the Host Matrix in Downy Mildews? A Case Study in *Pseudoperonospora cubensis*. PLoS ONE 7:e44863.

Savory et al. 2011. The cucurbit downy mildew pathogen *Pseudoperonospora cubensis*. Mol. Plant Pathol. 12:217-226.

Savory et al. 2012a. mRNA-Seq Analysis of the *Pseudoperonospora cubensis* Transcriptome During Cucumber (*Cucumis sativus* L.) Infection. PLoS ONE 7:e35796.

Savory et al. 2012b. Alternative Splicing of a Multi-Drug Transporter from *Pseudoperonospora cubensis* Generates an RXLR Effector Protein That Elicits a Rapid Cell Death. PLoS ONE 7:e34701.

Schoche et al. 2012. Nuclear ribosomal internal transcribed spacer (ITS) region as a universal DNA barcode marker for Fungi. Proceedings of the National Academy of Sciences 109:6241-6246.

Studholme, D. J., Glover, R. H., and Boonham, N. 2011. Application of High-Throughput DNA Sequencing in Phytopathology. Annual Review of Phytopathology 49:87-105.

Summers et al. 2015. *Pseudoperonospora cubensis* and *P. humuli* detection using species-specific probes and high definition melt curve analysis. Canadian Journal of Plant Pathology: 1-16.

Testen et al. 2013. Molecular Detection of *Peronospora variabilis* in *Quinoa* Seed and Phylogeny of the *Quinoa* Downy Mildew Pathogen in South America and the United States. Phytopathology 104:379-386.

Thines, M., Telle, S., Ploch, S., and Runge, F. 2009. Identity of the downy mildew pathogens of basil, *coleus*, and sage with implications for quarantine measures. Mycological Research 113:532-540.

Valsesia et al. 2005. Development of a High-Throughput Method for Quantification of *Plasmopara viticola* DNA in Grapevine Leaves by Means of Quantitative Real-Time Polymerase Chain Reaction. Phytopathology 95:672-678.

Zipper, R., Hammer, T., and Spring, O. 2009. PCR-based monitoring of recent isolates of tobacco blue mold from Europe reveals the presence of two genetically distinct phenotypes differing in fungicide sensitivity. Eur J Plant Pathol 123:367-375.

TABLE 1

*Pseudoperonospora cubensis* and *Pseudoperonospora humuli* isolates used for Illumina 50 bp single-end RNAseq and 100 bp paired-end DNAseq.

| Pathogen species | Isolate | Host | Location | Year collected | Source |
|---|---|---|---|---|---|
| *Pseudoperonospora cubensis* | CA08A1 | *Cucumis sativus* (Cucumber) | California | 2008 | Ojiambo |
| *P. cubensis* | SC1982 | *Cucumis melo* (Cantaloupe) | South Carolina | 1982 | Ojiambo |
| *P. cubensis* | NC2013C3 | *Cucurbita maxima* (Pumpkin) | North Carolina | 2013 | Ojiambo |
| *P. cubensis* | SC2013F2 | *Cucurbita pepo* (Acorn squash) | South Carolina | 2013 | Ojiambo |
| *P. cubensis* | NCA11 | Cucumber | North Carolina | 2012 | Ojiambo |
| *P. cubensis* | SCD3 | *Cucurbita moschata* (Butternut squash) | South Carolina | 2012 | Ojiambo |
| *P. cubensis* | NCWAY2-1 | Cucumber | North Carolina | 2013 | Quesada |
| *Pseudoperonospora humuli* | NY482CA | *Humulus lupulus* (Hop) | New York | 2011 | Gent |
| *P. humuli* | JP490-5 | *Humulus japonicus* (Japanese hop) | Aomori, Japan | 2012 | Gent |
| *P. humuli* | JP490 | Japanese hop | Aomori, Japan | 2012 | Gent |
| *P. humuli* | JP498SA | Japanese hop | Ehoro, Japan | 2012 | Gent |
| *P. humuli* | OR501BA | Hop | Oregon | 2013 | Gent |
| *P. humuli* | OR502AA* | Hop | Oregon | 2013 | Gent |
| *P. humuli* | VT503A3 | Hop | Virginia | 2013 | Gent |
| *P. humuli* | WI510-1 | Hop | Wisconsin | 2013 | Gent |

*Isolate also used for DNAseq

TABLE 2

*Peronospora belbahrii*,*Pseudoperonospora cubensis*, *Pseudoperonospora humuli*, *Plasmopara obducens*, *Phytophthora capsici*, and *Phytophthora infestans* isolates used for validation of *P. cubensis*-specific diagnostic candidates.

| Pathogen species or sample | Isolate | Host | Location | Year collected | Source |
|---|---|---|---|---|---|
| *Peronospora belbahrii* | B1 | *Ocimum basilicum* (Basil, sweet) | Clayton, North Carolina | 2014 | Quesada |
| *P. belbahrii* | B2 | Basil (Sweet) | Chapel Hill, North Carolina | 2014 | Quesada |
| *P. belbahrii* | B3 | Basil (Genovese) | Roxboro, North Carolina | 2014 | Quesada |
| *P. belbahrii* | B4 | Basil (Saim queen thai) | Chapel Hill, North Carolina | 2014 | Quesada |
| *P. belbahrii* | B5 | Basil (Genovese) | Chapel Hill, North Carolina | 2014 | Quesada |
| *Pseudoperonospora cubensis* | C1 | *Cucurbita moschata* (Butternut squash) | South Carolina | 2012 | Quesada |
| *P. cubensis* | C2 | *Cucumis sativus* (Cucumber) | Kinston, North Carolina | 2013 | Quesada |
| *P. cubensis* | C3 | Cucumber | Cleveland, North Carolina | 2013 | Quesada |
| *P. cubensis* | C4 | Cucumber | Kinston, North Carolina | 2013 | Quesada |

TABLE 2-continued

*Peronospora belbahrii*,*Pseudoperonospora cubensis*, *Pseudoperonospora humuli*, *Plasmopara obducens*, *Phytophthora capsici*, and *Phytophthora infestans* isolates used for validation of *P. cubensis*-specific diagnostic candidates.

| Pathogen species or sample | Isolate | Host | Location | Year collected | Source |
|---|---|---|---|---|---|
| *P. cubensis* | C5(L) | *Cucumis melo* (Cantaloupe) | Waynesville, North Carolina | 2013 | Quesada |
| *P. cubensis* | C6 | *Cucurbita pepo* (Acorn squash) | Kinston, North Carolina | 2013 | Quesada |
| *P. cubensis* | C7 | *Cucurbita maxima* (Pumpkin) | Waynesville, North Carolina | 2013 | Quesada |
| *P. cubensis* | C8 | Butternut squash | Kinston, North Carolina | 2013 | Quesada |
| *P. cubensis* | C9(L) | *Citrullus lanatus* (Watermelon) | Waynesville, North Carolina | 2013 | Quesada |
| *P. cubensis* | C10 | Butternut squash | Cleveland, North Carolina | 2013 | Quesada |
| *P. cubensis* | C11 | Pumpkin | Cleveland, North Carolina | 2013 | Quesada |
| *P. cubensis* | C12 | Cucumber | Waynesville, North Carolina | 2013 | Quesada |
| *P. cubensis* | C13(L) | Cantaloupe | Kinston, North Carolina | 2013 | Quesada |
| *P. cubensis* | C14 | Cucumber | Waynesville, North Carolina | 2013 | Quesada |
| *P. cubensis* | C15 | Cucumber | Cleveland, North Carolina | 2013 | Quesada |
| *P. cubensis* | C16 | Pumpkin | Cleveland, North Carolina | 2013 | Quesada |
| *P. cubensis* | C17 | Acorn squash | Kinston, North Carolina | 2013 | Quesada |
| *P. cubensis* | C18 | *Cucurbita foetidissima* (Buffalo gourd) | Waynesville, North Carolina | 2014 | Quesada |
| *P. cubensis* | C19 | Buffalo gourd | Waynesville, North Carolina | 2014 | Quesada |
| *P. cubensis* | C20 | Butternut squash | Kinston, North Carolina | 2013 | Quesada |
| *P. cubensis* | C21 | Butternut squash | Waynesville, North Carolina | 2013 | Quesada |
| *P. cubensis* | C22 | Butternut squash | Kinston, North Carolina | 2013 | Quesada |
| *P. cubensis* | C23(L) | Cantaloupe | Waynesville, North Carolina | 2013 | Quesada |
| *P. cubensis* | C24(L) | Cantaloupe | Cleveland, North Carolina | 2013 | Quesada |
| *P. cubensis* | C25(L) | Cantaloupe | Cleveland, North Carolina | 2013 | Quesada |
| *P. cubensis* | C26 | Cucumber | Cleveland, North Carolina | 2013 | Quesada |
| *P. cubensis* | C27 | Cucumber | Cleveland, North Carolina | 2013 | Quesada |
| *P. cubensis* | C28 | Cucumber | Cleveland, North Carolina | 2013 | Quesada |
| *P. cubensis* | C29 | Cucumber | Michigan | 2013 | Hausbeck |
| *P. cubensis* | C30 | Cucumber | Kinston, North Carolina | 2013 | Quesada |
| *P. cubensis* | C31 | Cucumber | Kinston, North Carolina | 2013 | Quesada |
| *P. cubensis* | C32 | Cucumber | Waynesville, North Carolina | 2013 | Quesada |
| *P. cubensis* | C33 | Cucumber | Waynesville, North Carolina | 2013 | Quesada |
| *P. cubensis* | C34 | Pumpkin | Kinston, North Carolina | 2013 | Quesada |
| *P. cubensis* | C35 | Pumpkin | Waynesville, North Carolina | 2013 | Quesada |
| *P. cubensis* | C36 | Pumpkin | Cleveland, North Carolina | 2013 | Quesada |
| *P. cubensis* | C37(L) | Watermelon | Cleveland, North Carolina | 2013 | Quesada |
| *P. cubensis* | C38(L) | Watermelon | Cleveland, North Carolina | 2013 | Quesada |
| *P. cubensis* | C39(L) | Watermelon | Cleveland, North Carolina | 2013 | Quesada |
| *P. cubensis* | C40(L) | Watermelon | Waynesville, North Carolina | 2013 | Quesada |
| *P. cubensis* | 1938(L) | Cucumber | New Jersey | 2007 | Hausbeck |
| *P. cubensis* | 1933(L) | Butternut squash | Puerto Rico | 2010 | Hausbeck |
| *P. cubensis* | 1155(L) | Butternut squash | Italy | 2003 | Hausbeck |
| *P. cubensis* | 1923(L) | Cucumber | Italy | 2009 | Hausbeck |
| *P. cubensis* | 1841(L) | Cucumber | Norway | 2009 | Hausbeck |
| *P. cubensis* | 1921(L) | Cucumber | Germany | 2007 | Hausbeck |
| *P. cubensis* | 1924(L) | Cucumber | Netherlands | 2001 | Hausbeck |
| *P. cubensis* | 1925(L) | Cucumber | Spain | 2001 | Hausbeck |
| *P. cubensis* | 1927(L) | Butternut squash | Spain | 2003 | Hausbeck |
| *Pseudoperonospora humuli* | H1 | *Humulus lupulus* (Hop) | Mills River, North Carolina | 2014 | Quesada |
| *P. humuli* | H2 | Hop | Mills River, North Carolina | 2014 | Quesada |
| *P. humuli* | H3 | Hop | Mills River, North Carolina | 2014 | Quesada |
| *P. humuli* | H4 | Hop | Oregon | 2012 | Gent |
| *P. humuli* | H5 | Hop | New York | 2011 | Gent |
| *P. humuli* | H6 | Hop | New York | 2011 | Gent |
| *P. humuli* | H7 | Hop | Virginia | 2013 | Gent |
| *P. humuli* | H8 | Hop | Oregon | 2013 | Gent |
| *P. humuli* | H9 | Hop | Oregon | 2013 | Gent |
| *P. humuli* | H10 | Hop | Japan | 2012 | Gent |
| *P. humuli* | H11 | Hop | Japan | 2012 | Gent |
| *P. humuli* | H12 | Hop | Mills River, North Carolina | 2014 | Quesada |
| *P. humuli* | H13 | Hop | Oregon | 2006 | Gent |
| *P. humuli* | H14 | Hop | Oregon | 2008 | Gent |
| *P. humuli* | H15 | Hop | Washington | 2008 | Gent |
| *P. humuli* | H16 | Hop | Oregon | 2008 | Gent |
| *P. humuli* | H17 | Hop | New York | 2013 | Gent |
| *P. humuli* | H18 | Hop | New York | 2013 | Gent |
| *P. humuli* | H19 | Hop | Virginia | 2013 | Gent |
| *P. humuli* | H20 | Hop | Czech Republic | 2012 | Gent |
| *P. humuli* | H21 | Hop | New York | 2011 | Gent |
| *P. humuli* | H22 | Hop | Oregon | 2011 | Gent |
| *P. humuli* | H23 | Hop | Mills River, North Carolina | 2014 | Quesada |
| *P. humuli* | H24 | Hop | Mills River, North Carolina | 2014 | Quesada |
| *P. humuli* | H25 | Hop | New York | 2011 | Gent |
| *P. humuli* | H26 | Hop | Oregon | 2013 | Gent |
| *P. humuli* | H27 | Hop | Aomori, Japan | 2012 | Gent |
| *P. humuli* | H28 | Hop | Oregon | 2013 | Gent |

TABLE 2-continued

*Peronospora belbahrii*,*Pseudoperonospora cubensis*, *Pseudoperonospora humuli*, *Plasmopara obducens*, *Phytophthora capsici*, and *Phytophthora infestans* isolates used for validation of *P. cubensis*-specific diagnostic candidates.

| Pathogen species or sample | Isolate | Host | Location | Year collected | Source |
|---|---|---|---|---|---|
| *P. humuli* | H29 | Hop | Oregon | 2007 | Gent |
| *P. humuli* | H30 | Hop | Oregon | 2008 | Gent |
| *P. humuli* | H31 | Hop | Washington | 2008 | Gent |
| *P. humuli* | H32 | Hop | New York | 2013 | Gent |
| *P. humuli* | H33 | Hop | Washington | 2006 | Gent |
| *P. humuli* | H34 | Hop | Oregon | 2008 | Gent |
| *Plasmopara obducens* | I1 | *Impatiens walleriana* (Impatiens) | Michigan | 2014 | Hausbeck |
| *P. obducens* | I2 | *Impatiens* | Michigan | 2014 | Hausbeck |
| *P. obducens* | I3 | *Impatiens* | Michigan | 2014 | Hausbeck |
| *Phytophthora capsici* | P1(M) | Watermelon | North Carolina | 2014 | Quesada |
| *P. capsici* | P2(M) | *Capsicum annuum* (Pepper) | NA | NA | Ristaino |
| *P. capsici* | P3(M) | *Cucurbita pepo* (Zucchinni) | South Carolina | NA | Ristaino |
| *P. capsici* | P4(M) | Watermelon | South Carolina | NA | Ristaino |
| *P. capsici* | P5(M) | Pepper | Michigan | NA | Hausbeck |
| *P. capsici* | P6(M) | Pumpkin | Michigan | NA | Hausbeck |
| *Phytophthora infestans* | Pi1(M) | *Solanum tuberosum* (Potato) | Pennsylvania | 2009 | Ristaino |
| *P. infestans* | Pi2(M) | Potato | North Carolina | 1994 | Ristaino |
| *P. infestans* | Pi3(M) | *Solanum lycopersicum* (Tomato) | California | 1998 | Ristaino |
| *P. infestans* | Pi4(M) | Tomato | Pennsylvania | 2009 | Ristaino |
| *P. infestans* | Pi5(M) | Tomato | North Carolina | 2009 | Ristaino |
| *P. infestans* | Pi6(M) | Tomato | Virginia | 2009 | Ristaino |
| *P. infestans* | Pi7(M) | Potato | North Dakota | 2010 | Ristaino |
| *P. infestans* | Pi8(M) | Potato | North Dakota | 2009 | Ristaino |

(L) Infected lesion sample with low or no sporulation
(M) Mycelia sample, other samples are lesions

TABLE 3

Plant hosts used for validation of *Pseudoperonospora cubensis*-specific diagnostic candidates.

| Host species | Common name | Cultivar |
|---|---|---|
| *Cucumis sativus* | Cucumber | Straight 8 |
| *Cucumis melo* | Cantaloupe | Hale's Best Jumbo |
| *Cucurbita pepo* | Acorn squash | Table Queen |
| *Cucurbita maxima* | Pumpkin | Big Max |
| *Cucurbita moschata* | Butternut squash | Waltham Butternut |

TABLE 3-continued

Plant hosts used for validation of *Pseudoperonospora cubensis*-specific diagnostic candidates.

| Host species | Common name | Cultivar |
|---|---|---|
| *Citrullus lanatus* | Watermelon | Mickey Lee |
| *Ocimum basilicum* | Basil | Sweet Basil |
| *Humulus lupulus* | Hop | Pacific Gem |

TABLE 4

Summary of quality control analysis for *Pseudoperonospora cubensis* and *Pseudoperonospora humuli* samples used for Illumina 50 bp single-end RNAseq and 100 bp paired-end DNAseq.

| Pathogen species | Isolate | Molecule | Sequencing mode | Number of total reads | Number of high quality reads | Reads mapped to *Pseudoperonospora cubensis* (%) | Reads mapped to *Cucumis sativus* (%) |
|---|---|---|---|---|---|---|---|
| *Pseudoperonospora cubensis* | CA08A1 | RNA | SE | 23,691,206 | 23,576,348 | 92.96 | 0.49 |
| *P. cubensis* | SC1982 | RNA | SE | 22,117,725 | 22,049,442 | 93.6 | 6.24 |
| *P. cubensis* | NC2013C3 | RNA | SE | 28,035,867 | 27,888,243 | 87.98 | 0.62 |
| *P. cubensis* | SC2013F2 | RNA | SE | 16,956,357 | 16,886,934 | 79.89 | 5.8 |
| *P. cubensis* | NCA11 | RNA | SE | 28,101,878 | 27,962,061 | 88.33 | 0.62 |
| *P. cubensis* | SCD3 | RNA | SE | 29,304,711 | 29,218,196 | 95.08 | 4.26 |
| *P. cubensis* | NCWAY2-1 | RNA | SE | 21,038,800 | 20,974,369 | 94.58 | 6.7 |
| *Pseudoperonospora humuli* | NY482CA | RNA | SE | 15,906,769 | 15,860,532 | 91.45 | 7.54 |
| *P. humuli* | JP490-5 | RNA | SE | 20,211,068 | 20,149,698 | 92.12 | 4.58 |
| *P. humuli* | JP490 | RNA | SE | 11,942,671 | 11,913,949 | 66.91 | 6.45 |
| *P. humuli* | JP498SA | RNA | SE | 26,977,356 | 26,866,989 | 90.01 | 0.54 |
| *P. humuli* | OR501BA | RNA | SE | 14,429,953 | 14,399,612 | 88.53 | 5.55 |
| *P. humuli* | OR502AA* | RNA | SE | 26,193,148 | 26,086,672 | 92.28 | 0.51 |
| *P. humuli* | VT503A3 | RNA | SE | 14,576,962 | 14,543,704 | 91.75 | 5.69 |
| *P. humuli* | WI510-1 | RNA | SE | 29,264,282 | 29,150,378 | 88.78 | 0.68 |
| *P. humuli* | OR502AA_R1* | DNA | PE | 36,599,100 | 21,778,230 | 97.46 | 12.02 |
| *P. humuli* | OR502AA_R2* | DNA | PE | 36,599,100 | 21,778,230 | 95.99 | 13.2 |

*Isolate also used for DNAseq paired-end sequencing but reads were aligned to the *P. cubensis* genome as single-end reads (R1 and R2).

TABLE 5

Candidate code, gene identifier, gene functional annotation, primers, and expected product sizes for final *Pseudoperonospora cubensis*-specific diagnostic candidates identified in this study.

| Candidate code[a] | Gene identifier | Functional annotation | Forward primer | Reverse primer | Product size |
|---|---|---|---|---|---|
| c52.12e13 | maker-pcu_contig_52-snap-gene-0.12-mRNA-1:exon:13 | Crinkler CRN family protein | ATTTCACCTTAGAGTCACGGC | CGGCCATCAACTCGTATCTC | 486 |
| c572.6e19 | maker-pcu_contig_572-snap-gene-0.6-mRNA-1:exon:19 | Gene of unknown function | GGAGACACGACAACAAATGCAG | TGCGCGGCAAGAATTTAGG | 854 |
| c2183.6e2 | snap_masked-pcu_contig_2183-abinit-gene-0.6-mRNA-1:exon | Conserved gene of unknown function | ATGCAGCGGGTATCCTTCC | CACGAAGAAGCAGGAAATGC | 448 |
| c2555.2e1 (S) | maker-pcu_contig_2555-snap-gene-0.2-mRNA-1:exon:1 | Gene of unknown function | CGCGCAACCTTGAATACCTAC | CACCCGCTCGCAGTAATGAC | 831 |
| c2555.3e7 (S) | maker-pcu_contig_2555-snap-gene-0.3-mRNA-1:exon:7 | Gene of unknown function | GACGCAACCCAGCATAACAAG | TGCGCTCGAGTATCTTCTACC | 787 |
| c3155.4e9 | maker-pcu_contig_3155-snap-gene-0.4-mRNA-1:exon:9 | Gene of unknown function | TCATCACCATATCCGCTTCCTG | TGCGTGAATGCTGTGCGAC | 595 |
| c10851.1e0 | maker-pcu_contig_10851-snap-gene-0.1-mRNA-1:exon:0 | NPP1 | CAGTTCTCGATTTCCCTCGTC | CTCTACTCACAAGATCTGCCAC | 867 |

[a](S) Putative single-copy gene according to self-BLASTP analyses

TABLE 6

Candidate code, gene identifier, exon content, gene functional annotation, validation results, primers, and expected product sizes of genes containing exons expressed in *Pseudoperonospora cubensis* isolates but not in *Pseudoperonospora humuli* isolates.

| Candidate code | Gene identifier | Exon | Functional annotation | Functional annotation using an oomycete protein database (D) | Validation results | Forward primer | Reverse primer | Product size |
|---|---|---|---|---|---|---|---|---|
| c52.12e13 SEQ ID NO: 39 | maker-pcu_contig_52-snap-gene-0.12-mRNA-1:exon:13 | 13 | Crinkler CRN family protein | crinkler (CRN) family protein, partial [*Phytophthora infestans* T30-4] | Final diagnostic candidate | ATTTCACCTTAGAGTCACGGC | CGGCCATCAACTCGTATCTC | 486 |
| c572.6e19 SEQ ID NO: 43 | maker-pcu_contig_572-snap-gene-0.6-mRNA-1:exon:19 | 19 | Gene of unknown function | Expressed gene of unknown function | Final diagnostic candidate | GGAGACACGACAACAAATGCAG | TGCGCGGCAAGAATTTAGG | 854 |
| c572.6e20 SEQ ID NO: 43 | maker-pcu_contig_572-snap-gene-0.6-mRNA-1:exon:20 | 20* | Gene of unknown function | Expressed gene of unknown function | * | | | |
| c572.6e21 SEQ ID NO: 43 | maker-pcu_contig_572-snap-gene-0.6-mRNA-1:exon:21 | 21* | Gene of unknown function | Expressed gene of unknown function | * | | | |
| c572.6e22 SEQ ID NO: 43 | maker-pcu_contig_572-snap-gene-0.6-mRNA-1:exon:22 | 22* | Gene of unknown function | Expressed gene of unknown function | * | | | |
| c2183.6e2 SEQ ID NO: 13 | snap_masked-pcu contig_2183-abinit-gene-0.6-mRNA-1:exon:2 | 2 | Conserved gene of unknown function | conserved hypothetical protein [*Phytophthora infestans* T30-4] | Final diagnostic candidate | ATGCAGCGGGTATCCTTCC | CACGAAGAAGCAGGAAATGC | 448 |
| c2555.2e1 SEQ ID NO: 17 | maker-pcu_contig_2555-snap-gene-0.2-mRNA-1:exon:1 | 1 (S) | Gene of unknown function | Expressed gene of unknown function | Final diagnostic candidate | CGCGCAACCTTGAATACCTAC | CACCCGCTCGCAGTAATGAC | 831 |

TABLE 6-continued

Candidate code, gene identifier, exon content, gene functional annotation, validation results, primers, and expected product sizes of genes containing exons expressed in *Pseudoperonospora cubensis* isolates but not in *Pseudoperonospora humuli* isolates.

| Candidate code | Gene identifier | Exon | Functional annotation | Functional annotation using an oomycete protein database (D) | Validation results | Forward primer | Reverse primer | Product size |
|---|---|---|---|---|---|---|---|---|
| c2555.3e7 SEQ ID NO: 16 | maker-pcu_contig_2555-snap-gene-0.3-mRNA-1:exon:7 | 7 (S) | Gene of unknown function | Expressed gene of unknown function | Final diagnostic candidate | GACGCAACCCAGCATAACAAG | TGCGCTCGAGTATCTTCTACC | 787 |
| c3155.4e9 SEQ ID NO: 24 | maker-pcu_contig_3155-snap-gene-0.4-mRNA-1:exon:9 | 9 | Gene of unknown function | Expressed gene of unknown function | Final diagnostic candidate | TCATCACCATATCCGCTTCCTG | TGCGTGAATGCTGTGCGAC | 595 |
| c10851.1e0 SEQ ID NO: 2 | maker-pcu_contig_10851-snap-gene-0.1-mRNA-1:exon:0 | 0 | NPP1 | necrosis inducing protein NPP2 [*Phytophthora capsici*] | Final diagnostic candidate | CAGTTCTCGATTTCCCTCGTC | CTCTACTCACAAGATCTGCCAC | 867 |
| c5367.0e0 SEQ ID NO: 40 | maker-pcu_contig_5367-snap-gene-0.0-mRNA-1:exon:0 | 0 | Aldose 1-epimerase | aldose 1-epimerase, putative [*Phytophthora infestans* T30-4] | Similar product in *P. obducens* | ATTGTTGCGGATGTCGTGG | CACCAATTCACCGATTCCAGAG | 611 |
| c11460.0e0 SEQ ID NO: 6 | maker-pcu_contig_11460-snap-gene-0.0-mRNA-1:exon:0 | 0 | NPP1 | NPP1-like protein [*Phytophthora infestans* T30-4] | Similar product in *P. humuli* | GCGTCACAAGCAACCAAGAG | AAAAGCTGCCACTCGAGC | 858 |
| c12435.0e1 SEQ ID NO: 7 | maker-pcu_contig_12435-snap-gene-0.0-mRNA-1:exon: 1 | 1 | Folate-Biopterin Transporter (FBT) Family | Folate-Biopterin Transporter FBT Family [*Phytophthora infestans* T30-4] | Similar product in *P. humuli* | ACTGCGACGGCATAAATCG | AACCTAGTGCAACCACCGC | 697 |
| c23803.0e0 SEQ ID NO: 14 | maker-pcu_contig_23803-snap-gene-0.0-mRNA-1:exon:0 | 0 | Polyprotein | pol protein [*Phytophthora infestans*] | Similar product in *P. humuli* | TACGCTTTGTTCCGGACGC | ACACTTTTCGGTACCCTTCGC | 427 |

TABLE 6-continued

Candidate code, gene identifier, exon content, gene functional annotation, validation results, primers, and expected product sizes of genes containing exons expressed in *Pseudoperonospora cubensis* isolates but not in *Pseudoperonospora humuli* isolates.

| Candidate code | Gene identifier | Exon | Functional annotation | Functional annotation using an oomycete protein database (D) | Validation results | Forward primer | Reverse primer | Product size |
|---|---|---|---|---|---|---|---|---|
| c2555.4e5 SEQ ID NO: 18 | maker-pcu_contig_2555-snap-gene-0.4-mRNA-1:exon:5 | 5 | Gene of unknown function | chromodomain protein, putative [*Phytophthora infestans* T30-4] | Similar product in *P. humuli* | AGATGGTCGAGAAGATACGTGG | ATCCGCGTTGCTATTGCTTG | 783 |
| c2982.0e0 SEQ ID NO: 22 | maker-pcu_contig_2982-snap-gene-0.0-mRNA-1:exon:0 | 0 | Glycoprotein elicitor | transglutaminase elicitor M81C [*Phytophthora infestans*] | Similar product in *P. humuli* | AGGTGCAATGGTCGAAGTCG | TTCCTTGTCTGACGCCCGTG | 618 |
| c2982.0e1 SEQ ID NO: 22 | maker-pcu_contig_2982-snap-gene-0.0-mRNA-1:exon:1 | 1* | Glycoprotein elicitor | transglutaminase elicitor M81C [*Phytophthora infestans*] | * | | | |
| c2982.0e2 SEQ ID NO: 22 | maker-pcu_contig_2982-snap-gene-0.0-mRNA-1:exon:2 | 2* | Glycoprotein elicitor | transglutaminase elicitor M81C [*Phytophthora infestans*] | * | | | |
| c364.4e2 SEQ ID NO: 30 | maker-pcu_contig_364-snap-gene-0.4-mRNA-1:exon:2 | 2 | Hypothetical polyprotein | Expressed gene of unknown function humuli | Similar *product* in *P.* | GGGCTTGGCGATTGTGC | CTGAAACCCCACTCCACCAC | 940 |
| c5000.0e0 SEQ ID NO: 35 | maker-pcu_contig_5000-snap-gene-0.0-mRNA-1:exon:0 | 0(S) | Gene of unknown function | Expressed gene of unknown function | Similar product in *P. humuli* | TCCACACCAGCTCGATACACG | ATTGACAGCACTTCGGCGG | 1160 |
| c5000.0e3 SEQ ID NO: 35 | maker-pcu_contig_5000-snap-gene-0.0-mRNA-1:exon:3 | 3* | Gene of unknown function | Expressed gene of unknown function | * | | | |

TABLE 6-continued

Candidate code, gene identifier, exon content, gene functional annotation, validation results, primers, and expected product sizes of genes containing exons expressed in *Pseudoperonospora cubensis* isolates but not in *Pseudoperonospora humuli* isolates.

| Candidate code | Gene identifier | Exon | Functional annotation | Functional annotation using an oomycete protein database (D) | Validation results | Forward primer | Reverse primer | Product size |
|---|---|---|---|---|---|---|---|---|
| c5000.0e4 SEQ ID NO: 35 | maker-pcu_contig_5000-snap-gene-0.0-mRNA-1:exon:4 | 4* | Gene of unknown function | Expressed gene of unknown function | * | | | |
| c5000.0e5 SEQ ID NO: 35 | maker-pcu_contig_5000-snap-gene-0.0-mRNA-1:exon:5 | 5* | Gene of unknown function | Expressed gene of unknown function | * | | | |
| c8214.1e1 SEQ ID NO: 49 | maker-pcu_contig_8214-snap-gene-0.1-mRNA-1:exon:1 | 1 | Gene of unknown function | Expressed gene of unknown function | Similar product in *P. humuli* | ATGCGTCTAAGGGTGCTACG | CAGCAACGCCAAGCCAAC | 584 |
| c8214.1e2 SEQ ID NO: 49 | maker-pcu_contig_8214-snap-gene-0.1-mRNA-1:exon:2 | 2* | Gene of unknown function | Expressed gene of unknown function | * | | | |
| c8214.1e3 SEQ ID NO: 49 | maker-pcu_contig_8214-snap-gene-0.1-nnRNA-1:exon:3 | 3* | Gene of unknown function | Expressed gene of unknown function | * | | | |
| c10864.0e2 SEQ ID NO: 4 | maker-pcu_contig_10864-snap-gene-0.0-mRNA-1:exon:2 | 2 | Gene of unknown function | Expressed gene of unknown function | In *P. humuli* DNAseq | | | |
| c10864.1e5 SEQ ID NO: 3 | maker-pcu_contig_10864-snap-gene-0.1-mRNA-1:exon:5 | 5 | Gene of unknown function | Expressed gene of unknown function | In *P. humuli* DNAseq | | | |

TABLE 6-continued

Candidate code, gene identifier, exon content, gene functional annotation, validation results, primers, and expected product sizes of genes containing exons expressed in *Pseudoperonospora cubensis* isolates but not in *Pseudoperonospora humuli* isolates.

| Candidate code | Gene identifier | Exon | Functional annotation | Functional annotation using an oomycete protein database (D) | Validation results | Forward primer | Reverse primer | Product size |
|---|---|---|---|---|---|---|---|---|
| c11281.1e0 SEQ ID NO: 5 | maker-pcu_contig_11281-snap-gene-0.1-mRNA-1:exon:0 | 0 | Multiple inositol polyphosphate phosphatase 1 | multiple inositol polyphosphate phosphatase 1, putative [*Phytophthora infestans* T30-4] | In *P. humuli* DNAseq | | | |
| c13498.0e0 SEQ ID NO: 9 | maker-pcu_contig_13498-snap-gene-0.0-mRNA-1:exon:0 | 0 | Conserved gene of unknown function | conserved hypothetical protein [*Phytophthora infestans* T30-4] | In *P. humuli* DNAseq | | | |
| c13981.0e1 SEQ ID NO: 10 | maker-pcu_contig_13981-snap-gene-0.0-mRNA-1:exon:1 | 1 | Transmembrane protein | conserved hypothetical protein [*Phytophthora infestans* T30-4] | In *P. humuli* DNAseq | | | |
| c2539.0e0 SEQ ID NO: 15 | maker-pcu_contig_2539-snap-gene-0.0-mRNA-1:exon:0 | 0 | Gene of unknown function | Expressed gene of unknown function | In *P. humuli* DNAseq | | | |
| c2539.0e1 SEQ ID NO: 15 | maker-pcu_contig_2539-snap-gene-0.0-mRNA-1:exon:1 | 1* | Gene of unknown function | Expressed gene of unknown function | * | | | |
| c26701.0e1 SEQ ID NO: 19 | maker-pcu_contig_26701-snap-gene-0.0-mRNA-1:exon:1 | 1 | Gene of unknown function | Expressed gene of unknown function | In *P. humuli* DNAseq | | | |
| c2955.2e0 SEQ ID NO: 21 | maker-pcu_contig_2955-snap-gene-0.2-mRNA-1:exon:0 | 0 | Gene of unknown function | putative polyprotein [*Phytophthora infestans*] | In *P. humuli* DNAseq | | | |

TABLE 6-continued

Candidate code, gene identifier, exon content, gene functional annotation, validation results, primers, and expected product sizes of genes containing exons expressed in *Pseudoperonospora cubensis* isolates but not in *Pseudoperonospora humuli* isolates.

| Candidate code | Gene identifier | Exon | Functional annotation | Functional annotation using an oomycete protein database (D) | Validation results | Forward primer | Reverse primer | Product size |
|---|---|---|---|---|---|---|---|---|
| c2955.2e1 SEQ ID NO: 21 | maker-pcu_contig_2955-snap-gene-0.2-mRNA-1:exon:1 | 1* | Gene of unknown function | putative polyprotein [*Phytophthora infestans*] | * | | | |
| c3294.1e2 SEQ ID NO: 26 | maker-pcu_contig_3294-snap-gene-0.1-mRNA-1:exon:2 | 2 (S) | Dumpy CG33196-PB | conserved hypothetical protein [*Phytophthora infestans* T30-4] | In *P. humuli* DNAseq | | | |
| c34577.0e0 SEQ ID NO: 29 | maker-pcu_contig_34577-snap-gene-0.0-mRNA-1:exon:0 | 0 | Polyprotein | putative polyprotein [*Phytophthora infestans*] | In *P. humuli* DNAseq | | | |
| c5000.1e6 SEQ ID NO: 34 | maker-pcu_contig_5000-snap-gene-0.1-mRNA-1:exon:6 | 6 | Cleavage induced predicted protein | cleavage induced predicted protein [*Phytophthora infestans* T30-4] | In *P. humuli* DNAseq | | | |
| c5001.0e0 SEQ ID NO: 36 | maker-pcu_contig_5001-snap-gene-0.0-mRNA-1:exon:0 | 0 | Gene of unknown function | Expressed gene of unknown function | In *P. humuli* DNAseq | | | |
| c5058.0e0 SEQ ID NO: 38 | maker-pcu_contig_5058-snap-gene-0.0-mRNA-1:exon:0 | 0 | Conserved gene of unknown function | conserved hypothetical protein [*Phytophthora infestans* T30-4] | In *P. humuli* DNAseq | | | |
| c5058.0e1 SEQ ID NO: 38 | maker-pcu_contig_5058-snap-gene-0.0-mRNA-1:exon:1 | 1* | Conserved gene of unknown function | conserved hypothetical protein [*Phytophthora infestans* T30-4] | | | | |

TABLE 6-continued

Candidate code, gene identifier, exon content, gene functional annotation, validation results, primers, and expected product sizes of genes containing exons expressed in *Pseudoperonospora cubensis* isolates but not in *Pseudoperonospora humuli* isolates.

| Candidate code | Gene identifier | Exon | Functional annotation | Functional annotation using an oomycete protein database (D) | Validation results | Forward primer | Reverse primer | Product size |
|---|---|---|---|---|---|---|---|---|
| c5058.0e2 SEQ ID NO: 38 | maker-pcu_contig_5058-snap-gene-0.0-mRNA-1:exon:2 | 2* | Conserved gene of unknown function | conserved hypothetical protein [*Phytophthora infestans* T30-4] | | | | |
| c5058.1e3 SEQ ID NO: 37 | maker-pcu_contig_5058-snap-gene-0.1-mRNA-1:exon:3 | 3 | Gene of unknown function | Expressed gene of unknown function | In *P. humuli* DNAseq | * | | |
| c5058.1e4 SEQ ID NO: 37 | maker-pcu_contig_5058-snap-gene-0.1-mRNA-1:exon:4 | 4* | Gene of unknown function | Expressed gene of unknown function | * | | | |
| c5058.1e5 SEQ ID NO: 37 | maker-pcu_contig_5058-snap-gene-0.1-mRNA-1:exon:5 | 5* | Gene of unknown function | Expressed gene of unknown function | * | | | |
| c5504.2e1 SEQ ID NO: 41 | maker-pcu_contig_5504-snap-gene-0.2-mRNA-1:exon:1 | 1 (S) | Multidrug FOligosaccharidyl-lipid Fpolysaccharide MOP Flippase Superfamily | Multidrug/Oligosaccharidyl-lipid/Polysaccharide (MOP) Flippase Superfamily [*Phytophthora infestans* T30-4] | In *P. humuli* DNAseq | | | |
| c5799.1e2 SEQ ID NO: 44 | maker-pcu_contig_5799-snap-gene-0.1-mRNA-1:exon:2 | 2 | Ubiquitin-conjugating enzyme E2 | ubiquitin-conjugating enzyme E2, putative [*Phytophthora infestans* T30-4] | In *P. humuli* DNAseq | | | |
| c6122.2e0 SEQ ID NO: 45 | maker-pcu_contig_6122-snap-gene-0.2-mRNA-1:exon:0 | 0 | Polygalacturonase | polygalacturonase [*Phytophthora capsici*] | In P. *humuli* DNAseq | | | |

TABLE 6-continued

Candidate code, gene identifier, exon content, gene functional annotation, validation results, primers, and expected product sizes of genes containing exons expressed in *Pseudoperonospora cubensis* isolates but not in *Pseudoperonospora humuli* isolates.

| Candidate code | Gene identifier | Exon | Functional annotation | Functional annotation using an oomycete protein database (D) | Validation results | Forward primer | Reverse primer | Product size |
|---|---|---|---|---|---|---|---|---|
| c6944.1e0 SEQ ID NO: 46 | maker-pcu_contig_6944-snap-gene-0.1-mRNA-1:exon:0 | 0 | Conserved gene of unknown function | conserved hypothetical protein [*Phytophthora infestans* T30-4] | In *P. humuli* DNAseq | | | |
| c6944.1e1 SEQ ID NO: 46 | maker-pcu_contig_6944-snap-gene-0.1-mRNA-1:exon:1 | 1* | Conserved gene of unknown function | conserved hypothetical protein [*Phytophthora infestans* T30-4] | * | | | |
| c7215.0e0 SEQ ID NO: 47 | maker-pcu_contig_7215-snap-gene-0.0-mRNA-1:exon:0 | 0 | Conserved gene of unknown function | conserved hypothetical protein [*Phytophthora infestans* T30-4] | In *P. humuli* DNAseq | | | |
| c7215.1e2 SEQ ID NO: 48 | maker-pcu_contig_7215-snap-gene-0.1-mRNA-1:exon:2 | 2 | Retrotransposon protein unclassified | conserved hypothetical protein [*Phytophthora infestans* T30-4] | In *P. humuli* DNAseq | | | |
| c7215.1e5 SEQ ID NO: 48 | maker-pcu_contig_7215-snap-gene-0.1-mRNA-1:exon:5 | 5* | Retrotransposon protein unclassified | conserved hypothetical protein [*Phytophthora infestans* T30-4] | * | | | |
| c962.4e3 SEQ ID NO: 51 | maker-pcu_contig_962-snap-gene-0.4-mRNA-1:exon:3 | 3 | Conserved gene of unknown function | hypothetical protein PITG_14255 [*Phytophthora infestans* T30-4] | In *P. humuli* DNAseq | | | |
| c10522.0e0 SEQ ID NO: 1 | maker-pcu_contig_10522-fgenesh-gene-0.0-mRNA-1:exon:0 | 0 | Elicitin RAL13E | putative GPI-anchored serine rich elicitin SOL13E-like protein [*Phytophthora infestans* T30-4] | NA | | | |

TABLE 6-continued

Candidate code, gene identifier, exon content, gene functional annotation, validation results, primers, and expected product sizes of genes containing exons expressed in *Pseudoperonospora cubensis* isolates but not in *Pseudoperonospora humuli* isolates.

| Candidate code | Gene identifier | Exon | Functional annotation | Functional annotation using an oomycete protein database (D) | Validation results | Forward primer | Reverse primer | Product size |
|---|---|---|---|---|---|---|---|---|
| c12575.0e0 SEQ ID NO: 8 | maker-pcu_contig_12575-snap-gene-0.0-mRNA-1:exon:0 | 0 | Conserved gene of unknown function | conserved hypothetical protein [*Phytophthora infestans* T30-4] | NA | | | |
| c12575.0e1 SEQ ID NO: 8 | maker-pcu_contig_12575-snap-gene-0.0-mRNA-1:exon:1 | 1* | Conserved gene of unknown function | conserved hypothetical protein [*Phytophthora infestans* T30-4] | * | | | |
| c2129.2e6 SEQ ID NO: 11 | maker-pcu_contig_2129-snap-gene-0.2-mRNA-1:exon:6 | 6 | Conserved gene of unknown function | conserved hypothetical protein [*Phytophthora infestans* T30-4] | NA | | | |
| c2163.6e5 SEQ ID NO: 12 | maker-pcu_contig_2163-snap-gene-0.6-mRNA-1:exon:5 | 5 | Gamma-butyrobetaine dioxygenase | trimethyllysine dioxygenase, putative [*Phytophthora infestans* T30-4] | NA | | | |
| c27478.0e0 SEQ ID NO: 20 | maker-pcu_contig_27478-snap-gene-0.0-mRNA-1:exon:0 | 0 | Gene of unknown function | RxLR effector candidate protein, partial<br><br>arabidopsidis Emoy2+ | NA | | | |
| c30239.0e0 SEQ ID NO: 23 | maker-pcu_contig_30239-snap-gene-0.0-mRNA-1:exon:0 | 0 | Gene of unknown function | aldose 1-epimerase, putative [*Phytophthora infestans* T30-4] | NA | | | |
| c31609.0e0 SEQ ID NO: 25 | maker-pcu_contig_31609-snap-gene-0.0-mRNA-1:exon:0 | 0 | Protein kinase | protein kinase [*Phytophthora infestans* T30-4] | NA | | | |

TABLE 6-continued

Candidate code, gene identifier, exon content, gene functional annotation, validation results, primers, and expected product sizes of genes containing exons expressed in *Pseudoperonospora cubensis* isolates but not in *Pseudoperonospora humuli* isolates.

| Candidate code | Gene identifier | Exon | Functional annotation | Functional annotation using an oomycete protein database (D) | Validation results | Forward primer | Reverse primer | Product size |
|---|---|---|---|---|---|---|---|---|
| c3294.1e3 SEQ ID NO: 26 | maker-pcu_contig_3298-snap-gene-0.1-mRNA-1:exon:3 | 3 | Gene of unknown function | Expressed gene of unknown function | NA | | | |
| c33204.0e0 SEQ ID NO: 28 | maker-pcu_contig_33204-snap-gene-0.0-mRNA-1:exon:0 | 0 | Gene of unknown function | Expressed gene of unknown function | NA | | | |
| c37797.0e0 SEQ ID NO: 31 | maker-pcu_contig_37797-snap-gene-0.0-mRNA-1:exon:0 | 0 | Glutamyl-tRNA synthetase | glutamyl-tRNA synthetase, putative [*Phytophthora infestans* T30-4] | NA | | | |
| c3923.5e3 SEQ ID NO: 32 | maker-pcu_contig_3923-snap-gene-0.5-mRNA-1:exon:3 | 3 | U3 small nucleolar RNA-associated protein 7 | conserved hypothetical protein [*Phytophthora infestans* T30-4] | NA | | | |
| c443.8e10 SEQ ID NO: 33 | maker-pcu_contig_443-snap-gene-0.8-mRNA-1:exon:10 | 10 | Gene of unknown function | hypothetical protein PITG_03070 [*Phytophthora infestans* T30-4] | NA | | | |
| c5641.0e0 SEQ ID NO: 42 | maker-pcu_contig_5641-snap-gene-0.0-mRNA-1:exon:0 | 0 (S) | Conserved gene of unknown function | conserved hypothetical protein [*Phytophthora infestans* T30-4] | NA | | | |
| c86.17e43 SEQ ID NO: 50 | maker-pcu_contig_86-snap-gene-0.17-mRNA-1:exon:43 | 43 | Conserved gene of unknown function | conserved hypothetical protein [*Phytophthora infestans* T30-4] | NA | | | |

*Redundant exon in the same gene
(D) Phytophthora infestans, Phytophthora capsici and Hyaloperonospora arabidopsidis protein sequences
(S) Putative single-copy gene according to self-BLASTP analyses The foregoing is illustrative of the present invention, and is not to be construed as limiting thereof. The invention is defined by the following claims, with equivalents of the claims to be included therein.

That which is claimed is:

1. A method of distinguishing between a type of *Pseudoperonospora cubensis* that infects cucumber and cantaloupe and a type of *P. cubensis* that infects pumpkin, watermelon, and squash, the method comprising:

contacting an environmental sample or a sample taken from a plant with a first oligonucleotide that hybridizes to the nucleotide sequence of SEQ ID NO:16 and/or a fragment thereof, but not to the nucleotide sequence of SEQ ID NO:52, and/or fragment thereof, and/or a second oligonucleotide that hybridizes to the nucleotide sequence of SEQ ID NO:52, and/or a fragment thereof, but not to the nucleotide sequence of SEQ ID NO:16, and/or fragment thereof;

detecting whether the nucleotide sequence of SEQ ID NO:16, and/or fragment thereof, is present by detecting binding between the first oligonucleotide and the nucleotide sequence of SEQ ID NO:16, and/or fragment thereof, and/or whether the nucleotide sequence of SEQ ID NO:52, and/or fragment thereof, is present by detecting binding between the second oligonucleotide and the nucleotide sequence of SEQ ID NO:52, and/or fragment thereof;

identifying a type of *P. cubensis* that infects cucumber and cantaloupe when binding is detected between the first oligonucleotide and the nucleotide sequence of SEQ ID NO:16, and/or fragment thereof, and identifying a type of *P. cubensis* that infects pumpkin, watermelon, and squash when binding is detected between the second oligonucleotide and the nucleotide sequence of SEQ ID NO:52, and/or fragment thereof, thereby distinguishing the type of *P. cubensis* that infects cucumber and cantaloupe from the type of *P. cubensis* that infects pumpkin, watermelon, and squash in the sample, and treating pumpkin, watermelon and squash crops when the type of *P. cubensis* that infects pumpkin, watermelon, and squash is identified and treating cucumber and cantaloupe crops when the type of *P. cubensis* that infects cucumber and cantaloupe is identified.

2. A method of distinguishing a type of *Pseudoperonospora cubensis* that infects cucumber and cantaloupe from a type of *P. cubensis* that infects pumpkin, watermelon, and squash, the method comprising:

contacting an environmental sample or a sample taken from a plant with a pair of oligonucleotides that hybridize to the nucleotide sequence of SEQ ID NO:16, and/or a fragment thereof, and to the nucleotide sequence of SEQ ID NO:52, and/or a fragment thereof, under conditions whereby nucleic acid amplification can occur, thereby producing an amplification product;

detecting whether the nucleotide sequence of SEQ ID NO:16, and/or fragment thereof, is present by detecting binding between the amplification product and a first oligonucleotide probe that hybridizes to the nucleotide sequence of SEQ ID NO:16, and/or fragment thereof, and not to the nucleotide sequence of SEQ ID NO:52, and/or fragment thereof, and/or whether the nucleotide sequence of SEQ ID NO:52, and/or fragment thereof, is present by detecting binding between the amplification product and a second oligonucleotide probe that hybridizes to the nucleotide sequence of SEQ ID NO:52, and/or fragment thereof, and not to the nucleotide sequence of SEQ ID NO:16 and/or fragment thereof;

identifying a type of *P. cubensis* that infects cucumber and cantaloupe when binding is detected between the amplification product and the first oligonucleotide probe, and identifying a type of *P. cubensis* that infects pumpkin, watermelon, and squash when binding is detected between the amplification product and the second oligonucleotide probe, thereby distinguishing the type of *P. cubensis* that infects cucumber and cantaloupe from the type of *P. cubensis* that infects pumpkin, watermelon, and squash, and treating pumpkin, watermelon and squash crops when the type of *P. cubensis* that infects pumpkin, watermelon, and squash is identified and treating cucumber and cantaloupe crops when the type of *P. cubensis* that infects cucumber and cantaloupe is identified.

3. The method of claim 1, wherein the first oligonucleotide and the second oligonucleotide each comprise about 20 to about 500 consecutive nucleotides or about 15 to 50 consecutive nucleotides, or any combination thereof, which hybridize to the nucleotide sequence of SEQ ID NO:16 or SEQ ID NO:52.

4. The method of claim 1, wherein the cucurbit plant is a wild cucurbit, a cucurbit breeding line, or a commercial cucurbit line.

5. The method of claim 1, wherein the cucurbit plant is a *Cucumis* spp., *Cucurbita* spp., *Citrullus* spp., *Lagenaria* spp., or *Luffa* spp.

6. The method of claim 1, wherein the cucurbit plant is a cucumber plant, a watermelon plant, a squash plant, a pumpkin plant, and/or a cantaloupe plant.

7. The method of claim 2, wherein the pair of oligonucleotides comprises a first oligonucleotide and a second oligonucleotide, wherein the first oligonucleotide and the second oligonucleotide each comprise about 5 to about 500 consecutive nucleotides or about 20 to 50 consecutive nucleotides, or any combination thereof, which hybridize to the nucleotide sequence of SEQ ID NO:16 or SEQ ID NO:52.

8. The method of claim 2, wherein the cucurbit plant is a wild cucurbit, a cucurbit breeding line, or a commercial cucurbit line.

9. The method of claim 2, wherein the cucurbit plant is a *Cucumis* spp., *Cucurbita* spp., *Citrullus* spp., *Lagenaria* spp., or *Luffa* spp.

10. The method of claim 2, wherein the cucurbit plant is a cucumber plant, a watermelon plant, a squash plant, a pumpkin plant, and/or a cantaloupe plant.

* * * * *

UNITED STATES PATENT AND TRADEMARK OFFICE
CERTIFICATE OF CORRECTION

PATENT NO. : 11,560,600 B2
APPLICATION NO. : 16/331191
DATED : January 24, 2023
INVENTOR(S) : Quesada-Ocampo et al.

Page 1 of 1

It is certified that error appears in the above-identified patent and that said Letters Patent is hereby corrected as shown below:

On the Title Page

(56) References Cited, FOREIGN PATENT DOCUMENTS: Please correct "EP 2444498" to read --EP 2444496--

In the Specification

Column 12, Line 45: Please correct "+5%, +1%, +0.5%" to read --±5%, ±1%, ±0.5%--

Column 44, Line 2: Please correct "RNALater@" to read --RNALater®--

Column 44, Line 34: Please correct "30-1001 µl" to read --30-100 µl--

Column 45, Line 26: Please correct ">2" to read --≥2--

Column 45, Line 55: Please correct "1e° 5" to read --1e$^{-05}$--

Column 46, Line 20: Please correct "72'" to read --72°--

Column 49, Lines 63-64: Please remove the paragraph break between "2014)." and "In"

Column 72, Table 6, Validation results for c5058.0e1 SEQ ID NO: 38: Please insert --*-- into the cell for Validation results Column 73, Table 6, Validation results for c5058.0e2 SEQ ID NO: 38: Please insert --*-- into the cell for Validation results Column 73, Table 6, Forward primer for c5058.1e3 SEQ ID NO: 37: Please delete "*" from the cell for Forward primer Signed and Sealed this
                    Twenty-third Day of May, 2023

Katherine Kelly Vidal
*Director of the United States Patent and Trademark Office*